(12) United States Patent
Chapman et al.

(10) Patent No.: US 7,199,082 B1
(45) Date of Patent: Apr. 3, 2007

(54) METHODS FOR EXTENDING THE FRESHNESS OF CUT FLOWERS, ORNAMENTAL TREES, AND PLANT CUTTINGS

(75) Inventors: Kent D. Chapman, Denton, TX (US); Shea Austin-Brown, Bowie, TX (US)

(73) Assignee: University of North Texas, Denton, TX (US)

( * ) Notice: Subject to any disclaimer, the term of this patent is extended or adjusted under 35 U.S.C. 154(b) by 250 days.

(21) Appl. No.: 09/702,374

(22) Filed: Oct. 30, 2000

Related U.S. Application Data

(60) Provisional application No. 60/162,178, filed on Oct. 28, 1999.

(51) Int. Cl.
*A01N 3/02* (2006.01)
*A01N 37/18* (2006.01)

(52) U.S. Cl. .................. 504/115; 504/149; 504/339

(58) Field of Classification Search ............... 504/114, 504/138, 149, 339, 115
See application file for complete search history.

(56) References Cited

U.S. PATENT DOCUMENTS

| | | | | |
|---|---|---|---|---|
| 4,017,084 | A | * | 5/1990 | Bergmann et al. |
| 5,152,989 | A | * | 10/1992 | Kemp .................. 424/750 |
| 5,506,224 | A | * | 4/1996 | della Valle et al. .......... 514/182 |
| 5,580,857 | A | * | 12/1996 | Oden ..................... 514/25 |
| 5,670,366 | A | | 9/1997 | Wang .................. 435/252.33 |
| 6,200,586 | B1 | * | 3/2001 | Lambie et al. ............. 424/417 |
| 6,426,105 | B1 | | 7/2002 | Palta et al. .............. 426/331 |

FOREIGN PATENT DOCUMENTS

| | | | |
|---|---|---|---|
| CS | 195040 | * | 1/1980 |
| DE | 4017084 | A | 5/1990 |
| GB | 2282327 | A | 4/1995 |
| WO | WO 99/23889 | | 5/1999 |

OTHER PUBLICATIONS

Registry Copyright 2004 ACS on STN—"N-lauroylethanolamine", "N-steartoylethanolamine".*
Ryu et al., "Inhibition of Phospholipas D by lysophosphatidyl-ethanolamine, a lipid-derived senescence retardant,"*Proc. Natl. Acad. Sci. USA*, 94:12717-21, 1997.
Abstract, Tripathy et al., "N-acylethanolamines in signal transduction. Attenuation of alkalinization response and activation of defense gene expression".
Abstract, Chapman et al., "N-acylethanolamines: formation and molecular composition of a new class of plant lipids".
European Search Report from European Patent Application No. EP 00 97 5506.
Austin-Brown et al., Database Accession No. AF195614—GI:6180158, Nov. 3, 1999.
Cui et al., Database Accession no. AF159139, Jul. 12, 1999.

* cited by examiner

*Primary Examiner*—S. Mark Clardy
(74) *Attorney, Agent, or Firm*—Jackson Walker L.L.P.

(57) ABSTRACT

Disclosed are compositions that comprise one or more N-acylethanolamine compounds for maintaining the freshness and appearance of cut flowers, floral products, decorative foliage, fruits, and other plant cuttings. More specifically, the present invention provides methods for treating and storing cut flowers, Christmas trees, fruits, and other severed plant parts that preserve the appearance, freshness, fragrance and/or aesthetic qualities of the botanical products. Using the disclosed compositions, the shelf life of cut flowers was substantially prolonged, in many cases 2 to 5 times longer than untreated flowers, with the treated flowers or foliage appearing healthy and viable, and without wilting, dehydration, leaf drop, or visible signs of senescence. Likewise, treatment of ornamental coniferous plants with the anti-senescent compositions delayed deterioration and leaf drop, while extending the overall appearance and quality of the plants and plant cuttings.

77 Claims, 10 Drawing Sheets

SEQUENCE LISTING

<160> NUMBER OF SEQ ID NOS: 15

<210> SEQ ID NO 1
<211> LENGTH: 1173
<212> TYPE: DNA
<213> ORGANISM: Nicotiana tabacum

<400> SEQUENCE: 1

```
gggaagtgct gggaggacat gttcaatgca ataaatcagg ctcgtcggtt gatttacatt    60
acaggatggt cagtgtacca cctagttaca cttgttaggg ataatggaaa agctgaggaa   120
agcatgttag gggaaattct caagaggaaa tcccaagaag gtgtgagagt actgcttctc   180
atatgggatg atcctacctc ttcgaagagc atcttgggat acaaaagtga aggaatcatg   240
ggaactagtg atgaagaaac tcgtcgctat tttaagcatt cttcagtgca cgtgctactt   300
tgtccccgtt ctgctggaaa agggcacagc tgggtcaaaa aacaggaaac tggaacaata   360
tacacacatc atcagaaaac tgtaatagtg gatgtggatg ctggtaatta ccagagaaag   420
attatcgctt tcgttggtgg ccttgatttg tgcaaagggc gttatgatac tccacaacac   480
cctatcttta aaacattgca aaatgtgcac aaagatgact atcatcagcc taactacacg   540
ggccctacta ccggttgtcc tagagaacct tggcatgatt acatagtcg gatcgagggg   600
cctgctgcat atgatgtcct aactaacttc gaggagcgct ggttgaaggc ttcaaagcgc   660
catggacttc aaaagatgaa agcttcacaa gatgatgcat tactccaact tgacaggatt   720
tccgacatat taaaaatagc tgatgtccct tgcctaggag aagatgatgc agatacgtgg   780
cacgtgcaga ttttccggtc gattgactcc aactctgtta aaggtttccc caaagatccc   840
aaagaagcca ctaacaagaa tctagtttgt ggcaagaatg tgctgataga tatgagcata   900
catactgcct atgtaaaggc aatccgagct gcccaacatt tcatctacat tgagaaccag   960
tacttcctag ggtcctcata caattggaat aactaccaag atttaggtgc aaataacttg  1020
ataccgatgg agattgctct aaaaattgcc aacaaaatac gggcaaatga gaggttttca  1080
gtatatataa ttgttcctat gtggccagag ggtgttccaa ccagtactgc tactcagaga  1140
atactttttt ggcaacacaa aaccatagag atg                               1173
```

<210> SEQ ID NO 2
<211> LENGTH: 391
<212> TYPE: PRT
<213> ORGANISM: Nicotiana tabacum

<400> SEQUENCE: 2

Gly Lys Cys Trp Glu Asp Met Phe Asn Ala Ile Asn Gln Ala Arg Arg
1               5                   10                  15

Leu Ile Tyr Ile Thr Gly Trp Ser Val Tyr His Leu Val Thr Leu Val
                20                  25                  30

Arg Asp Asn Gly Lys Ala Glu Glu Ser Met Leu Gly Glu Ile Leu Lys
            35                  40                  45

Arg Lys Ser Gln Glu Gly Val Arg Val Leu Leu Ile Trp Asp Asp
    50                  55                  60

Pro Thr Ser Ser Lys Ser Ile Leu Gly Tyr Lys Ser Glu Gly Ile Met

```
                65                  70                  75                  80
            Gly Thr Ser Asp Glu Thr Arg Arg Tyr Phe Lys His Ser Ser Val
                            85                  90                  95
            His Val Leu Leu Cys Pro Arg Ser Ala Gly Lys Gly His Ser Trp Val
                            100                 105                 110
            Lys Lys Gln Glu Thr Gly Thr Ile Tyr Thr His His Gln Lys Thr Val
                            115                 120                 125
            Ile Val Asp Val Asp Ala Gly Asn Tyr Gln Arg Lys Ile Ile Ala Phe
                130                 135                 140
            Val Gly Leu Asp Leu Cys Lys Gly Arg Tyr Asp Thr Pro Gln His
            145                 150                 155                 160
            Pro Ile Phe Lys Thr Leu Gln Asn Val His Lys Asp Tyr His Gln
                            165                 170                 175
            Pro Asn Tyr Thr Gly Pro Thr Thr Gly Cys Pro Arg Glu Pro Trp His
                            180                 185                 190
            Asp Leu His Ser Arg Ile Glu Gly Pro Ala Ala Tyr Asp Val Leu Thr
                            195                 200                 205
            Asn Phe Glu Glu Arg Trp Leu Lys Ala Ser Lys Arg His Gly Leu Gln
                210                 215                 220
            Lys Met Lys Ala Ser Gln Asp Ala Leu Leu Gln Leu Asp Arg Ile
            225                 230                 235                 240
            Ser Asp Ile Leu Lys Ile Ala Asp Val Pro Cys Leu Gly Glu Asp Asp
                            245                 250                 255
            Ala Asp Thr Trp His Val Gln Ile Phe Arg Ser Ile Asp Ser Asn Ser
                            260                 265                 270
            Val Lys Gly Phe Pro Lys Asp Pro Lys Glu Ala Thr Asn Lys Asn Leu
                            275                 280                 285
            Val Cys Gly Lys Asn Val Leu Ile Asp Met Ser Ile His Thr Ala Tyr
                            290                 295                 300
            Val Lys Ala Ile Arg Ala Ala Gln His Phe Ile Tyr Ile Glu Asn Gln
            305                 310                 315                 320
            Tyr Phe Leu Gly Ser Ser Tyr Asn Trp Asn Asn Tyr Gln Asp Leu Gly
                            325                 330                 335
            Ala Asn Asn Leu Ile Pro Met Glu Ile Ala Leu Lys Ile Ala Asn Lys
                            340                 345                 350
            Ile Arg Ala Asn Glu Arg Phe Ser Val Tyr Ile Ile Val Pro Met Trp
                            355                 360                 365
            Pro Glu Gly Val Pro Thr Ser Thr Ala Thr Gln Arg Ile Leu Phe Thr
                            370                 375                 380
            Gln His Lys Thr Ile Glu Met
            385                 390

<210> SEQ ID NO 3
<211> LENGTH: 10
<212> TYPE: PRT
<213> ORGANISM: Nicotiana tabacum

<400> SEQUENCE: 3

Gly Gly Gln His Lys Thr Ile Glu Met Met
1               5                   10

<210> SEQ ID NO 4
<211> LENGTH: 26
<212> TYPE: DNA
<213> ORGANISM: Nicotiana tabacum
<220> FEATURE:
```

```
<221> NAME/KEY: misc_feature
<222> LOCATION: (13)..(13)
<223> OTHER INFORMATION: N = ANY NUCLEOTIDE

<400> SEQUENCE: 4
catcatytcd atngtyttrt gytgcc                                          26

<210> SEQ ID NO 5
<211> LENGTH: 9
<212> TYPE: PRT
<213> ORGANISM: Nicotiana tabacum

<400> SEQUENCE: 5

Ile Tyr Thr His His Glu Lys Ala Cys
1               5

<210> SEQ ID NO 6
<211> LENGTH: 23
<212> TYPE: DNA
<213> ORGANISM: Nicotiana tabacum
<220> FEATURE:
<221> NAME/KEY: misc_feature
<222> LOCATION: (9)..(9)
<223> OTHER INFORMATION: N = ANY NUCLEOTIDE

<400> SEQUENCE: 6
athtayacnc aycaygaraa rac                                             23

<210> SEQ ID NO 7
<211> LENGTH: 11
<212> TYPE: PRT
<213> ORGANISM: Nicotiana tabacum

<400> SEQUENCE: 7

Cys Asn Ile Tyr Thr His His Glu Lys Ala Cys
1               5                   10

<210> SEQ ID NO 8
<211> LENGTH: 25
<212> TYPE: DNA
<213> ORGANISM: Nicotiana tabacum
<220> FEATURE:
<221> NAME/KEY: misc_feature
<222> LOCATION: (15)..(15)
<223> OTHER INFORMATION: N = ANY NUCLEOTIDE
<221> NAME/KEY: misc_feature
<222> LOCATION: (24)..(24)
<223> OTHER INFORMATION: N = ANY NUCLEOTIDE

<400> SEQUENCE: 8
gtyttytcrt grtgngtrta datng                                           25

<210> SEQ ID NO 9
<211> LENGTH: 8
<212> TYPE: PRT
<213> ORGANISM: Nicotiana tabacum

<400> SEQUENCE: 9

Glu Cys Trp Phe Trp Cys Gly Gly
1               5

<210> SEQ ID NO 10
<211> LENGTH: 20
<212> TYPE: DNA
<213> ORGANISM: Nicotiana tabacum

<400> SEQUENCE: 10
```

```
gartgytggt tytggtgygg                                               20

<210> SEQ ID NO 11
<211> LENGTH: 8
<212> TYPE: PRT
<213> ORGANISM: Nicotiana tabacum

<400> SEQUENCE: 11

His Gly Lys Cys Trp Glu Asp Met
1               5

<210> SEQ ID NO 12
<211> LENGTH: 24
<212> TYPE: DNA
<213> ORGANISM: Nicotiana tabacum
<220> FEATURE:
<221> NAME/KEY: misc_feature
<222> LOCATION: (6)..(6)
<223> OTHER INFORMATION: N = C, G, A or T

<400> SEQUENCE: 12
cayggnaart gytgggarga yatg                                         24

<210> SEQ ID NO 13
<211> LENGTH: 9
<212> TYPE: PRT
<213> ORGANISM: Nicotiana tabacum

<400> SEQUENCE: 13

Glu Glu Pro Glu Asn Met Glu Cys Gly
1               5

<210> SEQ ID NO 14
<211> LENGTH: 25
<212> TYPE: DNA
<213> ORGANISM: Nicotiana tabacum
<220> FEATURE:
<221> NAME/KEY: misc_feature
<222> LOCATION: (17)..(17)
<223> OTHER INFORMATION: N = C, G, A or T

<400> SEQUENCE: 14
crcaytccat rttytcnggy tcytc                                        25

<210> SEQ ID NO 15
<211> LENGTH: 8
<212> TYPE: PRT
<213> ORGANISM: Nicotiana tabacum
<220> FEATURE:
<221> NAME/KEY: misc_feature
<222> LOCATION: (2)..(2)
<223> OTHER INFORMATION: X = ANY AMINO ACID
<221> NAME/KEY: misc_feature
<222> LOCATION: (4)..(7)
<223> OTHER INFORMATION: X = ANY AMINO ACID

<400> SEQUENCE: 15

His Xaa Lys Xaa Xaa Xaa Xaa Asp
1               5
```

METHODS FOR EXTENDING THE FRESHNESS OF CUT FLOWERS, ORNAMENTAL TREES, AND PLANT CUTTINGS

The present application is a continuing application that claims priority to U.S. Provisional Patent Application Ser. No. 60/162,178, filed Oct. 28, 1999, the entire contents of which is specifically incorporated herein by reference in its entirety.

1.0 BACKGROUND OF THE INVENTION

1.1 Field of the Invention

The present invention relates to floral and botanical preservative compositions and methods for preserving the freshness and appearance of cut flowers, as well as extending the shelf-life of floral products, coniferous trees, ornamental plants, plant cuttings, severed plant parts, and the like.

Disclosed are compositions and methods for prolonging the vase life and preserving the beauty, fragrance, and aesthetic characteristics of the cut flowers. The invention also provides methods for delaying or preventing the onset of symptoms associated with senescence in a plant, plant tissue, or plant cell, by inhibiting or reducing the activity of the plant enzyme phospholipase D. Also disclosed is a novel amino acid sequence comprising an antigenic fragment of a plant phospholipase D (PLD) polypeptide, and the corresponding polynucleotide sequence that encodes this polypeptide.

1.2 Description of Related Art

A plant receives essential nutrients and water to sustain life from the soil. Nutrients and water are absorbed through the roots of the plant and travel to the leaves and flowers through a network of ducts. When flowers and leaves are removed from the plant, the nutrient reserve in the leaves and flowers of the plant part rapidly becomes exhausted, whereupon the flowers wilt.

When fresh cut flowers or plant cuttings are exposed to ethylene, initially the vegetal material changes color by yellowing of the leaves or petals. Thereafter, the vegetal material acquires a burned appearance, whereinafter ultimate necrosis of the vegetal material occurs. Producers of fresh cut flowers or plant cuttings have also employed ethylene scavengers or ethylene inhibitors to avoid the build-up of ethylene within packages containing the plant material. Although it is possible to decrease the production rate of ethylene by decreasing the temperature, ethylene production by the vegetal material is not entirely suppressed. Unfortunately, when the plant material is subjected to an unexpected increase in temperature, ethylene production rapidly resumes and irreversible damage to the appearance of the plant material occurs.

Causes for which the freshness of flower petals of the cut flowers can be reduced or lost, include, for example, such bacterial decay or rotting and blockage of the vessels occurring in the stem portions of the cut flowers in the vase water where the cut flowers are soaked, as well as, full exhaustion of nutrients, and an increased concentration of ethylene, an aging hormone, inside the plant bodies of the cut flowers, or others.

1.2.1 Increasing the Life of Cut Flowers and Floral Cuttings

To prolong the life of cut flowers, the water and nutrients normally supplied to the leaves and flowers by the roots must be provided. Traditionally, to prolong the life of fresh cut flowers, the stem of the flower is placed in water. Although water prolongs the freshness of cut flowers to a certain degree, it does not contain the essential nutrients required to prolong the life of the flower.

Many types of treatments have been used to keep cut flowers or other plant parts in a fresh state. For example, conventional methods have employed such techniques as stem cutting under water, hot water treatments, charring of stem ends, stem crushing and the like. All of these methods are considered to be effective in attaining an increased level of water uptake of cut flowers, however, it is difficult to obtain a satisfactory level of water uptake. In fact, some of them will show only a little improvement of water uptake, if applied to specific cut flowers. Others have employed additives to the aqueous solutions that contain the flowers or plant parts such as bactericides (i.e. alum, vinegar, bleaching agents and the like).

To prevent the microbial decay of the vessels in the stems of cut flowers, bactericides and/or fungicides have been used as additives to aqueous solutions containing the flowers or plant parts to reduce microbial degradation and rotting of the cut flowers and plant parts. Likewise, the addition of precipitation agents, such as aluminum sulfate, have been used as additives to aqueous solutions containing the flowers or plant parts to cause settling of dirt particles and other solids as formed in the vase water to reduce blocking of the stems. Similarly, various surfactants have been used as cut flower preservatives in order to enhance the water uptake by the cut flowers. To avoid full exhaustion of nutrients in cut flowers, the use of metabolizable substrates such as saccharides and the like has been described to promote extended life of the severed plant parts.

In order to prevent an increase in the concentration of ethylene that is an aging hormone of plants, Veen et al. described a treatment involving silver thiosulfate (abbreviated as "STS") (1978). STS was shown to inhibit the action of ethylene and to extend the freshness of flower petals for a prolonged period. This treatment was especially useful in preserving cut flowers such as carnations, perennial baby's breath, and the like, which are particularly sensitive to ethylene-induced wilting. A limitation of the use of STS, however, involves the potential environmental pollution due to its containing the heavy metal, silver as its active ingredient. In countries where the use of STS has been restricted legally (e.g., The Netherlands), amino-oxyacetic acids have been developed that inhibit biosynthesis of ethylene (*Hortscience*, 1980). This compound is however disadvantageous in that it is expensive, effective on limited flowering species, and is overall less effective than STS.

Although other compounds have been described in the literature that inhibit ethylene biosynthesis (e.g., L-α-(2-aminoethoxyvinyl)glycine and 2-aminoisobutyric acid), these are not practically used in the floral industry because of their high prices and relatively poor attainable effects (Serrano et al., 1990; Japanese Patent Application "Kokai" No. 238901/93).

It is known that the life of cut flowers can be increased by adding preserving agents to the water in which the flowers are standing (Rompp, 1966; Aarts, 1957). Although, the preserving action of the agents described is limited. This also applies to those agents that consist of a mixture of sugar or a sugar derivative, a pH stabilizer, an organic carboxylic acid with a low molecular weight and a microbicide (e.g., German Pat. Appl. Publ. 1,542,832), hydrazine sulphate and gibberellic acid (e.g., Swiss Patent No. 432,115) and N-(trifluoromethyl)-N-(dichlorofluoromethylsulphenyl)-aminobenzoic acid phenylcarboxylic acid esters (e.g., German Pat. Appl. Publ. No. 2,654,349). These compounds are not always satisfactory when fairly small amounts are used, and in some cases cause damage to the leaves if used in a fairly high concentration.

A variety of other compounds, including calcium nitrate, cobalt chloride, pyrusulphuric acid, aminoethoxyvinylglycine, dichlorodimethylhydantoin, aminooxyacetic acid, 2,4-dinitrophenol, triadimenol, 1-methylcyclopropene, and 1-1-dimethyl-4-(phenylsulfonyl) semicarbazide have been described in various publications and trade journals as floral additives, although the results of each compound vary widely depending upon the concentration, application, and flower to be preserved.

1.3 Deficiencies in the Prior Art

The fresh cut flower industry represents a multi-billion dollar business worldwide, and a multi-million dollar industry in the United States alone. Worldwide demand for floral arrangements, floral and botanical cuttings, and ornamental trees has exceeded the capacity of local growers and producers. Likewise, the year-round demand for such products is confounded by regional climatic conditions, length of local growing seasons, and the need for vast commercial networks of product growth, harvest, shipping, and delivery. As a result, it is now common that floral crops cultivated in one region of the globe, are often harvested, packaged, and transported many thousands of miles before final delivery to the end-user. Owing to the perishable nature of these commodities, it has become economically important to prolong the quality and appearance of such products from the time the crop is harvested until it is delivered to wholesalers, retailers, and ultimately consumers. Necessarily, the longer that the quality of these fresh cut flowers or floral products may be preserved, the greater the time and distance may be from grower to consumer.

Likewise, once such products are purchased, the longer they last in a vase or flower arrangement, the longer the purchaser has to enjoy the aesthetic qualities, fragrance, and appearance of those cut flowers. It is therefore an advantage to both commercial producer and the consumer to store, handle, and display fresh cut flowers in such a manner that they last as long as possible, and remain in their highest possible quality. It is only natural that a pleased retailer is likely to utilize wholesalers or growers that maintain such qualities, and that a satisfied consumer is likely to make a repeat purchase from the same florist or retailer.

In a similar fashion, preservation of plant foliage, garlands, leaves, wreaths, tree branches, ornamental trees, and related plant materials in ways that extend their appearance and usefulness in the decorative arts is of ultimate concern to the ornamental plant industries, such as, for example, the multi-million dollar Christmas tree/holiday tree growers worldwide.

Accordingly, it can be seen that there is a real and continuing need for effective preservation formulations to preserve fresh cut flowers and other floral and foliage products that significantly delay the onset of wilt, drying, stem bending, flower senescence, and related deterioration of the product. This invention has as its primary objective the fulfillment of this need.

In addition, another objective of the present invention is to provide a medium that preserves fresh cut flowers so that they can be enjoyed by the user for substantially longer periods of time than in the past.

Another objective of the present invention is to provide a method and compositions for general applicability to floral products to preserve the flowers, stems, or ornamental trees in their naturally appearing, and aesthetically pleasing states for longer periods of time.

2.0 SUMMARY OF THE INVENTION

The present invention overcomes these and other inherent limitations in the prior art by providing compositions and methods for preserving the freshness of cut flowers, fruits, foliage, and plant parts severed from growing plants.

In an overall and general sense, the method comprises treating freshly-harvested crops, or the cut stem portion or leaves of the cut flowers, floral or foliage as obtained by cutting off the root part of the florist plant with an effective amount of an anti-senescent compound to extend the shelf life or the appearance of the plant, cut flower, fruit or plant cuttings. The methods may alternatively involve soaking, shipping, storing, or dipping such plant parts in one or more solutions that comprise one or more of the active anti-senescent compounds disclosed herein. Likewise, the disclosed methods may alternatively comprise treating the roots or leaves of the floral or foliage plant under cultivation in a field, greenhouse, or a pot, with one or more anti-senescent compounds of the present invention in an amount effective to maintain the freshness or to extend the aesthetic qualities of the plant or flower once harvested. Such methods may be employed individually, or alternatively, may be combined or sequentially performed from growth, through harvest and shipment, to final use and display of the products by the consumer.

In one embodiment, the invention provides a composition comprising at least a first N-acylethanolamine compound of the formula:

wherein R is optionally branched or straight chain, saturated or unsaturated $C_8$–$C_{20}$ alkyl, in an amount effective to prolong the freshness or the aesthetic appearance of flowers, fruit, or plant parts.

Exemplary saturated NAE compounds include, for example, NAE10:0 (N-caproylethanolamine), NAE11:0, NAE12:0 (N-lauroylethanolamine), NAE13:0, NAE14:0 (N-myristoylethanolamine), NAE15:0, NAE16:0 (N-palmitoylethanolamine), NAE17:0, NAE18:0 (N-stearoylethanolamine), NAE19:0, and NAE20:0 (N-arachidoylethanolamine), with the compounds NAE10:0, NAE12:0, NAE14:0, NAE16:0, NAE18:0 and NAE 20:0 being particularly preferred.

Exemplary unsaturated NAE compounds include, for example, NAE10:1, NAE10:2, NAE10:3, NAE10:4, NAE10:5, NAE10:6, NAE11:1, NAE11:2, NAE11:3, NAE11:4, NAE11:5, NAE11:6, NAE12:1, NAE12:2, NAE12:3, NAE12:4, NAE12:5, NAE12:6, NAE13:1, NAE13:2, NAE13:3, NAE13:4, NAE13:5, NAE13:6, NAE14:1, NAE14:2, NAE14:3, NAE14:4, NAE14:5, NAE14:6, NAE15:1, NAE15:2, NAE15:3, NAE15:4, NAE15:5, NAE15:6, NAE16:1 (N-palmitoleoylethanolamine), NAE16:2, NAE16:3, NAE16:4, NAE16:5, NAE16:6, NAE17:1, NAE17:2, NAE17:3, NAE17:4, NAE17:5, NAE17:6, NAE18:1 (N-vaccenoylethanolamine), NAE18:2 (N-linoleoylethanolamine), NAE18:3 (N-linolenoylethanolamine), NAE18:4, NAE18:5, NAE18:6, NAE19:1, NAE19: 2, NAE19:3, NAE19:4, NAE19:5, NAE19:6, NAE20:1, NAE20:2 (8,11-icosadienoylethanolamine), NAE20:3 (5,8, 11-icosatrienoylethanolamine), NAE20:4 (N-arachidonoylethanolamine), NAE20:5, and NAE20:6. More preferably, the unsaturated NAE compounds are selected from the group consisting of NAE10:1, NAE10:2, NAE11:1, NAE11:2, NAE11:3, NAE12:1, NAE12:2, NAE12:3, NAE13:1, NAE13:2, NAE13:3, NAE14:1, NAE14:2, NAE14:3, NAE15:1, NAE15:2, NAE15:3, NAE16:1, NAE16:2, and NAE16:3, which are more soluble in aqueous solution than the longer-chain, and more highly-unsaturated NAE compounds.

The compounds of the present invention are preferably formulated in aqueous solutions, and may optionally further comprise a nutrient source, such as a lipid, a sugar, or an amino acid, or a carbohydrate, such as lactose, dextrose, fructose, sucrose, glucose sorbitol, mannitol, or inositol.

The compositions and formulations of the anti-senescent compounds of the invention may also further optionally comprise a surfactant, such as polyoxyethylene sorbitan monolaurate, monopalmitate monostearate, ethoxylated alkyl phenols or hydrogenated oils, and may also further optionally comprise one or more salts or buffering agents as described below. Exemplary buffers for use in formulating the compounds of the invention include, but are not limited to, acetate, bicarbonate, citrate, succinate, malate, TRIS (Tris-(hydroxymethyl)-aminomethane), MES (2-[N-Morpholino]-ethanesulfonic acid), HEPES (N-[2-hydroxyethyl]piperazine-N'-[2-ethanesulfonic acid]), MOPS (3-(N-Morpholino)-propanesulfonic acid), BES (N,N-Bis-(2-hydroxyethyl)-2-aminoethanesulfonic acid), and BIS-TRIS (Bis-(2-hydroxyethyl)-imino-tris-(hydroxymethyl)-methane).

As described below, the composition may further optionally comprise one or more osmoregulants, such as a salt, a carbohydrate, a polyol, or a polyethylene glycol. Likewise, they may contain one or more plant hormones such as auxins, gibberellins and cytokinins.

In related embodiments, the formulations of the active ingredients of the invention may further optionally comprise one or more antifungal, bacteriostatic, or bactericidal agents such as 8-hydroxyquinoline citrate, sodium dichloroisocyanurate, or 1,3-dichloro-5,5-dimethyhydantoin in an amount sufficient to retard or inhibit the growth of fungi or bacteria in the prepared solutions.

The formulations of the anti-senescent compounds may further comprise an alcohol, such as ethanol or isopropanol, particularly when manufacturing concentrated or stock solutions of the formulation, which may later be diluted as needed to prepare the final working solutions used to treat the plant or plant cuttings.

The compositions may also further optionally contain a second anti-senescent component. This component may be another distinct N-acylethanolamine compound (such as those described herein), or may be a commercially-available anti-senescent cut flower nutrient or preservative component such as Petalife® (8-hydroxyquinoline citrate), Oasis® (Smither's Oasis, Inc., Kent, Ohio), Rogard® (Gard Environmental Group, Carpentersville, Ill.), Everbloom® (8-hydroxyquinoline citrate), FloraLife® (Floralife, Inc., Walterboro, S.C.), Vita Flora® (Vita Products, Inc., Chandler, Ariz.), Aquaplus® (Syndicate Sales Inc., Kokomo, Ind.), Spring®, or Crystal Clear™ (Floralife, Inc., Walterboro, S.C.).

The invention also provides kits, typically packaged for wholesale, or retail distribution, that comprise the active NAE compound, or compositions or formulations thereof, along with suitable instructions for using the formulations to delay the senescence of a flower, fruit, or severed plant part. These kits may include, for example, measuring devices, applicators, measuring droppers, or other suitable means for applying or diluting the aqueous solution to the final appropriate concentration, or for directly administering the active ingredients to either a plant under cultivation, or to the flowers, fruit, or plant parts post-harvest.

In another embodiment, the invention provides methods of use of the disclosed compounds, compositions, formulations, and kits, in the treatment of cut flowers, fruits, severed plant parts, or ornamental plant cuttings to prolong their senescence, and to extend their shelf life, appearance, or other aesthetic qualities. These methods generally involve providing to the plant, fruit, or plant part, an effective amount of a solution that comprises a senescence-delaying amount of a compound of the formula:

where R is optionally branched or straight chain, saturated or unsaturated $C_9$–$C_{20}$ alkyl; or a composition that comprises such a compound, and a horticulturally acceptable vehicle.

The method may be accomplished by directly applying the solution to the flower, fruit, or plant part, such as by spraying, soaking, transporting, and/or storing the cut flowers or severed plant parts in the solution for a length of time effective to delay the senescence.

The method may be accomplished by applying the solution to the flower, fruit, or plant part under ambient temperature conditions, or alternatively, under lower temperature conditions of from about 4° C. to about 15° C., such as typically provided for the shipment, storage, and commercial handling of cut flowers in the floral industry.

Alternatively, the method may involve providing the solution to the plant while it is still under cultivation. As such, the method may be accomplished by directly administering the solution to the roots, leaves, fruits, or flowers of the plant, preferably within a relatively short time period immediately before the plant parts are harvested. For example, the components may be provided to the plant under cultivation for a period of from about a few hours up to about a few days prior to harvesting to permit the plants to uptake the compound and disperse it throughout its tissues prior to harvesting the plant parts.

The methods described herein afford particular advantages by delaying the senescence of the plant, because it has been demonstrated that a delay of the onset, or a reduction in the rate, or extent of senescence preserves or improves the appearance, fragrance, freshness, and/or aesthetic characteristics of the flower, fruit, or plant part, by effectively reducing the rate at which the leaves drop off, the flower or stems wilt, or the flowers lose their coloration, fragrance, or physical beauty, or the plant parts become dehydrated, or otherwise unsuitable for continued display or use.

Delaying this senescence reduces the droop, wilt, bloom loss, leaf loss, needle drop, and rate of dehydration of cut flowers and ornamental cuttings, including substantially whole trees such as Christmas trees, etc., and provide an extended time frame for harvesting, shipping, selling, and displaying the floral or foliage crops.

Delaying the rate at which the quality of such crops decline prolongs or extends the appearance, taste, quality, or shelf life of harvested fruit, and may provide additional time for harvesting and delivering the crop to wholesalers and retailers, and ultimately the consumer.

The plant parts which may achieve benefit of the present invention include bulbs, blooms, buds, flowers, petals, stems, branches, roots, rhizomes, bracts, fruits, seeds, needles, and leaves, with flowers such as roses, orchids, tulips, daffodils, hyacinths, carnations, chrysanthemums, baby's breath, daisies, gladiolus, agapanthus, anthuria, *Protea, Heliconia, Strilitzia*, lilies, asters, irises, delphiniums, liatris, lisianthus, statis, stephanotis, freesoa, dendrobiums, sunflowers, snap dragons, and ornamental foliage finding particular benefit when contacted with the active compounds of the present invention.

2.1 N-Acylethanolamine (NAE) Compounds as Anti-Senescent Agents

The present invention provides N-acylethanolamine (NAE) compounds for use in the manufacture of a preservative agent for floral and foliage products, and in the treatment and preservation of such botanical products to extend their shelf-life, appearance, and decrease the perishability of such products from cultivation to consumer. These compounds have the general formula (I) as shown below:

RCONHCH$_2$CH$_2$OH    (I)

where R is optionally branched or straight chain, saturated or unsaturated $C_8$–$C_{20}$ alkyl. Although the unsaturated $C_8$–$C_{20}$ alkyl derivatives are particularly preferred, in some instances, it may be desirable to employ unsaturated acyl moieties such as oleic, linoleic, linolenic or arachidonic moieties. In any event, it is believed that medium to long carbon chains will provide the most effective derivatives. A shorthand notation of such compounds is NAEX:Y, where X is an integer representing acyl chain length, and Y is an integer representing the number of double bonds. Particularly preferred compounds include, for example, NAE10:0, NAE11:0, NAE12:0, NAE13:0, NAE14:0, NAE15:0, and NAE16:0, while compounds such as NAE:17:0, NAE18:0, NAE19:0, and NAE20:0 may also find particular usefulness in the practice of certain aspects of the invention. Likewise, the saturated NAEs such as NAE10:1, NAE10:2, NAE10:3, NAE11:1, NAE11:2, NAE11:3, NAE12:1, NAE12:2, NAE12:3, NAE13:1, NAE13:2, NAE13:3, NAE14:1, NAE14:2, NAE14:3, NAE15:1, NAE15:2, NAE15:3, NAE16:1, NAE16:2, NAE16:3, NAE17:1, NAE17:2, NAE17:3, NAE18:1, NAE18:2, NAE18:3, NAE19:1, NAE19:2, NAE19:3, NAE20:1, NAE20:2, and NAE20:3 are also contemplated by the inventors to be useful in certain of the methods disclosed herein.

A method is provided for preserving the freshness or appearance of cut flowers or plant cuttings. This method generally involves contacting cut flowers or plant cuttings with an effective amount of a composition that comprises at least one NAE compound as described herein. The invention also provides cut flowers, foliage, ornamental trees, fruit, or other plant parts that are preserved by the method of the invention.

When the cut stem portion of cut flower is treated in accordance with the method of the third aspect of the present invention, the treatment can be conducted by soaking the cut stem portion of the plant for at least about 1 hour or longer (for example, from about 1 to about 24 or longer hours) in an aqueous solution containing the anti-senescent compound at a concentration in a range of from about 0.2 to about 800 μM, so as to make the effective compound adsorbed by the cut flower.

On the other hand, when a plant of the florist crop under cultivation is to be treated immediately prior to the harvesting of the cut flowers or plant parts, it is possible to adopt a method in which the treatment is conducted by spraying the cultivating soil or other medium with an aqueous solution containing the compound of the general formula (I) at an increased concentration higher than the above-described concentration range so that said compound can penetrate into the cultivation medium, be taken up by the living plant, and thereby maintained in a sufficient concentration in the plant parts, such than when severed from the growing plant, the composition remains within the tissues and vascular network of the stems flowers, and/or petals of the severed flowers or plant parts.

2.2 Compositions Comprising One or More Anti-Senescent Ingredient(s)

While the anti-senescent compositions of the present invention may be utilized directly, it may be desirable in certain instances to formulate the active ingredients in various formulations for commercial use, sale, packaging, or consumer convenience and utilization. In certain embodiments, the inventors contemplate the use of particular formulations of one or more of the ingredients disclosed herein. These formulations may further comprise one or more anti-senescent compounds, or additional compounds to provide cut flower preservatives and formulations having enhanced properties.

For example, such compositions may comprise one or more of the anti-senescent ingredient(s) in combination with one or more plant nutrients to sustain the shelf life of the plant part or flower. As such, any of the great number of plant nutrients known to the art may be used in the compositions of the present invention. For example, the compositions may be formulated to contain one or more sugars such as glucose or dextrose. This is employed as a base material to which the other ingredients are added in the desired quantities and proportions. The sugar provides a source of nutrition capable of being utilized by the flower or other plant so that it will continue to mature and develop. The compositions may also contain other saccharides (including mono- and poly-saccharides) or carbohydrates, for example sugars or sugar derivatives, such as sucrose, fructose, arabinose, lactose, adonitol, mannitol, xylose, xylotol, inositol, or the like.

The compositions and formulations of the present invention may also further comprise a fungicidal, virucidal, bactericidal, bacteriostatic, or microbicidal agent, or a combination of two or more such compounds.

The compositions and formulations of the present invention may also further comprise one or more disinfectants such as citric acid, acetic acid, succinic acid, malic acid, tartaric acid, or lactic acid, or the like. Such disinfectants may be present in the formulations in an amount of from about 0.01% to about 1%, with concentrations on the order of about 0.05% to about 0.1% being particularly preferred.

The compositions and formulations of the present invention may also further comprise one or more water-soluble vitamins (such as, e.g., ascorbate, niacin, thiamine, cobalamin, pyrridoxine, and/or nicotinic acid) or alternatively, one or more organic supplements such as myoinositol. In these embodiments, the vitamins or organic supplements may be present in the formulations in an amount of from about 0.5 μg/L to about 5000 mg/L, with concentrations on the order of from about 5 μg/L to about 500 mg/L being particularly preferred.

The compositions and formulations of the present invention may also further include an inorganic salt or mineral (including inorganic salts, such as those of magnesium, boron or aluminum), or one or more ionized metals such as those selected from the group consisting of calcium, magnesium, potassium, sodium and iron.

The compositions and formulations may also further comprise one or more agents to buffer or regulate the pH of the compositions. For example, a salt such as sodium bicarbonate may be added to the composition in an amount sufficient to maintain the pH of the composition to a desired value between about 5.5 and about 7.5. Exemplary buffering agents include bicarbonate, phosphate, Tris, Bis-Tris, MOPS, HEPES, BES, MES and the like. Such buffering agents may be present in the formulations in an amount of from about 1 mM to about 500 mM, with concentrations on the order of about 5 mM to about 200 mM being particularly preferred.

Likewise, the anti-senescent compositions and formulations may further comprise one or more osmoregulating agents, such as glycerol, sorbitol, or one or more salts in an amount sufficient to maintain the osmotic pressure of the composition. For example, the composition may comprise from about 0.4% to about 3.0% sodium or potassium chloride by weight of the composition. Such agents may be desirable to prevent dessication of the cut flower and plant parts, or to maintain cellular integrity and osmotic pressure of the solution into which the plant parts are placed.

The compositions described herein may also optionally comprise one or more antifoaming agents in an amount sufficient to retard or reduce the formation of foam by the composition. Exemplary antifoaming agents include silicones, alcohols and lipids. Commercially available antifoaming agents that may be employed in the preparation of the compositions of the present invention include, for example, biphenylhexamethicone, dimethicone, dimethiconol, hexamethyldisiloxane, petroleum distillate, phenyl trimethicone, silica silylate, simethicone, tetraethyl decynediol and trimethylsilocysilcate.

The compositions of the present invention may further contain one or more surfactants, miscibility-promoting substances, and/or surface-active substances. Exemplary surface-active substances are selected from the group consisting of lipids, phospholipids such as cephalin, lecithin, phosphatidic acid and the like, and glycolipids such as e.g., sophorolipid and the like. These surface-active substances can increase the dispersability of other components contained in the preservative in water, and at the same time, can accelerate the uptake of the solution into the plant parts, stems, or flowers. Numerous commercially available surfactants can be used in accordance with the present invention including, for example, polyoxyethylene sorbitan monolaurate, polyoxyethylene sorbitan monopalmitate, polyoxyethylene sorbitan monostearate, ethoxylated alkyl phenols, and hydrogenated castor oils. The surfactants used in accordance with the present invention are preferably nonionic, however, amphoteric and anionic surfactants can also be used in the compositions described herein. Examples of nonionic surfactants include, for example, alcohol ethoxylates, alkylphenol ethoxylates, carboxylic acid esters, glycerol esters, polyoxyethylene esters, anhydrosorbitol esters, ethoxylated anhydrosorbital esters, glycol esters of fatty acids, polyoxyethylene fatty acid amides, amide esters, amine oxides, and polyoxyethylene-co-oxypropylenes. Examples of amphoteric surfactants include, for example, imidazoline derivatives, imidazolinium derivatives and betaine derivatives. Anionic surfactants used in the composition described by the present invention include, for example, alkyl sulfates, alkylbenzenesulfonates, alkylarenesulfonates, naphthalenesulfonates, petroleum sulfonates, alcohol sulfates, phosphate esters, N-cylsarcosinates, alkyl monoglyceride sulfates, N-acyl methyltaurates, α-olefinsulfonates, polyalkoxycarboxylates and alkyl sulfoacetates.

The desired effects of the disclosed compositions may also be enhanced by the addition of small amounts of a wetting agent. For example, non-ionic surfactants such as "Tween," or other polyoxyethylene derivatives of hexitol anhydride partial long chain fatty acid esters, have been found to be especially suitable. The wetting agent must be compatible with the other ingredients of the composition and must not adversely affect plant life. The quantity of wetting agent must be limited, since too much wetting agent has been found to prevent absorption by the flower stem, resulting in rapid wilting. With wetting agents of the "Tween" type, the upper limit is typically on the order of about 20 to 25 ppm with lesser amounts often providing more desirable results. The wetting agent also insures that the water-conducting vessels and tissues of the flower stem will remain open in order for the blossoms to draw nutrient when necessary. In the NAE formulations described herein, the inventors have found that the concentration of Tween-20™ (polyoxyethylenesorbitan monolaurate), e.g., could be varied on the order of from about 0.001 ml/ml of alcohol to about 0.01 mL/mL of alcohol in concentrated solutions, without diminished results on final NAE solubility in reconstituted aqueous working solutions, or on the efficacy in tests with cut flowers.

The compositions of the present invention may also contain one or more plant hormones. Suitable plant hormones include, for example, auxin, cytokinin, gibberellin, brassinolide and the like. The content of the plant hormones in the preservative may be optionally varied depending upon the particular hormone used and other factors. However, generally, if added, the plant hormone is preferably used in the preservative in an amount of about 0.03% by weight or less in terms of the concentration of the hormone in the water used for the cut flowers. In certain circumstances, the hormone may be present in an amount of about 0.02% by weight or less in terms of the concentration of the hormone in the water used for the cut flowers, while in certain embodiments, the hormone may be present in an amount of about 0.01% by weight or less.

The compositions described herein may further optionally comprise an additional anti-senecent compound, such as, e.g., acetylsalicylic acid, acetylsalicylsalicylic acid, or derivatives thereof, in an amount sufficient to enhance water uptake by the cut flowers or plant parts. For example, addition of acetylsalicylic acid or acetylsalicylsalicylic acid in an amount ranging from about 0.005% to 0.025% by weight of the composition may be used to increase the uptake of solution by the cut flowers or severed plant parts.

The compositions and formulations of the invention may also further comprise one or more additional compounds known to be effective in increasing the shelf life of a cut flower or plant part. Such agents may include herbal and/or botanical extracts, such as an extract from eucalyptus leaves, chitosan, hinokitiol, tea catechin, flavonol, or extracts from grapefruit seed, or extracts from plant tissues enriched in naturally occurring NAEs (e.g., oilseeds) (Chapman et al., 1999).

The invention further concerns commercial formulations and packaging of the compositions disclosed herein and instructions for the use of these compositions in the preservation of cut flowers, decorative trees, garlands, wreaths, ornamentals, and other severed plant parts. It is understood that different formulations and different commercial packaging of these compositions may be utilized for different applications, flower species, or to prolong blooming or bloom life of the plant, or to provide an extended shelf-life in products such as decorative wreaths, garlands, branches, trees, etc.

2.3 Formulation of NF20-XL

An illustrative formulation comprising NAE12:0 as the active ingredient has been shown by the inventors to be particularly effective in prolonging the shelf life of floral and botanical products. This formulation, shown below, has been extensively tested for efficacy and for ease of use by the grower, wholesaler, retailer, or consumer. Formulation of the active ingredient(s) as an alcohol concentrate facilitates the preparation of "stock" solutions that when diluted in an aqueous solution dissolve readily to form the appropriate final "working" concentration. Several factors, including solubility in water, intended method of delivery, and the cost of materials guide the overall strategy for the formulation of both concentrated and diluted forms of the active ingredients.

The exemplary formulation, designated NF20-XL, comprises:
2.0 g NAE12:0;
0.2 mL Tween-20; and
1.0 g Soy Lecithin (de-oiled granules)
dissolved in approximately 20 mL of alcohol, such as isopropanol.

To prepare working solutions, this stock solution may be diluted in an aqueous solution to the desired final concentration of NAE. Working solutions have been prepared and tested in the range of from about 3.5 mg/L to about 100 mg/L final concentration of NAE. In one such embodiment, a final working concentration of the anti-senescent ingredient on the order of about 12.5 mg/L has shown to be particularly advantageous in the preservation of several floral crops. Additionally, one or more wetting agents may be added to the solutions to improve ease of formulation.

Other NAEs such as those described herein, and particularly NAE's such as NAE14:0, NAE16:0, NAE18:0, NAE18:1, and NAE18:2 have been shown to effectively substitute for NAE12:0 in the formulation shown above, particularly in terms of solubility (in aqueous solutions) and efficacy. These NAEs, however, may be less desirable in certain embodiments due to typically higher manufacturing costs and decreased shelf life. The use of longer acyl chain NAEs such as NAE16:0, NAE18:0 and NAE20:0 in the formulations of the invention may also be less desirable due to their limited solubility in water (e.g., visible turbidity is apparent in some NAEs at concentrations as low as 17.5 mg/L). Nonetheless, formulations containing these NAEs were effective at extending the freshness of cut roses beyond that of water alone, or commercial preservative solutions such as FloraLife®.

The formulations may optionally be prepared in ordinary water, distilled water, deionized water, or reverse osmosis purified water alone, or alternatively, may be prepared as buffered aqueous solutions as described above. For example, formulations of about 10 to 20 mM potassium phosphate in a pH range of from about 6.5 to about 8.0; or alternatively, formulations of about 10 mM to 50 mM $NaHCO_3$, in a pH range of from about 7.0 to about 8.0, have been shown to provide particular advantages in the preservation of many types of floral and foliage cuttings.

Moreover, the inventors have demonstrated the ability of the compounds and compositions of the present invention to be readily added to many of the commercially available flower and ornamental tree formulations. For example, the NAE compositions disclosed herein, such as, for example, NF20-XL, dissolve readily in the commercially available nutritive solutions such as Peters Professional Christmas Tree Preservative (Spectrum Brands, Inc. St. Louis, Mo.), Petalife® (8-hydroxyquinoline citrate), Oasis® (Smither's Oasis, Inc., Kent, Ohio), Rogard® (Gard Environmental Group, Carpentersville, Ill.), Everbloom® (8-hydroxyquinoline citrate), Aquaplus® (Syndicate Sales Inc., Kokomo, Ind.), Spring®, Vita Flora® (Vita Products, Inc., Chandler, Ariz.), and Chrysal Clear® (Pokon & Chrysal-Naarden-Holand, Bussum, The Netherlands) or Floralife® (FloraLife, Inc., Walterboro, N.C.).

The inventors have also tested several different types of powdered and fluidized lecithin products from central soya in various NAE formulations. All were shown not to interfere with effectiveness of the active ingredients, and enzyme-modified and hydroxylated lecithins afforded significant increased solubility of the NAE compounds when alcohol-concentrated stock solutions were diluted into aqueous working solutions when compared to solutions containing unmodified lecithins, or no lecithins at all.

The inventors also contemplate that in certain aspects of the invention it may be advantageous or desirable to optionally prepare the anti-senescent formulations using a combination of two or more active ingredients. In these embodiments, the active ingredients could comprise two or more NAE compounds present in similar, or different concentrations, or alternatively, could comprise one NAE compound in combination with one or more additional anti-senescent or flower-preserving active ingredients. For example, one or more NAE compounds could be added to commercial formulations already demonstrated to possess flower-preserving or flower appearance-extending properties to provide an enhanced or synergistic amount of flower-preserving activity than that afforded by the use of just one such compound alone. Owing to the preparation and manufacture of the many commercially-available formulations of ornamental tree freshness products, and the equally large number of commercially-available formulations of cut flower preserving and enhancing products, the inventors contemplate that significant advantages could be obtained by adding one or more of the NAE compounds disclosed herein to such formulas to provide improved products that significantly prolong the freshness, appearance, and aesthetic qualities of flowers and plant parts contacted with such solutions.

2.4 Preparation of the Compositions of the Invention

The cut flower preservative composition of the present invention can be prepared by simply mixing the components necessary to complete the intended preservative in accordance with conventional mixing technologies. To prepared diluted NAE compositions, water and/or other suitable solvents or diluents may be used in suitable proportions. For example, the NAE compound(s) may be formulated in water or water-soluble organic solvents (for example alcohols, glycols or glycerol) or other suitable carriers or diluents.

Also, in the preservation of freshly cut plants, aqueous gels formed from polymers that are of sufficient strength to support the stem of the plant even in the absence of inert solid aggregates. In addition, the polymers used in the method of the present invention possess sufficient water absorbing and swelling ability such that suitable gels are formed using very low percentages of polymers, therefore allowing a sufficient amount of free, unbound water available for plant uptake upon demand. In addition to clays and natural gums, several types of water-absorbing cross-linked polymers have been used to form aqueous gels that are useful as a plant growth medium or plant preservation medium.

The active compounds of the invention may be formulated in a matter suitable for packaging, or commercial resale. They may be formulated as a ready-to-use liquid or a concentrated form thereof that may be diluted prior to use. Typical stock solutions, or concentrated formulations will comprise from about 1.0% to about 20% of the active ingredient, or alternatively, may include from about 0.1% to about 5.0%. In certain embodiments, the stock solutions may comprise from about 0.05% to about 2% of the active ingredient. Alternatively, the formulations may be prepared as dry powders, granules, slurries, suspensions, or crystals that may be reconstituted with a suitable aqueous solution to provide either concentrated stocks or diluted working stocks.

In the case of ready-to-use formulations, the final concentration of the active compound in the working solutions is contemplated for most applications to be on the order of from about 0.4 to 400 µM, and preferably from about 4.0 to about 200 µM, and still more preferably in the range of from about 40 to about 100 µM.

In the case of stock solutions, or concentrates, the active compound(s) may each be present in a concentration of from about 1.0% to about 100% by weight, preferably from about 5% to about 80% by weight, or alternatively in a concentration of from about 10% to about 50% or so. Of course, depending upon the particular formulation, almost any practical concentration of the anti-senescent ingredient(s) may be present in the concentrated solutions so long as they may be diluted to an active concentration in the final working solution into which the plant parts are placed for storage. Thus, it is altogether possible for the inactive ingredients to be present in stock solutions in amounts of about 100%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 4%, about 3%, about 2%, or about 1% or less.

Such concentrates or stock solutions are preferably diluted in the water in which the cut flowers or plant parts will be stored or kept. Final concentration of active ingredient in the working solutions will necessarily be in the ranges that provide improved preservation, storage, appearance, or integrity of the plant parts stored therein, but the practical solutions contemplated by the inventors will typically include concentrations of the active ingredient on the order of from about 0.1 µM to about 1000 µM, preferably from about 0.4 µM to about 800 µM, more preferably from about 0.8 µM to about 600 µM, and more preferably still, on the order of from about 1.0 µM to about 400 µM, or on the order of from about 2.0 µM to about 200 µM, with all intermediate concentrations also being considered to fall within the scope of the present disclosure. Likewise, in certain instances, the amount of the active ingredient may be significantly lower, such as, on the order of from about 0.001 µM to about 10 µM, or from about 0.01 µM to about 1 µM.

While no particular limitation is imposed on the concentration used of the compound of the general formula (I) because optimal value of the concentration can vary depending on the kind and state of a flower, branch, tree, or plant part to which said compound is to be applied, the optimum range of use of the disclosed compositions will preferably be in the range of from about 0.2 µM to about 800 µM by dissolving or dispersing in a suitable solution. Likewise, the compositions may be added initially only once or twice to the storage solution, or alternatively, may be freshly added to the storage solution each time it is changed.

2.5 Preservation of Cut Flowers and Severed Fruit or Plant Parts

Illustrative examples of flowers for which the disclosed NAE compositions are effective in preserving their freshness and/or appearance include carnations, roses, daisies (including e.g., those of the Gerber variety), delphinium, sweet pea, annuals, perennials (including e.g., baby's breath), lily, freesia, bulb, rhizome, and tuberous plants (including e.g., tulips, daffodils, hyacinths, and callas), orchids, bird-of-paradise, and other tropical and sub-tropical flowering species (including e.g., *Strelitzia, Amaranthus, Anthurium, Protea*, and *Heliconia* spp.).

Illustrative examples of trees and severed plant parts for which the disclosed NAE compositions are effective in preserving their freshness and/or appearance include tree branches, stems, leaves, bracts, ornamental coniferous trees, such as juniper, spruce, fir, cedar, pine, and other types of Christmas trees and the like (including e.g., Frasier fir, Douglas fir, blue spruce, Norfolk Island pine, and Scotch pine, etc.), fruits, shoots, plant cuttings, rooted or bare-root cuttings (such as e.g., rosh bushes and other commercial floral, ornamental, or foliage plants and the like).

The compositions of the present invention may also be used to preserve the shelf life or appearance of fruits, including fruits that have been severed, such as sliced fruits and the like. Illustrative examples of fruits for which the disclosed NAE compositions are effective in preserving their freshness and/or appearance, and/or extending the shelf-life, include peaches, pears, apples, nectarines, plums, bananas, papaya, pineapple, kiwi, figs, melons, grapes, mangoes, ugli fruit, star fruit, citrus and tropical fruits, and the like.

2.6 Preservation of Flowers and Plants Under Cultivation

The compositions of the present invention need not only be applied to fruits, foliage, and flowers after harvest. In fact, the inventors also contemplate that such compositions may be applied to plants of the florist crop while still under cultivation in fields, as well as to plants of the florist crop during or after transplantation to planters or retail pots, and also to flowers, trees and foliage during their actual harvest. Such application of the products during cultivation provide the additional advantage of utilizing the plant's active and passive transport mechanisms to distribute the active ingredients throughout the tissues, fruits, flowers, and stems, of the living plant. This in vivo distribution pre-harvest affords a higher accumulation of the active compound in the plant tissues, than that which may be obtained by soaking or spraying the severed plant parts after harvest. In some embodiments, the inventors contemplate the use of both pre-harvest and post-harvest exposure of the plant material to the active ingredients to maximize the effects of preservation and aesthetic maintenance. In similar fashion, the compositions of the invention may also be used to prolong the blooming, bud formation, blossoming, or fruiting time of a plant, such as a fruit, or a foliage crop or an ornamental tree, that is treated with one or more of the compounds disclosed herein prior to harvest, and then, optionally treated again during transport and/or retail distribution of the plant material.

3.0 BRIEF DESCRIPTION OF THE DRAWINGS

The drawings form part of the present specification and are included to further demonstrate certain aspects of the present invention. The invention may be better understood by reference to one or more of the following drawings in combination with the detailed description of specific embodiments presented herein:

FIG. 1 shows the change in flower diameter for white carnations treated with various solutions and incubated for 17 days at room temperature (25° C.). Solid circles, 0.2 mM NAE12:0; Solid inverted triangles, 0.2 mM lysophosphatidylethanolamine (LPE, purified from egg yolk; Sigma Chemical Co. St. Louis, Mo.); open circles, AquaPlus® (dissolved per manufacturer's instructions); solid squares, Aspirin (325 mg/L); Solid diamonds, Spring®), diluted per manufacturer's instructions). Solid triangles, water only. Values are the averages of two flowers/treatment. Treatments were conducted in "blind."

FIG. 2 shows the change in flower diameter for white carnations treated with various solutions and stored for 17 days in a cold room (6° C.). Flowers were then placed at room temperature (25° C.) and measurements reported for the designated number of days thereafter, beginning with day zero (day removed from cold room). Solid circles, 0.2 mM NAE12:0; Solid inverted triangles, 0.2 mM lysophosphatidylethanolamine (LPE, purified from egg yolk; Sigma Chemical Co. St. Louis, Mo.); Open circles, Crystal Clear® (dissolved per manufacturer's instructions); Open squares, AquaPlus® (dissolved per manufacturer's instructions); Solid squares, aspirin (325 mg/L); Solid diamonds, Spring®, diluted per manufacturer's instructions); Solid triangles, water only. Values are the average of two flowers/treatment. Treatments were conducted in "blind."

4.0 DESCRIPTION OF ILLUSTRATIVE EMBODIMENTS

4.1 N-Acylphosphatidylethanolamine

Figure 1:
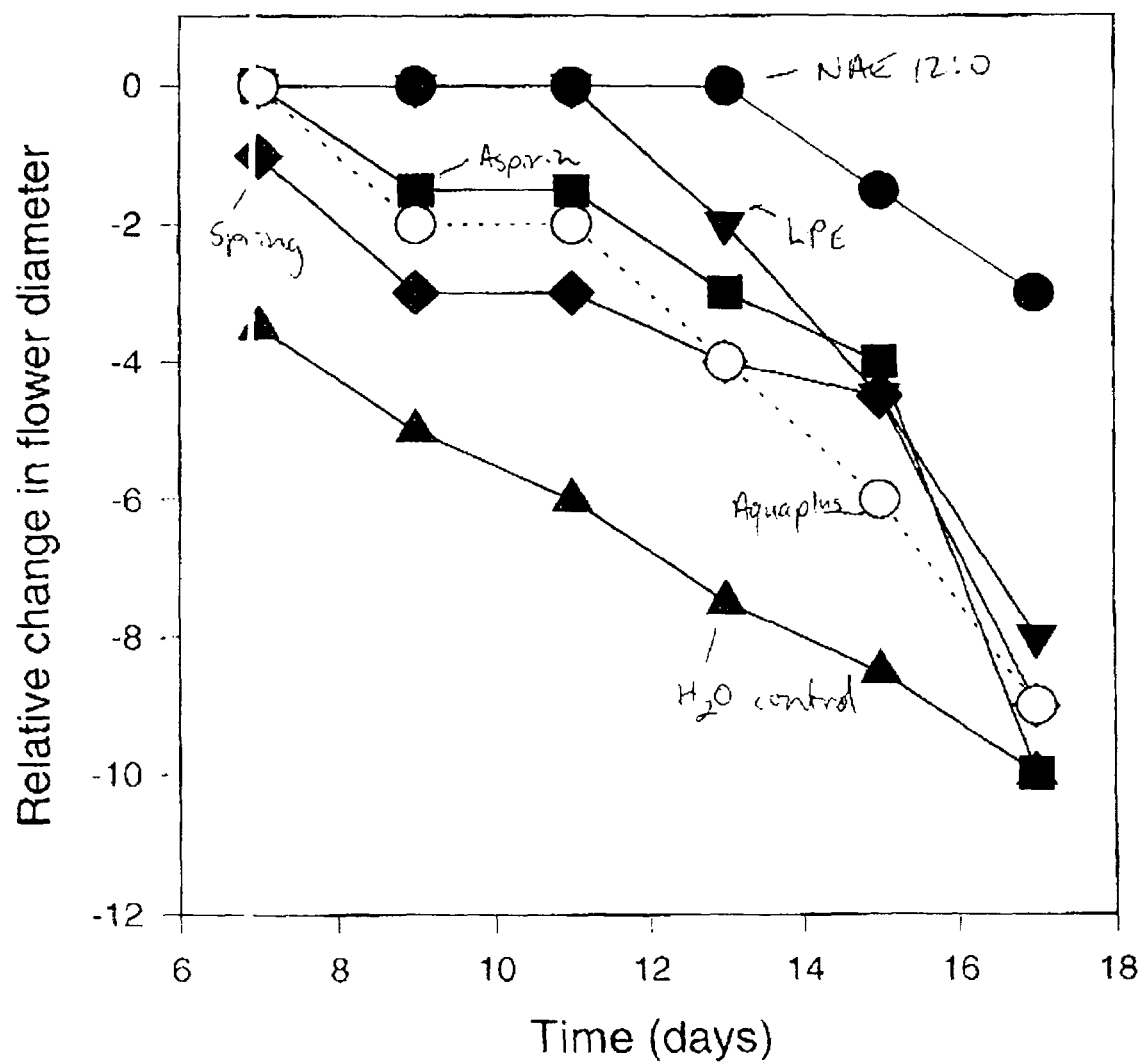

N-acylphosphatidylethanolamine (NAPE), a minor phospholipid, was first discovered in wheat flour (Bomstein, 1965). NAPE appears to be a ubiquitous phospholipid found throughout the animal and plant kingdoms (Schmid, 1990; Chapman and Moore, 1993). NAPE has an unusual structure due to the presence of a third fatty acid moiety linked to the ethanolamine head group. NAPE is synthesized in plants by an enzyme designated NAPE synthase, which catalyzes the transfer of free fatty acids to the primary amino group of phosphatidylethanolamine. This enzyme activity is CoA- and ATFI-independent (Chapman and Moore, 1993), and was recently purified to homogeneity (Cai et al., 1995; McAndrew and Chapman, 1998).

NAPE comprises about 2 mol % of the total phospholipid in plant tissues (Chapman and Sprinkle, 1996: Sandoval et al., 1995). A physiological role for NAPE in plants has yet to be firmly established, but it was postulated to play a role in membrane stabilization under times of stress that result in threats to the integrity of the membrane bilayer (Schmid, 1990). This hypothesis was based upon biophysical studies with NAPE demonstrating that its unusual structural features allowed it to organize into a bilayer and function as a membrane-stabilizing lipid (Akoka et al., 1988; LaFrance et al., 1997). In mammalian systems NAPE accumulated in the membranes of ischemic heart and brain (Natarajan et al., 1986; 1981), but not in surrounding undamaged tissue.

More recently NAPE has been investigated as a precursor molecule for N-arachidonoylethanolamine (ananandamide, a type of NAE), a compound that binds to the cannabinoid receptor in mammalian neurons. Research involving NAE in mammalian systems has progressed rapidly in the last several years with identification of several other functional activities. NAEs are believed to play a role in such processes as a) inhibition of forskolin-mediated cAMP accumulation b) inhibition N-type $Ca^{2+}$ channel activity c) sperm fertilizing capacity through inhibition of the acrosome reaction d) embryo implantation in the uterus (Schmid, 1996).

For plants, the role of NAPE and its catabolic product, NAE, is not known. New evidence has shown a six-fold increase in NAE released into tobacco cell culture medium after treatment with a fungal elicitor, xylanase (Chapman et al., 1998). The increase of NAEs was followed by an increase in the biosynthesis of NAPE by approximately 3-fold (Chapman et al., 1995). Furthermore, a microsomal phospholipase D was identified that catalyzed the conversion of NAPE to NAE, and evidence indicated this activity perhaps was regulated by activated G-proteins (Chapman et al., 1998; DeSouza, 1997).

4.2 Phospholipase D

Phospholipase D (EC 3.1.4.4; PLD) catalyzes the hydrolysis of phospholipids at the terminal phosphodiester bond, resulting in the formation of phosphatidic acid and the free head group. The enzyme was first discovered in plant carrot extracts in 1947 (Hanahan and Chaikoff, 1947) and has since been found in all organisms, making it a ubiquitous enzyme (Munnik et al., 1998). An interesting biochemical property useful in PLD analysis is its ability to catalyze a transphosphatidylation reaction using any primary alcohol, and producing the corresponding phosphatidyl-alcohol (PEOH) instead of phosphatidic acid (Singer et al., 1997; Wang, 1997; Munnik et al., 1998).

Although the enzyme was discovered some 50 years ago, the physiological role is still being elucidated. A significant discovery was made recently in the identification of two additional isoforms in plants. PLD β and γ, which differ markedly from the most prevalent and well-studied form of plant PLD, PLD α. PLD β and γ contain $PIP_2$-binding sites (Qin et al., 1997) and are catalytically active with micromolar concentrations of calcium (Pappan et al., 1997b). These factors lead to the presumption that PLD β and γ are "highly regulated" isoforms.

Various PLDs have been purified from plants, including rice (Lee, 1989; Takano et al., 1987); peanut (Heller et al., 1974); and cabbage (Lambrecht and Ulbrich-Hofmann, 1992). The cloning of a gene encoding PLD in castor bean has been reported (Wang et al., 1994), and Ueki et al. have reported the polypeptide sequence of rice (*Oryza sativa*) and corn (*Zea maize*) PLDs, and the polynucleotide sequences of the genes encoding them (U.S. Pat. No. 5,747,327, specifically incorporated herein by reference in its entirety; Ueki et al., 1995); and Ella et al. and Rose et al. discuss PCPLD isolated and purified from yeast (Ella et al., 1996; Rose et al., 1995).

4.3 Subcellular Localization of PLD

The majority of the studies to date examining subcellular localization involve the PLD α isoform. In discussing the occurrence of PLD within the cell and its physiological role, PLD α is described unless otherwise stated. PLD has been found in both cytosolic and membrane bound fractions. The relative distribution of the two within the fractions depends upon the tissue and developmental stage (Dyer et al., 1994; Ryu and Wang, 1995; 1996; Wang, 1993) as well as the method of tissue homogenization. In young leaves, PLD activity was found mostly in soluble fractions, and immunocytochemical results showed that PLD was compartmentalized into the vacuoles and released upon homogenization of the leaves. This differed from mature leaves, where most of the PLD was associated with the plasma membrane and the endoplasmic reticulum (Xu et al., 1996). Other studies have shown translocation of PLD to the membrane upon wounding (Ryu and Wang, 1996). PLD β and γ activity was associated with membrane fractions, but the precise subcellular distribution of these isoforms has not been established (Pappan et al., 1997a; 1997b).

In mammalian systems, multiple PLD activities exist with a cytosolic form differing from a membrane bound form in substrate specificity, cofactor(s) requirements, and detergent effects. At this time it is unclear whether different PLD isoforms are expressed in the same cells or whether differences represent variant states of the same enzyme (Singer et al., 1997).

4.4 Catalytic Properties

PLD α purified from castor bean endosperm hydrolyzes PC, PE, and PG, but not PI or PS in single class phospholipid vesicles. PLD β and γ were only able to hydrolyze PE and PS in the presence of $PIP_2$. In the presence of $PIP_2$ and PE, PLD β and γ were able to hydrolyze PC, PG, and NAPE (Pappan et al., 1998). One of the most puzzling features of the predominant PLD α form is the requirement for millimolar (20–100) concentrations of calcium for maximal activity in vitro. This is in contrast to PLD β and γ enzyme activities that require micromolar (~50 μM) concentrations of calcium for optimal activity (Pappan et al., 1997a; 1997b) in vitro. The PLD activities in animals also are distinct; the cytosolic PLD can hydrolyze PE, PC, and PI but only in the presence of calcium. The two different mammalian membrane-associated PLDs are also distinguishable by the requirement of a $PIP_2$, for both, but one is stimulated by oleate and the other is stimulated by the small G-protein, ARF (Singer et al., 1997; Munnik et al., 1998).

4.5 Cloning and Expression of PLD

Sequencing of the N-terminus of the castor bean endosperm PLD allowed the first full-length cDNA to be isolated. Since then, PLD cDNAs have been cloned from a number plant species including maize (GenBank Accession No. D73410), rice (Accession No. D73411), black-eyed pea (Accession No. U92656), *Pimpinella brachycarpa* (Accession No. U96438) and *A. thaliana* (GenBank Accession No. U84568 and GenBank Accession No. AF027402) (Dyer et al., 1995; Pappan et al, 1997a; 1997b; Qin et al., 1997; Ueki et al., 1995, Morioka et al., 1997). Three distinct PLD cDNAs were identified from *A. thalania* and designated PLD α, β and γ (Dyer et al., 1995, Pappan et al., 1997a; 1997b).

There is a 73–90% amino acid sequence identity among the PLD α cDNAs from castor bean, rice, maize and *Arabidopsis*. This is in contrast to the *A. thalania* PLD α protein having only 40% identity to the *A. thalania* PLD β and γ, yet, PLD β and γ were reported to have 66% identity to each other at the amino acid sequence level (Pappan and Wang, 1998). It has been reported that PLD β is more closely related to the proteins cloned from yeast and humans than the α form (Wang, 1997). The *A. thalania* PLDα has a molecular mass of 91,800 daltons whereas the *A. thalania* β and γ reported molecular mass is 109,000 and 95,500 daltons, respectively (Pappan and Wang, 1998). Alignments of the plant PLD sequences have revealed three conserved regions. A calcium phospholipid-binding domain (C2) was present in all plant PLDs (but is lacking in all mammalian and yeast PLDs to date) near the N-terminus of the sequence. Second, two putative catalytic HxKxxxD (SEQ ID NO:15) motifs have been identified in all PLDs cloned from plant, animals and yeast. It has been hypothesized that the absolute conservation of His, Lys and Asp residues at these positions suggest these residues are in the active site (Pointing and Kerr, 1996; Sung, 1997). Third, a binding site for $PIP_2$ also was identified surrounding the second HKD motif. This region is rich in basic residues and has been reported to be responsible for polyphosphoinositide binding in proteins such as gelsolin Ph and villin (Divecha and Irvine, 1995).

4.6 Role of PLD in Plants

Historically phospholipase D activity has been associated with large-scale membrane degradation of lipids during germination and senescence (Munnik et al., 1998). However, more recent studies suggest that in addition to membrane degradation, PLD may also have a more highly regulated role involving signal transduction (Munnik et al., 1995; Ryu and Wang, 1996, Nakamura, 1996; Ritchie and Gilroy, 1998). High activity of the PLD enzyme was found in seeds undergoing germination, organs involved in senescence, and tissues susceptible to wounding or interacting with pathogens.

PLD has been suggested to play a role in seed germination. Immunological studies of PLD α showed an increase in protein levels in the endosperm tissue during germination (Wang et al., 1993). In rice, an increase in mRNA levels for PLD α was also reported shortly after inhibition of the seedlings (Ueki et al., 1995). Another study, reported three variant forms of PLD α in soybean, the expression level of these 3 proteins increased during germination (Dyer et al., 1994). More recently, a study conducted in barley reported that PLD activity in the aleurone might be involved in signal transduction events that lead to the triggering of abscisic acid (ABA) response involved in seed germination in barley aluerone (Ritchie and Gilroy, 1998).

PLD-mediated hydrolysis of phospholipids leading to membrane deterioration has been proposed in senescing plants (Pappan and Wang, 1998). PLD involvement in senescence is of particular interest due to the monetary value associated with the spoilage of agricultural crops (Pappan and Wang, 1998). A recent study used PLD α-antisense suppressed *Arabidopsis* plants to investigate the role of PLD α in plant senescence. This study provided direct evidence of PLD α involvement in ABA- and ethylene-promoted senescence in detached leaves. However, detached leaves from wild type and PLD α suppressed plants in the absence of ABA or ethylene were shown to have a similar rate of growth and development, which included the rate of senescence (Fan et al., 1997). Another study examined the regulation of tomato fruit ripening and its relationship to PLD α activity; the researchers drew a similar conclusion as Fan et al., (1997).

Wounding of plants occurs in nature usually when an herbivore feeds on plant tissue. Changes in PLD activity have been described in relation to wounding (Ryu and Wang, 1996). PLD α activity was shown to increase in wounded castor bean leaves. This activity was not due to an increase in protein expression, but rather a translocation of the PLD α from the cytosol to the membranes in both wounded and unwounded cells. A similar translocation pattern of PLD α also was obtained by an increase in free calcium at physiological concentrations in the homogenization buffer (Ryu and Wang, 1996).

Perception of pathogens by a plant leads to a hypersensitive response (HR) cascade which results in membrane damage and cell collapse (Goodman and Novacky, 1994). Rice leaves undergoing interactions with pathogens revealed an increase in PLD α mRNA transcripts, and a change in the distribution of the PLD protein in the membranes. The PLD protein, in resistant interactions, was clustered in plasma membranes at the site of pathogen attack; however, in susceptible interactions the PLD protein was distributed uniformly along the plasma membrane (Nakamura, 1996). This study provided evidence for the role of PLD in defense to pathogen invasion. A recent study suggested the involvement of PLD in elicitor-treated tobacco cells, where NAPE was hydrolyzed to NAE. Evidence showed the accumulation of two NAE species, N-lauroyl- and N-myristoyl-ethanolamine, and a mastoparan-stimulated PLD activity detected in microsomes that hydrolyzed NAPE to NAE. This latest evidence leads to questions involving the role of PLD activity toward NAPE and the physiological significance of the NAE in plant defense responses.

4.7 Biochemical Regulation of PLD

PLD isoforms were expressed in *E. coli* to examine the activity toward NAPE. The ability of PLD β and γ to hydrolyze NAPE marks a key difference from PLD α. PLD δ hydrolysis has not yet been shown (Pappan et al., 1998), but it was tested in these studies using conditions as described for calcium-dependent assays as well as those conditions described for $PIP_2$ dependent assays. Most likely the appropriate environment/activator has yet to be used to activate this isoform of PLD. Activity of the PLD β and γ isoforms was previously demonstrated in membrane fractions (Pappan et al., 1998). In addition, PLD activity toward NAPE was reported in microsomal fractions of tobacco cells (Chapman et al., 1998). This activity may be attributed to that of the PLD β or γ isoforms.

PLD (α, β, or γ) showed hydrolytic activity towards PC, PE and PG, but PS and NAPE only served as substrates to PLD β and γ. The hydrolysis of these five phospholipids by PLD-β and PLD-γ occurred under conditions substantially different than those used for PLD α activity. PLD-β and -γ required $PIP_2$, for activity towards all five of the phospholipids tested. In addition to $PIP_2$, PE was required for hydrolysis of NAPE, PG, and PC by PLD-β and -γ.

Recent studies have established that $PIP_2$, is required for hydrolysis of PC by PLD-β, and -γ (Qin et al., 1997; Pappan et al., 1997b). Isoforms of PLD in mammals and yeast also showed a requirement of $PIP_2$ for PLD activity (Kodaki and Yamashita, 1997; Hammond et al., 1995, Waksman et al., 1996). Recent studies showed plant PLD binding affinity for $PIP_2$, using glutathione-S-transferase fusion protein constructs in which radiolabeled $PIP_2$-bound to GST-PLD β greater than GST-PLD γ (Qin et al., 1997). The requirement for $PIP_2$ for PLD activity also was supported by the identification of putative $PIP_2$ binding domains identified in the amino acid sequences of PLD β and γ (Qin et al., 1997).

The amount of $PIP_2$ needed for optimal activity in plants was around 8 mol %, but was active with as little as 1 mol % when tested in lipid vesicles (Pappan et al., 1997b). The amount of $PIP_2$ estimated is 0.05% of the total phospholipid in plants. Thus, this raises the question if activating levels are present in plant membranes. This question was recently addressed by Pappan and Wang (1998) suggesting the possibility of $PIP_2$ concentration being sufficient due to its asymmetric distribution, with greater amounts occurring on the inner leaflet of the plasma membrane. There is also evidence reported for mammalian cells, that $PIP_2$ is concentrated in the caveolae which are small, plasma membrane invaginations that have been suggested to play a role in cell signaling (Pike and Casey, 1996). Also, PIP was able to activate the PLDs, and perhaps the combination of PIP and $PIP_2$ could influence the activity of the PLD in an in vivo environment (Pappan and Wang, 1998). Another possible way of activation may be through the initial hydrolysis of phospholipids producing PA, which then stimulates the synthesis of $PIP_2$ from PIP by PI-4-phosphate kinase (Qin et al., 1997).

In addition to $PIP_2$, PLD β and γ require lipid vesicles predominately made of PE for the hydrolysis of NAPE. In animals, bovine kidney PLD required PE in mixed vesicles for activity (Nakamura et al., 1996). The requirement of a relatively high concentration of PE (50 mol % or more) for PLD β and γ activities toward NAPE indicates that PE is not acting as a cofactor for PLD β and γ, but rather, it affects the vesicular conformation (Pappan et al., 1998). Mixed phospholipid Vesicles with a substantial amount of PE form inverted hexagonal phases (Lafleur et al., 1990; Cullis et al., 1986). This may mean that PLD β and γ are relatively inactive in a regular bilayer and their substrates are presented in lipidic particles (Pappan et al., 1998). Nonlamellar phases are reported to occur during membrane budding and fusion of two bilayers (Cullis et al., 1986). In addition, mammalian PLD has been proposed to be involved in vesicular trafficking and membrane fusion (Hammond et al., 1995).

The formation of inverted hexagonal phases may not be the only property that activates PLD β and γ. In plant cells, the biological membranes are composed primarily of PC rather than PE, although an asymmetry exists with the majority of PE located on the interior of membrane bilayers. This location of PE on the interior of membranes may be necessary for membrane-protein associations to occur at physiological levels of calcium as indicated by a study which found four cytoplasmic proteins bound in a calcium dependent manner to membranes that contained PE rather than PC (Bazzi et al., 1992).

The requirement of both $PIP_2$, and a high concentration of PE for NAPE hydrolysis by PLD β and γ indicates that the two PLDs are highly regulated by membrane conformation and composition. The ability of only PLD β and β to hydrolyze NAPE in a different membrane lipid environment than that of PLD α may underlie a mechanism that differentially activates the PLDs in the cell.

The concentration of calcium needed for PLD β and γ activity is also substantially different than that of PLD α, PLD β and γ require micromolar concentrations of calcium for maximal activity whereas PLD α requires millimolar concentrations of calcium for activity (Pappan et al., 1997a). Calcium concentration differences may be due to differences within the calcium-phospholipid binding (C2) domain PLD α has a loss or substitution of three of the conserved acidic amino acids in exchange for neutral or positively charged amino acids: hence, this may be imparting a loss of calcium sensitivity (Kopka et al., 1998).

NAE, a naturally occurring lipid, has been identified as a potent inhibitor of plant PLD α. This lipid has been implicated previously in several mechanisms in mammalian tissues including cell signaling as an endogenous ligand for the cannabinoid receptor (Schmid et al., 1996; Beltramo et al., 1997). Most recently, NAE12:0 and 14:0 were found to accumulate in the culture medium of elicitor-treated tobacco cells. In addition, a microsomal phospholipase D activity was discovered that hydrolyzed NAPE to form NAE (Chapman et al., 1998).

Several inhibitors of mammalian phospholipase D have been identified. These inhibitors include fodrin (Lukowski et al., 1996), synaptojanin (Kim et al., 1996), and clathrin assembly protein (Lee et al., 1997) as well as some lipids. An oleate-dependent PLD from rat brain was inhibited by several acidic phospholipids of which $PIP_2$, was the most effective inhibitor (Kanfer et al., 1996). In contrast to this was the $PIP_2$-stimulated PLD, which was inhibited by oleate (Hammond et al., 1995). This unique interaction in which an activator for one PLD isoform is an inhibitor of another gives an example of possible PLD regulation and "crosstalk" between different PLD isozymes. The hydrolysis of NAPE by PLD β and γ to form NAE and its inhibition of PLD α may be yet another form of regulation between the different PLD isozymes.

Other lipid inhibitors of PLD in mammalian systems include ceramide (Venable et al., 1996), alkylphosphate esters (Dittrich et al., 1996) and lysophosphatidyserine (Kawabe et al., 1998). Ceramide, a sphingolipid, was also shown to be an inhibitor of PLD. This inhibition is a result of ceramide interacting with protein kinase C-mediated activation of PLD (Venable et al., 1996). Lysophosphatidylserine is an effective inhibitor of oleate-dependent PLD, ARF-dependent PLD, and $PIP_2$-dependent PLD (Kawabe et al., 1998). The inhibition of plant PLD by lysophosphatidylethanolamine (LPE) recently has been shown to occur. LPE is a lipid-derived senescence retardant of leaves, flowers, and post-harvest fruits (Ryu et al., 1997). NAE inhibition of PLD α is only the second lipid inhibitor of plant PLD alpha. This evidence along with the release of NAE in response to fungal elicitor provides increasing evidence that NAE may function as a signal molecule in plants.

NAEs with different acyl chains were examined for their relative effectiveness on PLD α activity. NAE12:0 and NAE14:0 showed the most effective inhibition of plant PLD α. This contrasts with other studies where acyl chain length was examined as a factor affecting the inhibition of PLD. Lysophosphatidylethanolamine (Ryu et al., 1997) and akylphosphate esters (Dittrich et al., 1996) both were shown to increase inhibition of PLD with increasing chain length. Lysophosphatidylethanolamine 18:1 was the most potent inhibitor of both castor bean and cabbage PLD α. The ability of LPE 18:1 to effectively inhibit PLD was in a concentration range of 40 μM to 200 μM (Ryu et al., 1997). Lysophosphatidylserine inhibition of mammalian PLD ranged from 1 μM to 10 μM (Kawabe et al., 1998). The results described here show potent inhibition of PLD α activity from 0.1 μM to 1.0 μM for NAE12:0 and NAE14:0. These results are significant for two reasons. First, the molecular species that is the most potent inhibitor is also the molecular species that is released from tobacco cells upon treatment with fungal elicitor. Second, the low concentrations needed for inhibition of plant PLD alpha makes it plausible to consider NAE as a possible lipid mediator in vivo.

Inhibition of castor bean PLDα by NAE14:0 is believed to be through noncompetitive binding based on enzyme-kinetic analysis. Noncompetitive inhibition of PLD α by LPE was also reported (Ryu et al., 1997). The apparent Km determined during these studies was comparable to other published apparent $K_m$ values for castor bean and cabbage PLD α. The apparent $V_{max}$ in the absence of inhibitor is also comparable to other published apparent $V_{max}$ values (Ryu et al., 1997; Wang et al., 1993). In addition to examining the type of inhibition PLD by NAE14:0, an apparent $K_m$ was calculated.

The apparent $K_m$ for NAE14:0 was 0.02 μM, which is consistent with the $IC_{50}$ value of 0.03 μM. This is in contrast to the $IC_{50}$ value for castor bean PLD α of 0.1 μM for NAE14:0. The discrepancy in the values could be due to the presence of interfering compounds in the E. coli lysate (not present in the purified cabbage PLD preparation), which may bind to NAE making it inaccessible to the PLD.

The mechanism of PLD α inhibition by NAE is not fully understood. NAE may be interacting directly with the enzyme to change its native conformation and decrease its activity. Another explanation is the possibility of NAE interacting with the lipid environment to influence the presentation or accessibility of substrate. Since NAE readily incorporates into the lipid surface, the possibility of diluting the effective concentration of the substrate must also be considered (Carmen et al., 1995). This is most readily ruled out as a contributing factor due to the extremely high ratio of substrate to inhibitor concentration.

4.8 Molecular Heterogeneity of PLD

The isolation of a tobacco cDNA fragment, which contains an ORF amino acid sequence highly homologous to a portion of the PLD β from *A. thalania* is described in the following examples. The tobacco cDNA fragment has 74%, 65% and 52% identity to *A. thalania* PLD β, *A. thalania* PLD γ, and tobacco PLD α, respectively. The DNA sequence of this gene gragment is shown in SEQ ID NO: 1, while the polypeptide sequence is shown in SEQ ID NO:2.

Phospholipase D sequences from maize, rice, castor bean, tobacco, black-eyed pea and rape seed all share a high degree of homology to the *A. thalania* PLD α *A. thalania* PLD α and castor bean PLD are 80% identical, and the PLD α amino acid sequences of monocotyledons are approximately 90% identical. In contrast the *A. thalania* PLD β and γ sequences only share 45–50% identity to PLD α (Wang, 1997). Phylogenetic analyses indicate PLD β and γ are evolutionarily divergent from PLD α and PLD β and γ are more closely related to the proteins cloned from yeast and human than to PLD α (Pappan et al., 1997b). The *A. thalania* PLD β and γ, along with human and yeast PLDs, have basic pI values ranging from 7.6–9.3. $PIP_2$ is not only a requirement for PLD β and γ activation, but also for activation of isoforms of PLD in humans and yeast. The isoelectric points for the PLD α forms in plants are acidic with a range of 5–6.

Comparison of the isoelectric points and catalytic properties of the PLDs support the phylogenetic groupings. In addition to these differences, it was demonstrated by Southern blotting analysis that *A. thalania* PLD α, β and γ were encoded by distinct genes (Pappan et al., 1997a). The isolation of a putative tobacco PLD β fragment aids in establishing the presence of phospholipase D β in plants.

4.9 Phospholipase D Polypeptide and Polynucleotide Compositions

A further aspect of the present invention concerns a novel amino acid sequence comprising a phospholipase D (PLD) polypeptide, and the corresponding polynucleotide sequence that encode the enzyme. Also disclosed are methods of identifying PLD-specific polypeptide and polynucleotide compositions, methods for preparing recombinant host cells, vectors, virus, and expression constructs, and methods for making transgenic plants that over-express PLD-specific genes. The invention provides an isolated polynucleotide that: (a) encodes a polypeptide having PLD activity and that comprises an at least 11 contiguous amino acid sequence from SEQ ID NO:2; (b) encodes a polypeptide having PLD activity and at least about 75% sequence identity with the amino acid sequence of SEQ ID NO:2; (c) comprises an at least 15 contiguous nucleotide sequence from SEQ ID NO:1; or (d) hybridizes to the sequence of SEQ ID NO:1, or that hybridizes to the complement thereof, under stringent hybridization conditions.

Preferably the isolated polynucleotide comprises a sequence region that encodes a polypeptide having an at least 11, at least 12, at least 13, at least 14, at least 15, at least 16, at least 17, at least 18, at least 19, at least 20, or at least 21 contiguous amino acid sequence from SEQ ID NO:2, although longer contiguous sequences such as at least 22, at least 23, at least 24, at least 25, or at least 26 or more contiguous amino acid sequence from SEQ ID NO:2 are also contemplated to be particularly preferred. In illustrative embodiments, the isolated polynucleotide comprises a sequence region that encodes a polypeptide comprising the sequence of SEQ ID NO:2.

The isolated polynucleotides of the invention preferably comprise a sequence region that encodes a polypeptide having PLD activity and at least about 75%, 78%, 82%, or 85% or greater sequence identity with the amino acid sequence of SEQ ID NO:2. More preferably, the polypeptides have at least about 90%, about 95%, about 98% or about 99% sequence identity or greater with the amino acid sequence disclosed in SEQ ID NO:2.

Preferred polynucleotides of the present invention typically will comprise an at least 15 contiguous nucleotide sequence from SEQ ID NO:1, although longer contiguous nucleotide sequences from SEQ ID NO:1, such as about 16, about 17, about 18, about 19, about 20, about 21, about 22, about 23, about 24, about 25, about 26, about 27, about 28, about 29, about 30, about 35, about 40, about 45, about 50, about 55, about 60 or more contiguous nucleotide sequence from SEQ ID NO:1, are also highly preferred. In fact, the PLD-encoding polynucleotides may comprise all or substantially all of the nucleotide sequence of SEQ ID NO:1.

Preferred polynucleotide compositions of the present invention typically will comprise a sequence region that hybridizes to the sequence of SEQ ID NO:1, under stringent hybridization conditions. Such stringent hybridizations are well known to those of skill in the art, as are the methods for obtaining and identifying polynucleotides that hybridize to a selected target sequence. For example, as described hereinbelow, stringent hybridization conditions comprising a salt concentration of from about 0.02 M to about 0.15 M, and a temperature of from about 50° C. to about 75° C. are particularly preferred.

A further embodiment of the present invention concerns an isolated polynucleotide that comprises: (a) a sequence region that consists of at least 15 contiguous nucleotides that have the same sequence as, or are complementary to, at least 15 contiguous nucleotides of SEQ ID NO: 1; or (b) a sequence region of from 15 to about 10000 nucleotides in length that hybridizes to the nucleic acid segment of SEQ ID NO:1; or the complement thereof, under hybridization conditions comprising a salt concentration of from about 0.02 M to about 0.15 M, and a temperature of about 50° C., 55° C., 60° C., 65° C., 70° C., or about 75° C. Such polynucleotides may range in size from on the order of about 100 to about 11,000 nucleotides in length, with intermediate ranges such as from about 1000 to about 9,000 nucleotides in length, or from about 2000 to about 7,000 nucleotides in length, or from about 4000 to about 6000 nucleotides in length being particular preferred.

Preferred polynucleotide compositions will typically comprise an RNA, a PNA, or a DNA segment, as described hereinbelow. Such compositions may be comprised within a recombinant vector such as a plasmid, cosmid, phage, phagemid, baculovirus, bacterial artificial chromosome, or yeast artificial chromosome vector. Likewise, the disclosed polynucleotides may be comprised within a recombinant virus or virion. It may be operably linked to a promoter, and particularly to a heterologous promoter such as a plant-expressible constitutive, inducible, or tissue-specific promoter. Exemplary plant-expressible promoters include such well known promoters as corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, Potato patatin, lectin, CaMV 35S, ALS, ubiquitin, globulin 1, cruciferin, napin, β-conglycinin, phaseolin, γ zein, or the S-E9 small subunit RuBP carboxylase promoter.

Such polynucleotides may be used, for example, in preparing a recombinant vector, a transgenic plant, or a recombinant polypeptide composition. Such polynucleotide compositions may also be used as a probe for screening a plant nucleic acid library to identify a gene encoding a polypeptide having PLD activity. Alternatively, their sequence information may be used in the preparation of a target sequence probe to employ a computer-based algorithm to search a computerized database of sequences such as genomic, or expressed sequence tags, cDNAs, and the like to identify a gene encoding a polypeptide having PLD activity. The recombinant vectors of the present invention may also be used in producing a transformed plant cell or plant tissue, a pluripotent plant cell, or a transgenic plant that expresses a polypeptide having PLD activity.

In a related embodiment, the invention provides a host cell that comprises such a recombinant vector that has at least a first heterologous expression unit comprising a PLD-encoding polynucleotide. Such a host cell may be a bacterial cell such as an *Escherichia, Salmonella* or *Agrobacterium* cell, or alternatively, may be an eukaryotic cell, such as a plant cell. Alternatively, the polynucleotide may be comprised within a virus, virion, or viral vector.

The invention also provides an isolated polypeptide encoded by the disclosed PLD polynucleotides. Such polypeptides preferably comprise an at least 11, 12, 13, 14, 15, 16 17, 18, 19, 20, 21, 22, 23, or 24 or more contiguous amino acid sequence from SEQ ID NO:2, and preferably share at least about 70%, about 75%, about 80%, about 85%, about 90%, about 95%, or about 99% or higher sequence identity with the amino acid sequence of SEQ ID NO:2, which encodes a tobacco PLD polypeptide.

Such polypeptides may be used in the preparation of an antibody that specifically binds to a PLD polypeptide comprising the amino acid sequence of SEQ ID NO:2, using the immunological methods described hereinbelow. The PLD-specific antibody compositions so produced that specifically binds to the disclosed PLD polypeptide also represent an important embodiment of the present invention. Such antibodies may be suitably packaged in an immunodetection kit, along with an immunodetection reagent, and instructions for using the antibody in methods such as ELISAs and other immunoaffinity methodologies to detect the presence of PLD polypeptides in a target sample, such as in a plant or leaf extract.

The invention also provides nucleic acid detection kits that typically comprise in suitable container means, at least a first isolated nucleic acid segment comprising a PLD-encoding polynucleotide, a detection reagent, and instructions for using the PLD-specific nucleic acid segment to detect other PLD sequences or to use as probes or primers for related and DNA sequencing methodologies and the like.

Compositions are also provided by the invention that comprise: (a) a PLD-specific polynucleotide, (b) a PLD polypeptide, (c) a PLD-specific antibody, and (d) a recombinant vector, virus, or host cell that expresses a PLD polynucleotide or polypeptide.

The invention further provides a transgenic plant that comprises: (a) a heterologous nucleic acid segment that comprises a PLD polynucleotide; (b) a transformed host cell that expresses a PLD polypeptide; (c) a recombinant virus that expresses a PLD polypeptide; or (d) a recombinant vector that encodes a PLD polypeptide.

Alternatively, the invention further provides transgenic "knock-out" plants and plant cells that lack PLD activity. These cells typically comprise: (a) a heterologous nucleic acid segment that comprises a PLD polynucleotide that has been mutated, or deleted such that the PLD polynucleotide does not encode a functional PLD polypeptide. Such genetic "knock-out" constructs may be constructed so that the defective PLD sequence is introduced into the genome of the cell so that it replaces the wild-type functional PLD gene with the defective mutated gene. Thus transgenic plants and progeny may be produced that lack the ability to produce a PLD enzyme. These plants may be cultivated under conditions to permit their growth in the absence of this activity, such as, for example, by exogenously providing the cell with the product of the reaction normally catalyzed by the PLD enzyme.

The transgenic plant preferably has stably incorporated into its genome a heterologous nucleic acid segment that comprises a PLD polynucleotide (whether encoding a functional or a defective PLD enzyme), wherein the polynucleotide is operably linked to a promoter that expresses the polynucleotide in the cells and tissues of the transgenic plant. Such transgenic plants are preferably monocotyledonous or dicotyledonous plants, such as grains, trees, legumes, fibers, vegetables, fruits, berries, nuts, citrus, grasses, cacti, succulents, flowers, or other ornamental plants.

Exemplary plants include, but are not limited to, corn, rice, millet, tobacco, alfalfa, soybean, bean, sorghum, pea, *Brassica*, safflower, potato, coconut, palm, pumpkin, squash, poppy, sesame, peanut, cocoa, coffee, tomato, flax, sugar beets, canola, sunflower, cotton, kapok, wheat, oat, barley, walnut, pecan, almond, and rye.

The invention further discloses and claims progeny of any generation of such transgenic plant, as well as the seed of any generation of such transgenic plants, and seed of any generation, offspring, or subsequent progeny of such transgenic plants. Particularly encompassed by the invention are seeds, nuts, legumes, and the like, that have an increased level of lipid, relative to untransformed plants of the same species that do not contain one or more exogenously provided PLD-encoding transgenes. Such seeds are particularly preferred for animal foodstuffs, as well as those having increased protein and nutrition content suitable for human consumption.

The invention also provides hereinbelow methods for detecting a PLD-encoding polynucleotide in a sample. Such a method typically involves the steps of: (a) contacting a population of polynucleotides suspected of encoding a PLD polypeptide with at least a first labeled PLD polynucleotide, under conditions effective to allow hybridization of substantially complementary nucleic acids; and (b) detecting the hybridized complementary nucleic acids so formed.

A method is also provided for detecting a PLD polypeptide in a biological sample. This method typically involves contacting a biological sample suspected of containing a PLD polypeptide with a labeled PLD-specific antibody, under conditions effective to allow the formation of immune complexes, and detecting the immune complexes so formed.

A method is also provided for increasing the amount of a PLD polypeptide in a plant cell. This method typically involves expressing in such a plant cell a biologically effective amount of a PLD-specific polynucleotide. The term "biologically effective amount" will be understood by the skilled artisan to mean an amount of the polynucleotide composition that is effective to produce the desired phenotypic trait in the resulting transformed plant cell, i.e. an increased level or amount of PLD polypeptide or PLD enzymatic activity in the cell when compared to a similar untransformed or "wild-type" plant cell.

4.10 PLD Polypeptide Compositions

In one embodiment, the invention provides polypeptides, peptides and proteins that comprise all, substantially all, or portions of a plant PLD enzyme. Highly preferred PLD polypeptides are those that comprise an at least about 15, an at least about 16, an at least about 17, an at least about 18, an at least about 19, or an at least about 20 or more contiguous amino acid sequence from SEQ ID NO:2, and that have PLD enzymatic activity when expressed in a suitable plant host cell cultured under the appropriate conditions for such enzymatic activity. Likewise, PLD polypeptides that comprise an at least about 22, 23, 24, 25, 26, 27, 28, 29, 30, 31, 32, 33, 34, 35, 36 or more contiguous amino acid sequence from SEQ ID NO:2, and that have PLD enzymatic activity when expressed in a suitable plant host cell are also contemplated to be particularly useful in the methods disclosed herein.

In certain circumstances, it may be desirable to employ PLD polypeptides that are even more homologous to the sequence of SEQ ID NO:2. In those embodiments, the PLD polypeptides of the invention will preferably comprise a primary amino acid sequence that comprises an at least about 37, and at least about 38, an at least about 39, an at least about 40, an at least about 43, an at least about 46, an at least about 49, an at least about 51, an at least about 54, or an at least about 57 or so contiguous amino acid sequence from SEQ ID NO:2. Likewise, in other embodiments, it may be desirable to employ PLD polypeptides that are even more homologous to the sequence disclosed in SEQ ID NO:2. In those embodiments, the PLD polypeptides of the invention will preferably comprise a primary amino acid sequence that comprises an at least about 60, an at least about 65, an at least about 70, an at least about 75, or an at least about 80 or so contiguous amino acid sequence selected from SEQ ID NO:2. In fact, when more highly homologous PLD polypeptides are contemplated, those having an at least about 85, and at least about 90, an at least about 95, an at least about 100, an at least about 110, an at least about 120, an at least about 125, an at least about 130, an at least about 135, an at least about 140, an at least about 145, or an at least about 150, or so contiguous amino acid sequence selected from the sequence of SEQ ID NO:2 will be particularly preferred.

Shorter peptide and polypeptide sequences comprised with one or more of the disclosed PLD polypeptides are also within the scope of the present invention. Such peptides may be utilized as described herein in the preparation of epitopes, or used as antigens for the generation of PLD-specific antibodies, or may even be used to screen antibody samples for species that specifically bind to a PLD peptide motif. Such smaller peptides include, but are not limited to sequences that comprise at least 15 contiguous amino acids as set forth in SEQ ID NO:2. These peptides are particularly useful as probes for identifying polypeptides of the PLD family that share conserved regions.

4.11 PLD Polynucleotide Compositions

In a further embodiment, the invention concerns polynucleotides that encode the PLD polypeptides of the present invention. For polynucleotides encoding PLD polypeptides, such sequences preferably comprise from at least about 11, to at least about 1500 or more contiguous nucleotides from SEQ ID NO:1. As such, polynucleotides that comprise at least about 20 to about 1200 or more contiguous nucleotides from SEQ ID NO:1 are contemplated to be particularly preferred in the methods of the present invention. Similarly, polynucleotides that comprise at least about 30 to about 1000 or more contiguous nucleotides from SEQ ID NO:1 are also contemplated to be particularly preferred in the methods of the present invention, as are those polynucleotides that comprise at least about 40 to about 800 or more contiguous nucleotides from SEQ ID NO:1, and those polynucleotides that comprise at least about 50 to about 600 or more contiguous nucleotides from SEQ ID NO:1.

Naturally, all intermediate contiguous sequences are contemplated to fall within the scope of the present invention. For example, polynucleotides that comprise at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80, at least about 85, at least about 90, at least about 95, or at least about 100 or more contiguous nucleotides from SEQ ID NO:1 are contemplated to be particularly preferred in the methods of the present invention, and are contemplated to be particularly preferred polynucleotide compositions.

Likewise, PLD-encoding polynucleotides that comprise at least about 110, at least about 120, at least about 130, at least about 140, at least about 150, at least about 160, at least about 170, at least about 180, at least about 190, or at least about 200 or more contiguous nucleotides from SEQ ID NO:1 are contemplated to be particularly preferred polynucleotide compositions. PLD-specific polynucleotides that comprise at least about 250, at least about 300, at least about 350, at least about 400, at least about 450, at least about 500, at least about 550, at least about 600, or more contiguous nucleotides from SEQ ID NO:1 are contemplated to be highly preferred polynucleotide compositions.

When it is desirable to employ PLD-encoding polynucleotides that are significantly more homologous to the polynucleotide sequences disclosed herein, polynucleotide compositions may be selected that encode PLD-derived peptides that comprise at least about 650, at least about 700, at least about 750, at least about 800, at least about 850, at least about 900, at least about 950, at least about 1000, at least about 1050, at least about 1100 or more contiguous nucleotides from SEQ ID NO:1, and even those up to and including the full-length DNA sequence disclosed in SEQ ID NO:1 are contemplated to be particularly preferred polynucleotide compositions.

Likewise, the PLD polynucleotide compositions of the present invention also encompass those nucleic acid segments that encode a polypeptide having PLD activity, and that comprise a nucleic acid sequence of at least about 12 or 13 or more contiguous amino acids from SEQ ID NO:2. In more preferred embodiments, the PLD polypeptides of the present invention comprise an at least about 14 or 15 or 16 or more contiguous amino acid sequence from SEQ ID NO:2. When it is desirable to identify PLD polypeptides that are still more homologous to SEQ ID NO:2, one may wish to utilize PLD polypeptides that comprise an at least about 17, about 18, about 19, or about 20 or more contiguous amino acid sequence from SEQ ID NO:2.

4.12 Compositions for Gene Detection, Amplification, and Sequencing

In related embodiments, the invention provides methods and compositions for detecting homologous PLD-encoding polynucleotides and homologous PLD polypeptides.

For detection and sequencing of polynucleotides, it is often desirable to isolate smaller polynucleotides for use as hybridization probes, synthesis or sequencing primers, and the like as described in detail herein. In such embodiments, shorter polynucleotide sequences are particularly desirable, including those that comprise a sequence of at least about 20 or 30 or 40 or 50 or so contiguous nucleotides from one or more of the DNA sequences disclosed in SEQ ID NO:1. These sequences find particular utility as probes for screening clone banks, colony blots, or as computer homology search strings for identifying homologous polynucleotide sequences via computer-based algorithm homology searches. This is particularly important when it is desirable to screen a database of cDNA sequences, expressed sequence tags (ESTs) or genomic or chromosomal sequence databases.

For example, polynucleotides that comprise at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, or even at least about 60 or so nucleotides from one of the disclosed sequences are particularly suited for these embodiments.

4.13 Identification of Homologous PLD Polypeptides and Polynucleotides

In addition to the particular illustrative polypeptide and polynucleotide sequences disclosed herein, those having benefit of the present teaching are now also able to identify and characterize a wide variety of PLD homologs and/or isozymes, as well as to identify, characterize, and sequence a variety of PLD-encoding polynucleotides from a variety of plant species. In fact, the inventors contemplate that any plant-derived PLD protein or peptide can be identified using the methods disclosed herein and may be obtained by using the immunological methods disclosed herein to obtain PLD proteins and peptides from a variety of disparate species. Alternatively, the inventors contemplate that those of skill in the art having the benefit of the teachings disclosed herein will be able to identify PLD-encoding polynucleotides either by comparison of one or more of the disclosed sequences to computer databases of plant EST sequences, and identification of highly homologous sequences, or alternatively, by traditional hybridization screening methods employing one or more labeled PLD-specific polynucleotide sequences to screen a population of target nucleic acids, such as e.g., a cDNA or other such genetic library, a colony or clone bank, or by screening individual isolates from particular plant species. In particular, the inventors contemplate the identification of PLD variants, homologs, and related sequences using one or more of the methods disclosed herein to identify a family of PLD sequences. Likewise, one of skill in the art will even be able to utilize the teachings of the present disclosure to identify other PLD-like polypeptides and polynucleotides, including those from related and from distantly-related plant species and to use these sequences in the preparation of transgenic plants having altered PLD-dependent biosynthesis.

By hybridization, immunological, and computer-based homology algorithms, the inventors further contemplate the identification and characterization of PLD-specific compositions from species that are not yet even described or characterized as possessing PLD activity.

In addition to the particular partial PLD polypeptide sequence disclosed in SEQ ID NO:2, the inventors also contemplate the preparation and use of substantially full-length sequences in certain embodiments. As such, polypeptides may be obtained that comprise from at least about 80% or so, and up to and including those having at least about 99% of the PLD primary amino acid sequence as disclosed herein, and yet still possess significant PLD enzymatic activity in vitro and in vivo. In fact, "truncated" polypeptides or "near-full-length" or "substantially full-length" polypeptides are well known in the plant molecular biological arts to often possess all, or almost all of the enzymatic activity that the full-length polypeptide possesses. In many embodiments, these slightly shorter polypeptide sequences may be desirable for use in many of the disclosed methods. This is particularly true, when the creation of "chimeric" polypeptides is desired, as well as in the creation of hybrid polypeptides that have, for example, the addition of a particular amino acid sequence to "target" the localization of the polypeptide to a particular cellular location, or to a particular region of the plant in which the polypeptide is expressed. For example, the preparation of a fusion protein that possesses both PLD activity, yet further comprises a sequence region that targets the peptide to a particular cellular region, such as the membrane, or to a particular organelle, etc. is often desirable. As such, truncated or fusion proteins that comprise only about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% of the primary amino acid sequence as disclosed in SEQ ID NO:2 are particularly embodied by the present invention.

It is well known in the plant molecular biological arts that two polypeptides from different species may differ slightly, or even sometimes, substantially in their primary amino acid sequence, and yet, still possess the same biological activity. As such, homologous or "cognate" PLD polypeptides may be designed synthetically, site-specifically modified, or isolated from different biological sources, that possess similar PLD enzymatic activity, but yet share less than 100% identity at the primary amino acid level with one of the PLD sequences disclosed herein. In fact, such PLD homologous polypeptides may share approximately 60% or 65% sequence identity with one or more of the disclosed sequences herein. More homologous PLD sequences will include those polypeptides that are from about 70% to about 80% identical to either of the polypeptides of SEQ ID NO:2. Still more homologous PLD sequences will include those polypeptides that share from about 85% to about 95% sequence identity with one or more of the polypeptides disclosed in SEQ ID NO:2.

When highly homologous polypeptide are identified that possess PLD enzymatic activity, such as is often the case when polypeptides are obtained from closely-related species, cultivars, or hybrids, the PLD polypeptides identified may share about 96%, about 97%, about 98%, or even about 99% or more sequence identity with one or more of the sequences disclosed in SEQ ID NO:2. Naturally, all intermediate % identity values are contemplated to fall within the scope of the present disclosure. As such, polypeptides having about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, and those having about 98% primary amino acid sequence identity to the sequences disclosed in SEQ ID NO:2 are contemplated to be useful in the formulation of the methods and compositions of the present invention.

In preferred embodiments, the PLD polypeptides of the present invention comprise an at least about 7 or 8 contiguous amino acid sequence from SEQ ID NO:2. Likewise, the PLD compositions of the present invention also encompass those polypeptides that have PLD activity, and that comprise an amino acid sequence of at least about 12 or 13 contiguous amino acids from SEQ ID NO:2. In more preferred embodiments, the PLD polypeptides of the present invention comprise an at least about 14 or 15 contiguous amino acid sequence from one of these full-length sequences. When it is desirable to identify PLD polypeptides that are still more homologous to the disclosed sequences, one may wish to utilize PLD polypeptides that comprise an at least about 16 or 17 or 18 or 19 contiguous amino acid sequence from SEQ ID NO:2.

Highly preferred PLD polypeptides are those that comprise an at least about 20 or 21 or 22 or 23 contiguous amino acid sequence from SEQ ID NO:2, and that have PLD enzymatic activity when expressed in a suitable plant host cell cultured under the appropriate conditions for PLD expression and enzymatic activity. Likewise, PLD polypeptides that comprise an at least about 24 or 25 or 26 or 27 contiguous amino acid sequence from SEQ ID NO:2, and that have PLD enzymatic activity when expressed in a suitable plant host cell are also contemplated to be particularly useful in the methods disclosed herein.

In certain circumstances, it may be desirable to employ PLD polypeptides that are even more homologous to the sequences disclosed in SEQ ID NO:2. In those embodiments, the PLD polypeptides of the invention will preferably comprise a primary amino acid sequence that comprises an at least about 28, and at least about 30, an at least about 35, an at least about 40, an at least about 45, or an at least about 50 or so contiguous amino acid sequence selected from SEQ ID NO:2. Likewise, in other embodiments, it may be desirable to employ PLD polypeptides that are even more homologous to the sequence disclosed in SEQ ID NO:2. In those embodiments, the PLD polypeptides of the invention will preferably comprise a primary amino acid sequence that comprises an at least about 55, and at least about 60, an at least about 65, an at least about 70, an at least about 75, or an at least about 80 or so contiguous amino acid sequence selected from SEQ ID NO:2. In fact, when more highly homologous PLD polypeptides are contemplated, those having an at least about 85, and at least about 90, an at least about 95, an at least about 100, an at least about 110, an at least about 120, an at least about 130, an at least about 140, an at least about 150, an at least about 160, an at least about 170, an at least about 180, an at least about 190, an at least about 200, an at least about 210, an at least about 220, or more contiguous amino acid sequence selected from SEQ ID NO:2 will be particularly preferred.

4.14 Recombinant Vectors

Another important embodiment of the invention is a recombinant vector that comprises a nucleic acid segment encoding one or more of the novel PLD polypeptides disclosed herein. Such a vector may be transferred to and replicated in a prokaryotic or eukaryotic host, with bacterial cells being particularly preferred as prokaryotic hosts, and plant cells being particularly preferred as eukaryotic hosts. In preferred embodiments, the recombinant vector comprises a nucleic acid segment encoding the amino acid sequence of SEQ ID NO:2. Highly preferred nucleic acid segments are those which comprise an at least 15 or 20 or so basepair contiguous sequence from SEQ ID NO:1.

Another important embodiment of the invention is a transformed host cell that expresses one or more of these recombinant vectors. The host cell may be either prokaryotic or eukaryotic, and particularly preferred host cells are those that express the nucleic acid segment(s) comprising the recombinant vector that encodes one or more PLD polypeptides. Bacterial cells are particularly preferred as prokaryotic hosts, and plant cells are particularly preferred as eukaryotic hosts.

In some embodiments, and particularly those involving preparation of recombinant vectors, transformation of suitable host cells, and preparation of transgenic plant cell, longer nucleic acid segments are preferred, particularly those that include the entire coding region of a PLD-encoding gene. As such, the preferred segments may include those that are up to about 20,000 or so nucleotides in length, or alternatively, shorter sequences such as those about 19,000, about 18,000, about 17,000, about 16,000, about 15,000, about 14,000, about 13,000, about 12,000, 11,000, about 10,000, about 9,000, about 8,000, about 7,000, about 6,000, about 5,000, about 4,500, about 4,000, about 3,500, about 3,000, about 2,500, about 2,000, about 1,500, about 1,000, about 500, or about 200 or so base pairs in length. Of course, these numbers are not intended to be exclusionary of all possible intermediate lengths in the range of from about 20,000 to about 15 nucleotides, as all of these intermediate lengths are also contemplated to be useful, and fall within the scope of the present invention.

It will be readily understood that "intermediate lengths", in these contexts, means any length between the quoted ranges, such as 14, 15, 16, 17, 18, 19, 20, etc.; 21, 22, 23, 24, 25, 26, 27, 28, 29, etc.; 30, 31, 32, 33, 34, 35, 36 . . . etc.; 40, 41, 42, 43, 44 . . . etc., 50, 51, 52, 53 . . . etc.; 60, 61, 62, 63 . . . etc., 70, 80, 90, 100, 110, 120, 130 . . . etc.; 200, 210, 220, 230, 240, 250 . . . etc.; including all integers in the entire range from about 14 to about 10,000, including those integers in the ranges 200–500; 500–1,000; 1,000–2,000; 2,000–3,000; 3,000–5,000 and the like.

In a preferred embodiment, the nucleic acid segments comprise a sequence of from about 1800 to about 18,000 base pair in length, and comprise one or more genes that encode a PLD polypeptide as disclosed in SEQ ID NO:2, and particularly the polynucleotide sequence disclosed in SEQ ID NO:1.

It will also be understood that this invention is not limited to the particular nucleic acid sequences which encode peptides of the present invention, or which encode the amino acid sequence of SEQ ID NO:2, including the DNA sequences which are particularly disclosed in SEQ ID NO:1. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full-length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

4.15 Transformed Host Cells and Transgenic Plants

In one embodiment, the invention provides a transgenic plant having incorporated into its genome a transgene that encodes a PLD polypeptide that comprises an at least 15 contiguous amino acid sequence from SEQ ID NO:2. A further aspect of the invention is a transgenic plant having incorporated into its genome a transgene, that comprises an at least 21 basepair contiguous nucleic acid sequence from SEQ ID NO:1. Also disclosed and claimed are progeny of such a transgenic plant, as well as its seed, progeny from such seeds, and seeds arising from the second and subsequent generation plants derived from such a transgenic plant.

In yet another aspect, the present invention provides methods for producing a transgenic plant that expresses a nucleic acid segment encoding the novel PLD proteins of the present invention. The process of producing transgenic plants is well known in the art. In general, the method comprises transforming a suitable host cell with one or more DNA segments that contain one or more promoters operatively linked to a coding region that encodes one or more of the disclosed PLD proteins. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant PLD expressed in a particular transgenic cell, the invention also provides for the expression of PLD-specific antisense mRNA. The use of antisense mRNA as a means of controlling or decreasing the amount of a given protein of interest in a cell is well known in the art.

Another aspect of the invention comprises a transgenic plant that expresses a gene or gene segment encoding one or more of the novel polypeptide compositions disclosed herein. As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more PLD-encoding transgenes, either native, synthetically modified, or mutated. In some instances, more than one transgene will be incorporated into the genome of the transformed host plant cell. Such is the case when more than one PLD-encoding DNA segment is incorporated into the genome of such a plant. In certain situations, it may be desirable to have one, two, three, four, or even more PLD polypeptides (either native or recombinantly-engineered) incorporated and stably expressed in the transformed transgenic plant.

A preferred gene that may be introduced includes, for example, a PLD polypeptide-encoding a DNA sequence from plant origin, such as those illustrated herein, and particularly one or more of those comprising one or more amino acid sequences described in SEQ ID NO:2.

Means for transforming a plant cell and the preparation of a transgenic cell line are well known in the art, and are discussed herein. Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed PLD polypeptides. These DNA constructs can further include structures such as promoters, enhancers, polylinkers, or even gene sequences that have positively- or negatively-regulating activity upon the particular genes of interest as desired. The DNA segment or gene may encode either a native or modified PLD polypeptide, which will be expressed in the resultant recombinant cells, and/or which will impart an improved phenotype to the regenerated plant, in this case, by altering or modulating the biosynthesis or lipid content in a transformed plant cell.

Such transgenic plants may be desirable for increasing lipid biosynthesis in a monocotyledonous or dicotyledonous plant, by incorporating into such a plant, a transgenic DNA segment encoding a PLD polypeptide. Particularly preferred plants include grains such as corn, wheat, millet, rye, rice, barley, and oats; legumes such as beans, soybeans, peas; tubers such as potatoes and sugar beets; fiber crops such as flax and cotton; turf and pasture grasses; tobacco, sunflower, safflower, canola, ornamental plants; shrubs; trees; vegetables, berries, citrus, fruits, cacti, succulents, and other commercially-important crops including garden, floral, and houseplants.

In a related aspect, the present invention also encompasses a seed produced by the transformed plant, a progeny from such seed, and a seed produced by the progeny of the original transgenic plant, produced in accordance with the above process. Such progeny and seeds will have one or more PLD transgene(s) stably incorporated into its genome, and such progeny plants will inherit the traits afforded by the introduction of a stable transgene in Mendelian fashion. All such transgenic plants having incorporated into their genome transgenic DNA segments encoding one or more PLD polypeptides or polypeptides are aspects of this invention. Particularly preferred transgenes for the practice of the invention include nucleic acid segments comprising one or more PLD gene(s).

4.16 Transformed Host Cells and Transformation Methods

A bacterial cell, a yeast cell, or a plant cell transformed with a PLD-encoding gene-containing expression vector of the present invention also represents an important aspect of the present invention. Furthermore, transgenic plants and the progeny and seeds derived from such a transformed or transgenic plant are also important aspects of this invention.

Such transformed host cells are often desirable for use in the expression of the various DNA gene constructs disclosed herein. In some aspects of the invention, it is often desirable to modulate, regulate, or otherwise control the expression of the gene segments disclosed herein. Such methods are routine to those of skill in the molecular genetic arts. Typically, when increased or over-expression of a particular gene is desired, various manipulations may be employed for enhancing the expression of the messenger RNA, particularly by using an active promoter, as well as by employing sequences, which enhance the stability of the messenger RNA in the particular transformed host cell.

Typically, the initiation and translational termination region will involve stop codon(s), a terminator region, and optionally, a polyadenylation signal. In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the expression construct during introduction of the DNA into the host.

Where no functional replication system is present, the construct will also preferably include a sequence of at least about 40 or 50 basepairs (bp) or so, preferably at least about 90 to about 100 or so bp, and usually not more than about 500 to about 1000 or so bp of a sequence homologous with a sequence in the host. In this way, the probability of legitimate recombination is enhanced, so that the gene will be integrated into the host and stably maintained by the host. Desirably, the PLD-encoding gene-promoter construct will be in close proximity to the gene providing for complementation as well as the gene providing for the competitive advantage. Therefore, in the event that a PLD-encoding gene is lost, the resulting organism will be likely to also lose the PLD gene and/or the gene providing for the competitive advantage, so that it will be unable to compete in the environment with the gene retaining the intact construct.

The PLD-encoding gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

Alternatively, the left and right T-DNA borders from the Ti plasmid may be used when integration is desired using *A. tumefaciens* vectors for plant transformation. The transformants can be isolated in accordance with conventional ways, usually employing a selection technique, which allows for selection of the desired organism as against unmodified organisms or transferring organisms, when present. The transformants then can be tested for presence of the genetic construct.

Genes or other nucleic acid segments, as disclosed herein, can be inserted into host cells using a variety of techniques that are well known in the art. Five general methods for delivering a nucleic segment into cells have been described: (1) chemical methods (Graham and VanDerEb, 1973); (2) physical methods such as microinjection (Capecchi, 1980), electroporation (U.S. Pat. No. 5,472,869; Wong and Neumann, 1982; Fromm et al., 1985), microprojectile bombardment (Wang et al., 1988; Tomes et al., 1990; Vain et al., 1993; U.S. Pat. No. 5,874,265, specifically incorporated herein by reference in its entirety), "gene gun" (Hilber et al., 1994; Yang et al., 1990); (3) viral vectors (Clapp, 1993; Danos and Heard, 1992; Eglitis and Anderson, 1988); (4) receptor-mediated mechanisms (Curiel et al., 1991; Wagner et al., 1992); and (5) bacterial-mediated delivery such as *A. tumefaciens* transformation (Smith and Hood, 1995).

For example, a large number of cloning vectors comprising a replication system in *E. coli* and a marker that permits selection of the transformed cells are available for preparation for the insertion of foreign genes into higher organisms, including plants. The vectors comprise, for example, plasmids (such as pBR322, pUC series, M13mp series, pACYC184, etc), cosmids, phage, and/or phagemids and the like. Accordingly, the disclosed polynucleotides can be inserted into a given vector at a suitable restriction site. The resulting plasmid may be used, for example, to transform bacterial cells such as *E coli* or *A. tumefaciens*. The bacterial cells are then cultivated in a suitable nutrient medium, harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary.

4.17 Methods for Making Transgenic Plants

In a further embodiment, the invention provides transgenic plant cells, transgenic plants, progeny, and seeds having stably incorporated into their genome at least a first transgene that encodes a PLD polypeptide that comprises at least a 15-amino acid contiguous sequence from SEQ ID NO:2. Exemplary transgenic plants are those having stably incorporated into their genome a selected nucleic acid sequence that comprises at least a first trangene that comprises at least a 18-basepair contiguous nucleic acid sequence from SEQ ID NO:1.

The progeny or offspring of such a transgenic plant, as well as its fruit, nuts, and/or seed, progeny from such fruit, nuts, and/or seeds, as well as all fruits, nuts and/or seeds arising from the second and all subsequent generation plants derived from such a parental transgenic plant, plant tissue or transformed plant host cell also represent important aspects of the present invention.

The invention also discloses and claims host cells, both native, and genetically engineered, which express the novel PLD-encoding sequence to produce polypeptides having PLD enzymatic activity.

Methods of using such cells to produce polypeptides and peptides are also disclosed. Such methods generally involve culturing the host cell under conditions effective to produce a PLD polypeptide or peptide, and obtaining the polypeptide so produced from said cell.

In yet another aspect, the present invention provides methods for producing a transgenic plant that expresses a nucleic acid segment encoding the novel PLD polypeptides of the present invention. The process of producing transgenic plants is well known in the art. In general, the method comprises transforming a suitable host cell with one or more nucleic acid segments that contain one or more promoters operatively linked to a coding region that encodes one or more of the disclosed PLD proteins. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant PLD polypeptide expressed in a particular transgenic cell, the invention also provides for the expression of PLD antisense mRNA. The use of antisense mRNA as a means of controlling or decreasing the amount of a given protein of interest in a cell is well known in the art.

Another aspect of the invention comprises a transgenic plant that expresses a gene or gene segment encoding one or more of the novel PLD polypeptide compositions disclosed herein. As used herein, the term "transgenic plant" is intended to refer to a plant that has stably incorporated DNA sequences, including but not limited to genes that are perhaps not normally present, DNA sequences not normally transcribed into RNA or translated into a protein ("expressed"), or any other genes or DNA sequences that one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more PLD-encoding transgenes, either native, synthetically modified, or mutated. In some instances, more than one transgene will be incorporated into the genome of the transformed host plant cell. Such is the case when more than one PLD-encoding DNA segment is incorporated into the genome of such a plant. In certain situations, it may be desirable to have one, two, three, four, or even more PLD proteins (either native or recombinantly-engineered) incorporated and stably expressed in the transformed transgenic plant.

A preferred selected nucleic acid sequence that may be introduced into a target host plant includes, for example, a polynucleotide that encodes a PLD polypeptide, and particularly one comprising a contiguous amino acid sequence from SEQ ID NO:2. Highly preferred nucleic acid sequences are those obtained from PLD-expressing plants, or any of those sequences that have been genetically engineered to decrease or increase the enzymatic activity of the PLD polypeptide in such a transformed host cell.

Means for transforming a plant cell and the preparation of a transgenic cell line are well known in the art, and are discussed herein.

The introduction of DNA by electroporation is well-known to those of skill in the art (see e.g., U.S. Pat. No. 5,324,253, specifically incorporated herein by reference in its entirety). In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. To effect transformation by electroporation one may employ either friable tissues such as a suspension culture of cells (U.S. Pat. No. 5,484,956; U.S. Pat. No. 5,886,244, each of which is specifically incorporated herein by reference in its entirety), or embryogenic callus (U.S. Pat. No. 5,405,765, each of which is specifically incorporated herein by reference in its entirety), or alternatively, one may transform immature embryos or other organized tissues directly. One would partially degrade the cell walls of the chosen cells by exposing them to pectin-degrading enzymes (pectolyases) or mechanically wounding in a controlled manner. Such cells would then be the recipient of DNA transfer by electroporation, which may be carried out at this stage, and transformed cells then identified by a suitable selection or screening protocol dependent on the nature of the newly incorporated DNA.

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

An advantage of microprojectile bombardment, in addition to it being an effective means of reproducibly stably transforming monocots, is that neither the isolation of protoplasts (Cristou et al., 1988) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with corn cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing damage inflicted on the recipient cells by projectiles that are too large.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described (Fraley et al., 1985; Rogers et al., 1988). Further, the integration of the Ti-DNA is a relatively precise process resulting in few rearrangements. The region of DNA to be transferred is defined by the border sequences, and intervening DNA is usually inserted into the plant genome as described (Spielmann et al., 1986; Jorgensen et al., 1987).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate construction of vectors capable of expressing various polypeptide-coding genes. The vectors described (Eichholtz et al., 1987), have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

Methods for transformation of cereal grains such as rice, corn, and wheat have also been well characterized (see e.g., U.S. Pat. No. 5,610,042, specifically incorporated herein by reference in its entirety).

Transformation of plant protoplasts can be achieved using methods based on calcium phosphate precipitation, polyethylene glycol treatment, electroporation, and combinations of these treatments (see, e.g., Potrykus et al., 1985; Lorz et al., 1985; Fromm et al., 1985; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts are described (Fujimura et al., 1985; Toriyama et al., 1986; Yamada et al., 1986; Abdullah et al., 1986).

Vectors, plasmids, cosmids, YACs (yeast artificial chromosomes) and DNA segments for use in transforming such cells will, of course, generally comprise either the operons, genes, or gene-derived sequences of the present invention, either native, or synthetically-derived, and particularly those encoding the disclosed PLD polypeptides and proteins. These DNA constructs can further include structures such as promoters, enhancers, polylinkers, or even gene sequences that have positively- or negatively-regulating activity upon the particular genes of interest as desired. The DNA segment or gene may encode either a native or modified PLD polypeptide or protein, which will be expressed in the resultant recombinant cells, and/or which will impart an improved phenotype to the regenerated plant Such transgenic plants may be desirable for increasing the biosynthesis of oils in a monocotyledonous or dicotyledonous plant, by incorporating into such a plant, a transgenic DNA segment encoding at least a first PLD polypeptide. Particularly preferred plants include grains such as safflower, canola, sunflower, tobacco, corn, wheat, rye, millet, rice, barley, and oats; legumes such as beans, peas, soybeans; tubers such as potatoes and sugar beets; fiber crops such as kapok, flax and cotton; turf and pasture grasses; ornamental plants; shrubs; trees; vegetables, berries, citrus, fruits, cacti, succulents, and other commercially-important crops including garden and houseplants.

In a related aspect, the present invention also encompasses a seed produced by the transformed plant, a progeny from such seed, and a seed produced by the progeny of the original transgenic plant, produced in accordance with the above process. Such progeny and seeds will have one or more PLD-encoding transgene(s) stably incorporated into its genome, and such progeny plants will inherit the traits afforded by the introduction of a stable transgene in Mendelian fashion. All such transgenic plants having incorporated into their genome transgenic DNA segments encoding one or more PLD polypeptides are aspects of this invention. Particularly preferred transgenes for the practice of the invention include nucleic acid segments comprising one or more nucleic acid sequences that encode a PLD polypeptide.

4.18 Expression Vectors

The present invention also provides an expression vector comprising at least one PLD-encoding gene-containing polynucleotide operably linked to an inducible promoter. Thus, in one embodiment an expression vector is an isolated and purified DNA molecule comprising a PLD coding region operably linked to a promoter that expresses the gene, which coding region is operatively linked to a transcription-terminating region, whereby the promoter drives the transcription of the coding region.

As used herein, the term "operatively linked" means that a promoter is connected to a nucleic acid region encoding functional RNA in such a way that the transcription of that functional RNA is controlled and regulated by that promoter. Means for operatively linking a promoter to a nucleic acid region encoding functional RNA are well known in the art.

The choice of which expression vector and ultimately to which promoter a polypeptide coding region is operatively linked depend directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the functional RNA to which it is operatively linked.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

A variety of methods have been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

4.19 DNA Segments as Hybridization Probes and Primers

In another aspect, DNA sequence information provided by the invention allows for the preparation of relatively short DNA (or RNA) sequences having the ability to specifically hybridize to gene sequences of the selected polynucleotides disclosed herein. The ability of such nucleic acid probes to specifically hybridize to all or portions of one or more PLD-encoding genes lends them particular utility in a variety of embodiments. Most importantly, the probes may be used in a variety of assays for detecting the presence of complementary sequences in a given sample, and in the identification of new species or genera of PLD-encoding genes from a variety of host organisms.

In certain embodiments, it is advantageous to use oligonucleotide primers. The sequence of such primers is designed using a polynucleotide of the present invention for use in detecting, amplifying or mutating a defined segment of the disclosed PLD-encoding genes (e.g., SEQ ID NO:1) from a sample using PCR™ technology. Segments of related PLD-encoding genes from other species, and particularly from other related plant species may also be amplified by PCR™ using such primers.

To provide certain of the advantages in accordance with the present invention, a preferred nucleic acid sequence employed for hybridization studies or assays includes sequences that are complementary to at least about 31 to 50 or so long nucleotide stretch of a PLD-encoding gene sequence. A size of at least 31 nucleotides in length helps to ensure that the fragment will be of sufficient length to form a duplex molecule that is both stable and selective. Molecules having complementary sequences over stretches greater than 31 bases in length are generally preferred, though, in order to increase stability and selectivity of the hybrid, and thereby improve the quality and degree of specific hybrid molecules obtained.

One will generally prefer to design nucleic acid molecules having gene-complementary stretches of about 31 to about 40 or 50 or so nucleotides, or even longer where desired. Such fragments may be readily prepared by, for example, directly synthesizing the fragment by chemical means, by application of nucleic acid reproduction technology, such as the PCR™ technology of U.S. Pat. No. 4,683,195, and U.S. Pat. No. 4,683,202, (each specifically incorporated herein by reference in its entirety), or by excising selected DNA fragments from recombinant plasmids containing appropriate inserts and suitable restriction sites.

Of course, for some applications, for example, where one desires to prepare mutants employing a mutant primer strand hybridized to an underlying template or where one seeks to isolate PLD-encoding gene sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 25° C. to about 60° C. Naturally, these ranges would encompass hybridization conditions that employ temperatures of about 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., or 74° C., and/or conditions that employ a salt concentration of about 0.20 M, 0.25 M, 0.30 M, 0.35 M, 0.40 M, 0.45 M, 0.50 M, 0.55 M, 0.60 M, 0.65 M, 0.70 M, 0.75 M, 0.80 M or 0.85 M.

Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In addition to the use in directing the expression of functional RNA of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of one or more PLD-encoding genes will find particular utility. Longer contiguous identical or complementary sequences, e.g., those of about 20, 21, 22, 23, 24, etc., 30, 31, 32, 33, 34, etc., 40, 41, 42, 43, 44, etc., 50, 51, 52, 53, 54, etc., 100, 200, 300, 400, 500, 600, 700, 800, 900, 1000, 1100, 1300, 1500, 2000, etc. (including all intermediate lengths and up to and including full-length sequences will also be of use in certain embodiments.

While the ability of such nucleic acid probes to specifically hybridize to PLD-encoding gene sequences makes them ideal for use in detecting the presence of complementary sequences in a given sample, other uses are also envisioned, including the use of the sequence information for the preparation of mutant species primers, synthetic gene sequences, gene fusions, and/or primers for use in preparing other PLD-encoding genetic constructs.

The use of a hybridization probe of about 14 or so nucleotides in length allows the formation of a duplex molecule that is both stable and selective. Molecules having contiguous complementary sequences over stretches of about 15, 16, 17, 18, 19, 20, 21, 22, 23, 24, 25, 26, 27, 28, 29, or 30 or more contiguous bases in length are generally preferred, though, in order to increase stability and selectivity of the hybrid, and thereby improve the quality and degree of specific hybrid molecules obtained. One will generally prefer to design nucleic acid molecules having gene-complementary stretches of about 31, 32, 33, 34, 35, 36, 37, 38, 39, or 40 or more contiguous nucleotides in length where desired. When longer polynucleotides are desired, one may employ nucleic acid segments having gene-complementary stretches of about 41, 42, 43, 44, 45, 46, 47, 48, 49, or even 50, 60, 70, 80, 90, or 100 or more contiguous nucleotides in length where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,195 and U.S. Pat. No. 4,683,202 (each of which is specifically incorporated herein by reference in its entirety), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one may employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 75° C. Naturally, these ranges would encompass hybridization conditions that employ temperatures of about 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., or 74° C., and/or conditions that employ a salt concentration of about 0.03 M, 0.04 M, 0.05 M, 0.06 M, 0.07 M, 0.08 M, 0.09 M, 0.10 M, 0.11 M, 0.12 M, 0.13 M, or 0.14 M. Such selective conditions tolerate little, if any, mismatch between the probe and the template or target strand, and would be particularly suitable for isolating particular DNA segments that are highly homologous to one or more of the PLD sequences disclosed herein.

Detection of DNA segments via hybridization is well known to those of skill in the art, and the teachings of U.S. Pat. No. 4,965,188 and U.S. Pat. No. 5,176,995 (each of which is specifically incorporated herein by reference in its entirety) are exemplary of the methods of hybridization analyses. Teachings such as those found in the texts of Maloy et al., 1994; Segal 1976; Prokop and Bajpai, 1991; and Kuby, 1994, are also particularly relevant.

In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmentally undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test nucleic acid (e.g., DNA, PNA, or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending upon, e.g., the G+C content, type of target nucleic acid, source of nucleic acid, size of the target sequence, length of the hybridization probe, etc.). Following washing of the hybridized surface so as to remove nonspecifically bound probe molecules, specific hybridization is detected, or even quantitated, by means of the label.

4.20 Plant Cells and Transgenic Plants Expressing Functional or Inactivated PLD Polypeptides In one embodiment, the invention provides a transgenic plant having incorporated into its genome a transgene that encodes either a functional or an inactivated PLD polypeptide. A further aspect of the invention is a transgenic plant having incorporated into its genome a transgene that encodes such a polypeptide. Other embodiments of the invention also concern the progeny of such a transgenic plant, as well as its seed, the progeny from such seeds, and seeds arising from the second and subsequent generation plants derived from such a transgenic plant.

The invention also discloses and claims host cells, both native, and genetically engineered, which express one or more genes encoding all or substantially all of a PLD polypeptide to produce the encoded polypeptide(s) in a suitably transformed host cell, and in particular, in a transformed plant cell.

In yet another aspect, the present invention provides methods for producing a transgenic plant that expresses such a nucleic acid segment. The process of producing transgenic plants is well known in the art. In general, the method comprises transforming a suitable host cell with one or more DNA segments that contain a promoter operatively linked to a coding region that encodes one or more PLD polypeptides. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant protein expressed in a particular transgenic cell, the invention also provides for the expression of an antisense oligonucleotide or other nucleic acid sequences that are complementary to the mRNA that encodes the expressed polypeptide. The use of antisense mRNA as a means of controlling or decreasing the amount of a given protein of interest in a cell is well known in the art.

As used herein, the term "transgenic plant" is intended to refer to a plant that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed plant, such as genes which may normally be present in the non-transformed plant but which one desires to either genetically engineer or to have altered expression.

It is contemplated that in some instances the genome of a transgenic plant of the present invention will have been augmented through the stable introduction of one or more transgenes, either native, synthetically modified, or mutated. In some instances, more than one transgene will be incorporated into the genome of the transformed host plant cell. Such is the case when more than one DNA segment is incorporated into the genome of such a plant. In certain situations, it may be desirable to have one, two, three, four, or even more PLD proteins (either native or recombinantly-engineered) incorporated and stably expressed in the transformed transgenic plant.

A preferred gene that may be introduced includes, for example, a DNA sequence from a plant that encodes a PLD polypeptide, and particularly one comprising the amino acid sequence of SEQ ID NO:2.

Means for transforming a plant cell and the preparation of a transgenic cell line are well known in the art, and are discussed herein. Vectors, plasmids, cosmids, bacterial artificial chromosomes (BACs), plant artificial chromosomes (PACs), yeast artificial chromosomes (YACs), and DNA segments for use in transforming such cells will, of course, generally comprise either the operons, genes, or gene-derived sequences of the present invention, either native, or synthetically-derived, and particularly those encoding the disclosed PLD polypeptides. These nucleic acid constructs can further include structures such as promoters, enhancers, polylinkers, or even gene sequences that have positively- or negatively-regulating activity upon the particular genes of interest as desired. The nucleic acid segment or gene may encode either a native or modified protein, which will be expressed in the resultant recombinant cells, and/or which will impart an improved phenotype to the regenerated plant Such transgenic plants may be desirable for modulating lipid biosynthesis in a population of monocotyledonous or dicotyledonous plants. Particularly preferred plants include grains such as corn, wheat, rye, rice, barley, and oats; legumes such as beans, soybeans; tubers such as potatoes; fiber crops such as flax and cotton; turf and pasture grasses; ornamental plants; shrubs; trees; vegetables; berries; citrus crops, including oranges, tangerines, grapefruit, limes, lemons, and the like; fruits, cacti, succulents, and other commercially-important crops including greenhouse, garden and houseplants.

In a related aspect, the present invention also encompasses a seed produced by the transformed plant, a progeny from such seed, and a seed produced by the progeny of the original transgenic plant, produced in accordance with the above process. Such progeny and seeds will have one or more PLD-encoding transgene(s) stably incorporated into its genome, and such progeny plants will inherit the traits afforded by the introduction of a stable transgene in Mendelian fashion. All such transgenic plants having incorporated into their genome transgenic DNA segments encoding one or more PLD polypeptides are aspects of this invention.

4.21 Isolating Homologous Gene and Gene Fragments Encoding PLD

The polynucleotide sequences of the subject invention include not only full-length sequences but also fragments of these sequences, (including e.g., fusion proteins), which retain the PLD enzymatic activity of the sequences specifically exemplified herein in SEQ ID NO:2. It should be apparent to a person skilled in this art that the various genetic constructs encoding PLD polypeptides can be identified and obtained through several means. The PLD-encoding genes, or portions thereof, may be obtained from a culture depository, or constructed synthetically, for example, by use of a gene machine. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes or gene fragments that encode biologically active polypeptides may be obtained using a variety of other restriction enzymes. Proteases may be used to directly obtain active fragments of these constructs.

The nucleotide segments that are used as probes according to the invention may be synthesized by use of nucleic acid synthesizers using standard procedures. In the use of the nucleotide segments as probes, the particular probe is labeled with any suitable label known to those skilled in the art, including radioactive and non-radioactive labels. Typical radioactive labels include $^{32}P$, $^{125}I$, $^{131}I$, $^{35}S$, $^{14}C$, $^{3}H$, or the like. A probe labeled with a radioactive isotope can be constructed from a nucleotide sequence complementary to the DNA sample by a conventional nick translation reaction, using a DNase and DNA polymerase. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting.

Non-radioactive labels include, for example, ligands such as biotin or thyroxine, as well as enzymes such as hydrolases or peroxidases, or the various chemiluminescers such as luciferin, or fluorescent compounds like fluorescein and its derivatives. The probe may also be labeled at both ends with different types of labels for ease of separation, as, for example, by using an isotopic label at the end mentioned above and a biotin label at the other end.

Duplex formation and stability depend on substantial complementarity between the two strands of a hybrid, and, as noted above, a certain degree of mismatch can be tolerated. Therefore, the probes of the subject invention include mutations (both single and multiple), deletions, insertions of the described sequences, and combinations thereof, wherein said mutations, insertions and deletions permit formation of stable hybrids with the target polynucleotide of interest. Mutations, insertions, and deletions can be produced in a given polynucleotide sequence in many ways, by methods currently known to an ordinarily skilled artisan, and perhaps by other methods which may become known in the future.

The potential variations in the probes listed are due, in part, to the redundancy of the genetic code. Because of the redundancy of the genetic code, i.e. more than one coding nucleotide triplet (codon) can be used for most of the amino acids used to make proteins. Therefore different nucleotide sequences can code for a particular amino acid. Thus, the amino acid sequences of the disclosed polypeptides can be prepared by equivalent nucleotide sequences encoding the same amino acid sequence of the protein or peptide. Accordingly, the subject invention includes such equivalent nucleotide sequences. Also, inverse or complement sequences are an aspect of the subject invention and can be readily used by a person skilled in this art. In addition it has been shown that proteins of identified structure and function may be constructed by changing the amino acid sequence if such changes do not alter the protein secondary structure (Kaiser and Kezdy, 1984). Thus, the subject invention includes mutants of the amino acid sequence depicted herein that do not alter the protein secondary structure, or if the structure is altered, the biological activity is substantially retained. Further, the invention also includes mutants of organisms hosting all or part of one or more of the DNA constructs of the invention. Such mutants can be made by techniques well known to persons skilled in the art. For example, UV irradiation can be used to prepare mutants of host organisms.

4.22 Peptide Nucleic Acid Compositions

In certain embodiments, the inventors contemplate the use of peptide nucleic acids (PNAs) in the practice of the methods of the invention. PNAs are DNA analogs that mimic the structure of the polynucleotide, in which the nucleobases are attached to a pseudopeptide backbone (Good and Nielsen, 1997). PNAs can be utilized in a number of methods that traditionally have used RNAs or DNAs (U.S. Pat. No. 5,786,461; U.S. Pat. No. 5,773,571, U.S. Pat. No. 5,766,855; U.S. Pat. No. 5,736,336; U.S. Pat. No. 5,719,262; and U.S. Pat. No. 5,539,082, each of which is specifically incorporated herein by reference in its entirety). Often PNA sequences perform better in techniques than the corresponding RNA or DNA sequences and have utilities that are not inherent to RNA or DNA. Methods of making, and using PNAs are also found in Corey (1997).

PNAs when delivered within cells have the potential to be general sequence-specific regulators of gene expression. Reviews of PNAs and their use as antisense and anti-gene agents exist (Nielsen et al., 1993; Hanvey et al., 1992; and Good and Nielsen, 1997). Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al, 1996), in situ hybridization (Thisted et al., 1996), and in an alternative to Southern blotting (Perry-O'Keefe, 1996).

4.23 Antisense Oligonucleotides Targeted to mRNA

In certain embodiments, the inventors contemplate the use of antisense compositions to negatively regulate the expression of a gene encoding PLD in a host cell. The end result of the flow of genetic information is the synthesis of protein. DNA is transcribed by polymerases into messenger RNA and translated on the ribosome to yield a folded, functional protein. Thus, even from this simplistic description of an extremely complex set of reactions, it is obvious that there are several steps along the route where protein synthesis can be inhibited. The native DNA segment encoding PLD has two strands: a sense strand and an antisense strand held together by hydrogen bonding. The messenger RNA encoding PLD has the same nucleotide sequence as the sense DNA strand except that the DNA thymidine is replaced by uridine. Thus, antisense nucleotide sequences will bind to the mRNA encoding the PLD polypeptides and inhibit production of the corresponding protein.

The targeting of antisense oligonucleotides to bind mRNA is one mechanism to shut down protein synthesis. For example, the synthesis of polygalactauronase and the muscarine type-2 acetylcholine receptor are inhibited by antisense oligonucleotides directed to their respective mRNA sequences (U.S. Pat. No. 5,739,119 and U.S. Pat. No. 5,759,829, U.S. Pat. No. 5,801,154; U.S. Pat. No. 5,789,573; U.S. Pat. No. 5,718,709 and U.S. Pat. No. 5,610,288, each specifically incorporated herein by reference in its entirety).

In illustrative embodiments, antisense oligonucleotides may be prepared which are complementary nucleic acid sequences that can recognize and bind to target genes or the transcribed mRNA, resulting in the arrest and/or inhibition of deoxyribonucleic acid (DNA) transcription or translation of the messenger ribonucleic acid (mRNA). These oligonucleotides can be expressed within a host cell that normally expresses PLD-specific mRNA to reduce or inhibit the expression of this mRNA. Thus, the oligonucleotides may be useful for reducing the level of PLD polypeptide in a suitably transformed host cell or transgenic plant.

The native nucleic acid segment encoding PLD has, as do all such plant DNAs, two strands: a sense strand and an antisense strand held together in a duplex formation by hydrogen bonding. The messenger RNA (mRNA) encoding PLD has the same nucleotide sequence as the sense DNA strand except that the thymidine in DNA is replaced by uridine in DNA. Thus, preferred antisense oligonucleotide compositions for use in the practice of the present invention are those sequences that specifically bind to the mRNA coding for PLD and that inhibit or reduce the expression of the PLD polypeptide encoding by that mRNA.

The present invention provides an antisense oligonucleotide composition comprising at least a first oligonucleotide of at least about 9 to about 45 or so bases in length, wherein the oligonucleotide specifically binds to a portion of mRNA expressed from a gene encoding a plant PLD polypeptide, and further wherein binding of the oligonucleotide to the mRNA is effective in decreasing the activity of or reducing the quantity of the PLD enzyme in a host plant cell expressing the mRNA.

In certain aspects of the invention, the oligonucleotide comprises deoxyribonucleic acid, ribonucleic acid, or peptide-nucleic acid. In particular embodiments, the oligonucleotide comprises a sequence of at least nine, at least ten, at least eleven, at least twelve, at least thirteen, or at least fourteen, up to and including the full-length contiguous sequences from SEQ ID NO:1. When longer antisense molecules are required, one may employ an oligonucleotide that comprises a sequence of at least fifteen, at least sixteen, at least seventeen, at least eighteen, at least nineteen, or at least twenty, up to and including the full-length contiguous sequences from SEQ ID NO:1. Such antisense molecules may comprise even longer contiguous nucleotide sequences, such as those comprising about 21, about 22, about 23, about 24, about 25, about 26, about 27, about 28, about 29, or about 30 or so contiguous nucleotides from SEQ ID NO:1.

4.24 Definitions

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a, polynucleotide sequence, wherein the polynuctetide sequence in the comparison window may comprise additions or deletions (i.e. gaps) compared to the reference sequence (which does not comprise additions or deletions) for optimal alignment of the two sequences. Generally, the comparison window is at least 20 contiguous nucleotides in length, and optionally can be 30, 40, 50, 60, 70, 80, 90, or 100 contiguous nucleotides, or even longer depending upon the particular analysis. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al., (1981); by the homology alignment algorithm of Needleman et al., (1970); by the search for similarity method of Pearson et al. (1988); by computerized implementations of these algorithms, including, but not limited to: CLUSTAL in the PC/Gene program by Intelligenetics (Mountain View, Calif.); GAP, BESTFIT, BLAST, FASTA, and TFASTA in the Wisconsin Genetics Software Package, Genetics Computer Group (Madison, Wis.); the CLUSTAL program is well described by Higgins et al. (1988); Higgins et al. (1989); Corpet et al. (1988); Huang et al. (1992), and Person et al. (1994); preferred computer alignment methods also include the BLASTP, BLASTN, and BLASTX algorithms (Altschul et al., 1990). Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e. gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least about 70% sequence identity, preferably at least about 80%, more preferably at least about 90%, and most preferably at least about 95% to about 99%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least about 60%, more preferably at least about 70%, at least about 80%, at least about 90%, and most preferably at least about 95% to about 99%.

Another indication that nucleotide sequences are substantially identical is if two molecules hybridize to each other under stringent conditions. Generally, stringent conditions are selected to be about 5° C. to about 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typically, stringent wash conditions are those in which the salt concentration is about 0.02 M at pH 7 and the temperature is at least about 50° C., about 55° C., or even at least about 60° C., about 65° C., or at least about 70° C. or 75° C. so. However, nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least about 70% sequence identity to a reference sequence, preferably at least about 80%, more preferably at least about 85%, most preferably at least about 90% or at least about 95% to about 99% or so sequence identity to the reference sequence over a specified comparison window. Preferably, optimal alignment is conducted using the homology alignment algorithm of Needleman et al. (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The proteins of the invention may be altered in various ways including amino acid substitutions, deletions, truncations, and insertion. Methods for such manipulations are generally known in the art. For example, amino acid sequence variants of the proteins can be prepared by mutations in the DNA that encode them. Methods for mutagenesis and nucleotide sequence alterations are well known in the art (see e.g., Kunkel, 1985; Kunkel et al., 1987; U.S. Pat. No. 4,873,192; Walker and Gaastra, 1983, each of which is specifically incorporated herein by reference in its entirety).

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired PLD or ΔPLD activity.

Obviously, the mutations that will be made in the DNA encoding the variant must not place the sequence out of reading frame and preferably will not create complementary regions that could produce secondary mRNA structure (see e.g., Eur. Pat. Appl. Publ. No. 75,444, specifically incorporated herein by reference in its entirety).

"Seed-specific" promoters of the invention may also include embryo-specific promoters. Such promoters may include, but are not limited to, globulin 1, cruciferin, napin, β-conglycinin, phaseolin, and the like, as well as other promoters associated with storage proteins or involved in fatty acid or lipid biosynthesis.

The polynucleotides of the invention may be provided in one or more expression cassettes or genetic constructs to facilitate introduction and stable integration into the plant genome. Such expression cassettes may comprise one or more transcriptional initiation regions linked to a coding sequence or antisense sequence of the particular PLD or ΔPLD sequence. Such an expression cassette is generally provided with a plurality of restriction sites for insertion of the sequence to be under the transcriptional regulation of the regulatory regions. The expression cassette may additionally contain one or more selectable marker genes.

The transcriptional initiation region, the promoter, may be native (i.e. analogous) or foreign (i.e. heterologous) to the plant host. Additionally, the promoter may be a synthetic sequence. By "foreign," it is intended that the transcriptional initiation region not be found in the native plant into which the transcriptional initiation region is introduced. For example, a spinach PLD gene would be consider a "foreign" gene if introduced into the genome of a non-spinach plant, such as corn or soybeans.

The transcriptional cassette may include in the 5' to 3' direction of transcription, a transcriptional and translational initiation region, a PLD or ΔPLD coding sequence, and a transcriptional and translational termination region functional in the particular plant species into which the construct is introduced. The termination region may be native with the transcriptional initiation region, may be native with the DNA sequence of interest, or may be derived from another source. Convenient termination regions are available from the Ti-plasmid of *A. tumefaciens* such as the octopine synthase and nopaline synthase termination regions (Guerineau et al., 1991; Proudfoot, 1991; Sanfacon et al., 1991; Mogen et al., 1990; Munroe et al., 1990; Ballas et al., 1989; Joshi et al., 1987, each of which is specifically incorporated herein by reference in its entirety).

In preparing the expression cassette, the various polynucleotide fragment(s) may be manipulated, so as to provide for the DNA sequences in the proper orientation and, as appropriate, in the proper reading frame. Toward this end, adapters or linkers may be employed to join the polynucleotides or other manipulations may be involved to provide for convenient restriction sites, removal of superfluous DNA, removal of restriction sites, or the like. For this purpose, in vitro mutagenesis, primer repair, restriction, annealing, resubstitutions (e.g., transitions and transversions), may be involved.

The modulation of lipid biosynthesis can be achieved in any plant of interest. Of particular interest are plants useful for human foodstuffs and domestic animal feedstock. Such plants include forage and seed crop plants, and preferably crops such as cereals and oilseed crops. Of particular interest are plants where the seed is produced in high amounts, or the seed or a seed part is edible. Seeds of interest include the oilseeds, such as from *Brassica*, cotton, soybean, safflower, canola, sunflower, coconut, palm, etc.; grain seeds such as wheat, rice, corn, etc.; other seeds including oats, pumpkin, squash, poppy, sesame, peanut, peas, beans and other legumes, cocoa, coffee, etc.; and tree nuts such as walnuts, pecans, almonds, etc. Especially preferred plants are corn, soybean, legumes, safflower, sunflower, canola, *Brassica*, wheat, rye, rice, millet, sorghum, alfalfa, and the like.

The modified plant may be grown into plants in accordance with conventional ways (McCormick et al., 1986). These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited into the progeny and subsequent generations of the transformed plant. Likewise, the seeds from the transformed plant or from a progeny or subsequent generation of the plant may be harvested and assayed to ensure the desired phenotype has been achieved in the progeny and the seeds from the transgenic plant and its offspring.

In accordance with the present invention, nucleic acid sequences include and are not limited to DNA (including and not limited to genomic or extragenomic DNA), genes, RNA (including and not limited to mRNA and tRNA), nucleosides, and suitable nucleic acid segments either obtained from native sources, chemically synthesized, modified, or otherwise prepared by the hand of man.

In accordance with the present invention, nucleic acid sequences include and are not limited to DNA, including and not limited to cDNA and genomic DNA, genes; RNA, including and not limited to mRNA and tRNA; PNAs (peptide nucleic acids), antisense sequences, nucleosides, and suitable nucleic acid sequences such as those set forth herein, as well as variants in the nucleic acid sequences such as alterations, deletions, mutations, and homologs capable of expressing the PLD polypeptides of the present invention.

As such the present invention also concerns DNA segments, that are free from total genomic DNA and that encode the novel PLD proteins disclosed herein. DNA segments encoding these peptide species may prove to encode proteins, polypeptides, subunits, functional domains, and the like of PLD-related or other non-related gene products. In addition these DNA segments may be synthesized entirely in vitro using methods that are well known to those of skill in the art.

As used herein, the term "DNA segment" refers to a DNA molecule that has been isolated free of total genomic DNA of a particular species. Therefore, a DNA segment encoding a PLD polypeptide or peptide refers to a DNA segment that contains PLD polypeptide coding sequences yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phagemids, phage, viruses, and the like.

Similarly, a DNA segment comprising an isolated or purified nucleic acid or gene sequence that encodes a PLD polypeptide refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes both genomic sequences, operon sequences and smaller engineered gene segments that express, or may be adapted to express, proteins, polypeptides or peptides.

"Isolated substantially away from other coding sequences" means that the gene of interest, in this case, a gene encoding a PLD polypeptide, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode a PLD peptide or polypeptide species that includes within its amino acid sequence an amino acid sequence essentially as set forth in SEQ ID NO:2.

The term "a sequence essentially as set forth in SEQ ID NO:2" means that the sequence substantially corresponds to a portion of the sequence of SEQ ID NO:2, and has relatively few amino acids that are not identical to, or a biologically functional equivalent of, the amino acids of any of these sequences. The term "biologically functional equivalent" is well understood in the art and is further defined in detail herein (e.g., see Illustrative Embodiments).

Accordingly, sequences that have between about 65% and about 75% or between about 75% and about 85%, or more preferably between about 86% and about 90%, or even more preferably between about 91% or 92% or 93% and about 97% or 98% or 99% amino acid sequence identity or functional equivalence to the amino acids of SEQ ID NO:2, will be sequences that are "essentially as set forth in SEQ ID NO:2."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e. introns, which are known to occur within genes.

The following words and phrases have the meanings set forth below.

A, an: In accordance with long standing patent law convention, the words "a" and "an" when used in this application, including the claims, denotes "one or more".

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g., plant protoplast or explant).

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

5.0 EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Synthesis of Nape

Chemical synthesis of radiolabeled NAPE was modified from a reaction scheme originally proposed by Dawson et al. (1969). The synthesis is illustrated in FIG. 1A and FIG. 1B. A 10-fold increase in phosphatidylethanolamine concentration forced the reaction toward completion. The modification led to a three-fold greater conversion of product (FIG. 1) than previously reported (DeSouza, 1997).

[$^{14}$C]NAPE was synthesized chemically using 1 µCi of sn-1,2-dioleoyl-glycero-3-phosphoryl-[ethanolamine-2-$^{14}$C] ethanolamine (54 mCi/mmol). 2.7 µmol of nonradiolabeled dioleoyl-PE, and 8.3 µmol of palmitoyl chloride as previously described (Dawson et al., 1969).

NAPE was separated from PE by silica-gel thin-layer chromatography, recovered in chloroform, and quantified by liquid scintillation counting. This procedure had a routine conversion from PE to NAPE of 90% or greater.

L-3-Phosphatidyl [2-$^{14}$C] ethanolamine, 1,2-dioleoyl purchased from Amersham Life Sciences (Elk Grove, Ill.). Dioleolyl-[2$^{14}$C-oleoyl]glycero-3-P-choline was purchased from Dupont, NEN Life Sciences (Boston, Mass.), Phosphatidylcholine, polyphosphatidylinositol-bisphosphate ($PEP_2$), phosphatidylethanolamine(dioleoyl), palmitoyl chloride, ampicillin, phenylmethylsulfonyl fluoride, cabbage PLD Type V, *Streptomyces chromofuscus* PLD, bovine serum albumin, Coomasssie Brilliant Blue, and IPTG were obtained from Sigma Chemical Co. (St. Louis, Mo.). All other reagents were purchased from Fisher Scientific (Pittsburgh, Pa.), unless otherwise specified.

5.2 Example 2

Expression of Active PLDs in *E. coli*

The recombinant castor bean PLD α and the *A. thalania* PLD β, γ and δ in pBluescript SK(−) were obtained from Dr. Xenmin Wang (Department of Biochemistry, Kansas State University, Manhattan, Kans.). The following protocol was adapted from previously described methods (Pappan et al., 1997b). Expression of PLD α, β, β and δ from their cDNAs was performed using pBluescript SK(−) (Strategene, La Jolla, Calif.) containing the cDNA inserts in *E. coli* JM109 cells (Promega, Madison, Wis.). Fifty microliters of an overnight culture containing the transformed JM109 cells were added to 25 ml of LB medium with 50 μg/ml ampicillin. The cells were incubated at 37° C. with shaking for 3 h, and then IPTG was added to a final concentration of 2 mM. The cells were grown overnight at 30° C. and pelleted by centrifugation for 10 min at 2000 rpm (Beckman TJ-6 rotor). The cells were then resuspended in an assay mixture containing 50 mM Tris-HCl (pH 8.0), 150 mM NaCl, 0.25 mM phenmethylsulfonyl fluoride, 2 mM EDTA and then pelleted by centrifugation for 10 min at 2000 rpm. The cells were lysed by sonication in the resuspension buffer and cell debris was removed by centrifigation at 10,000×g for 5 min. Supernatants were used for assays of enzyme activity and protein content.

5.2.1 PLD Activity Assays and NAE Inhibition Studies

PLD isoforms were assayed under two different sets of conditions. These conditions were previously determined to yield optimal activity in vitro (Pappan et al., 1997a; 1997b; 1998).

5.2.2 $PIP_2$-Dependent Assay

The basic assay mixture contained 100 mM Mes buffer (pH 7.0), 50 μM $CaCl_2$, 80 mM KCl, 0.4 mM lipid vesicles, and 20 μg of protein from *E. coli* lysates in a total volume of 150 μL. PLD activity toward PC was assayed in the presence of 1% ethanol (vol./vol.). Lipid vesicles for PC hydrolysis included 16 nmol dioleoyl-[oleoyl-2$^{14}$C]glycero-3-P-choline (0.05 μCi) PC, 112 mmol dioleoyl PE, and 6 nmol $PIP_2$. Lipid vesicles for NAPE hydrolysis were composed of 16 nmol [$^{14}$C]NAPE (0–006 μCi), 112 mmol dioleoyl PE, and 6 nmol of $PIP_2$. PLD activity was measured and evaluated by radiometric scanning of TLC separation of lipid soluble reaction products.

5.2.3 High Calcium, $PIP_2$-Independent Assay

The basic assay mixture contained 100 mM MES buffer (pH 6.5), 25 mM $CaCl_2$, 0.5 mM SDS, 0.4 mM lipid vesicles containing PC or NAPE:PC (1:1 molar ratio), and 20 μg of protein. Hydrolytic activity was assessed by measuring the production of radiolabeled phosphatidylethanol or NAE.

Control assays were performed using 20 μg of protein from lysed bacteria minus IPTG. The reaction was initiated by the addition of enzyme and proceeded at 30° C. for 30 min in a reciprocal shaking water bath at 120 rpm (Precision Instruments, Model 25, Chicago, Ill.). Reactions were stopped by addition of 2 ml boiling isopropanol.

5.2.4 NAE Inhibition of Phospholipase D α

Activity assays were conducted with castor bean, cabbage, and *Streptomyces chromofuscus* PLD in the presence of different concentration and species of NAE to examine possible effects on enzyme activity. The assay mixture contained the above components as mentioned for high calcium, $PIP_2$-independent assay mixture with a modification of 2 mM PC and NAE (12:0–18:3) at various concentrations. Enzyme (20 μg for castor bean and 0.5 and 1 unit for cabbage and *S. chromofuscus*, respectively) (Chapman and Moore, 1993a) was added and the reaction continued for 15 or 30 min at 30° C. in a reciprocal shaking water bath at 120 rpm. Reactions were halted by the addition of 2 ml boiling isopropanol.

NAEs were synthesized by the addition of 25 mg of acyl chloride in 2.5 ml of dichloromethane to 2.5 ml of ethanolamine. Reaction was allowed to proceed for 15 min at room temperature with gentle swirling. The reaction was stopped by the addition of 10 ml of ultrapure water. The organic layer was washed an additional two times with 10 ml of ultrapure water. Samples were dried under a stream of $N_2$, weighed and resuspended in methanol. NAE yield and purity were determined by GC-MS.

5.2.5 Lipid Extraction

Lipid extractions from assay reactions were based on previously described methods by Chapman and Moore (1993). Hot isopropanol (70° C.) was routinely used (2 ml) to inactivate the enzyme following assays. The alcohol/aqueous mixture was then allowed to cool before adding chloroform (1 ml) for extraction for 1 hour (or overnight at 4° C.). Mixtures were partitioned by the addition of 2 ml 1M KCl and 1 ml $CHCl_3$. Centrifugation at 2000 rpm for 5 min (Beckman TJ-6 centrifuge Fullerton, Calif.) facilitated partitioning of the two phases. The aqueous phase was aspirated off and the chloroform layer was washed two more times with 2 ml 1M KCl. The chloroform/lipid mixture remaining was transferred to 3 ml scintillation vials (Fisher) and evaporated to dryness under $N_2$. The lipids were resuspended in 50 μl of chloroform:methanol (2:1) and analyzed by thin-layer chromatography and radiometric scanning.

5.2.6 Thin Layer Chromatography

Lipid separation was performed using one-dimensional TLC. The lipid samples (50 μl) were applied to 20×20 cm silica gel G plates (Whatman, Clifton, N.J.) having a layer thickness of 250 μm. NAPE/NAE separation was conducted first in hexane:diethylether (80:20) for 45 min, and then second in chloroform:methanol:water (80:35:1) for 60 min in the same direction. PC/phosphatidylethanol separation was performed in chloroform:methanol:ammonium hydroxide (65:35:5, vol./vol./vol.) for 55 min. The lipids were visualized by a brief exposure to iodine vapor. Radiolabeled product was quantified as a percentage of the total radioactive lipid by radiometric scanning (System 200 Imaging Scanner, Bioscan, Washington, D.C.). Enzyme activity was calculated based on the radiospecific activity of substrate.

5.2.7 Determination of Protein Content

Protein content was estimated by the method of Bradford (1976) using bovine serum albumin as the protein standard. One milliliter of Bradford reagent (0.117 mM Coomassie Blue G; 0.85% phosphoric acid; 4.75% ethanol) was added to a mixture containing 2–50 μl of protein sample and 50 μl of 1 N NaOH. The mixtures were allowed to stand for 5 min before measuring absorbance at 595 nm in a spectrophotometer (Milton Roy Spectronic Genesys 5, Rochester, N.J.) against appropriate blanks.

5.2.8 Degenerate Primer Design

Degenerate oligonucleotide primers were synthesized and purified by Bio-Synthesis, Inc. (Lewisville, Tex.). Primers were based on the amino acid sequences from *A. thaliana* PLD isoforms β and γ (Qin et al., 1997). Table 1 provides a list of the primers along with the predicted $T_m$ and the degree of degeneracy for each.

5.2.9 Amplification of cDNA by PCR™

A tobacco cDNA library (provided by Dr. G. An, Institute of Biological Chemistry, Washington State University, Pullman, Wash.) was constructed from mRNA isolated from tobacco NT-1 (*Nicotiana tabacum* L.) cell line in early exponential growth phase. Double stranded cDNA was packaged into the lambda ZAPII library, (Stratagene, La Jolla, Calif.) with external EcoRI and NotI linkers (Pharmacia, Piscataway, N.J.). The average insert size in the cDNA library was approximately 1 kb.

Two microliters of the supernatant containing the bacteriophage of the tobacco cDNA library in SM buffer (5.8 g of NaCl, 2.0 g of $MgSO_4$—$H_2O$, 50.0 ml of 1 M Tris-HCl pH 7.5, and 5.0 ml of 2% [wt./vol.] gelatin) was used as template for PCR™ reactions. The supernatant was heated for 5 min at 70° C. to lyse phage heads, cooled at 4° C. for 5 min, and added to the reaction mixture for a final volume of 50 µl. The PCR™ reaction mixture contained 10 mM Tris-HCl (pH 8.3), 2 mM $MgCl_2$, 50 mM KCl, 0.1% Triton X-100™, 0.2 mM each of dATP, dTTP, dGTP, and dCTP, 1.25 units of AmpliTaq Gold™ DNA polymerase (Perkin-Elmer, Foster City, Calif.) and 1 µM each of the forward and reverse primers. A "hot start" method was implemented according to manufacturer's instructions followed by amplification in a thermal cycler (Model 2400, Perkin-Elmer). The amplification was performed for 35 cycles with 30 sec at 94° C., 30 sec at 55° C. to 65° C. (annealing temperatures were varied to optimize PCR™ products) and 1 min at 72° C. After the last cycle, the amplification was extended for 10 min at 72° C. PCR™ amplification products were electrophoresed in 3% agarose gels in standard TAE buffer (0.04 M Tris-acetate, 0.001 M EDTA, pH 8.0) for 2.5 h at 70 V. A 1.2-kb PCR™ product was purified from agarose gels using a Prep-a-Gene™ DNA purification kit (Bio-Rad, Hercules, Calif.), according to manufacturer's instructions.

Degenerate primer sequences were designed from the amino acid sequences of the *A. thalania* PLD β and γ. Synthesis and purification was performed by Bio-Synthesis, Inc. (Lewisville, Tex.).

5.2.10 Amplification of cDNA by RT-PCR™

Total RNA was extracted from tobacco KY-14 (*Nicotiana rabacum* L.) cell line and from various cotton organs (cotyledons, hypocotyls, roots, leaves and embryos) by the modified hot borate method of Wan and Wilkins (1994). Total RNA (0.2 µg/µl) was used for first-strand cDNA synthesis with 5 units of avian myeloblastosis virus (AMV) reverse transcriptase. First-strand synthesis along with the subsequent amplification cycles was carried out using Access RT-PCR™ System (Promega). First-strand synthesis was carried out at 48° C. for 45 min in a thermal cycler (Perkin-Elmer model 2400) followed by 2 min at 94° C. to inactivate the AMV reverse transcriptase and 40 cycles of amplification. The amplification cycles were carried out as previously described. The final round of amplification was followed by a 7 min extension at 72° C.

TABLE 1

DEGENERATE OLIGONUCLEOTIDE PRIMERS FOR PCR™ AND RT-PCR™ STUDIES

| Primer | Amino acid sequence[a]<br>Nucleotide sequence[b] | Length (nt) | $T_m$[c] (° C.) | Degeneracy (n-fold) |
|---|---|---|---|---|
| −[d]1 | GgQHKTIEMM (SEQ ID NO:3)<br>5'-catcatytcdatngtyttrtgytgcc-3' (SEQ ID NO:4) | 26 | 70 | 192 |
| +2 | IYTHHEKac (SEQ ID NO:5)<br>5' athtayacncaycaygaraarac3' (SEQ ID NO:6) | 23 | 54 | 384 |
| −3 | CnIYTHHEKac (SEQ ID NO:7)<br>5'-gtyttytcrtgrtgngtrtadatng3' (SEQ ID NO:8) | 25 | 63 | 1536 |
| +4 | ECWFWCgg (SEQ ID NO:9)<br>5' gartgytggttytggtgygg3' (SEQ ID NO:10) | 20 | 67 | 16 |
| +5 | HGKCWEDM (SEQ ID NO:11)<br>5' cayggnaartgytgggargayatg3' (SEQ ID NO:12) | 24 | 68 | 128 |
| −6 | EEPENMECg (SEQ ID NO:13)<br>5' crcaytccatrttytcnggytcytc3' (SEQ ID NO:14) | 25 | 69 | 256 |

[a]Amino acid sequences are capitalized.
[b]Nucleotide sequences are in lower case. Symbols used to denote multiple sequences are as follows: y = C or T; r = A or G; d = G or A or T; n = A or C or G or T.
[c]$T_m$'s were calculated using "DNA Synthesis Oligo Calculator" (http://www.biotech.ufl.edu/cgi-bin/doa.cgi/).
[d]The + and − signs indicate the coding strand or complimentary to the coding strand, respectively.

5.2.11 Subcloning of PCR™ Products

PCR™ products (in 5 µl) were reamplified in a 50 µl reaction mixture containing 20 mM Tris-HCl (pH 8.0), 2 mM $MgCl_2$, 10 mM KCl, 6 mM $(NH_4)_2SO_4$, 0.1% Triton X100™, 10 µg/ml nuclease-free BSA, 2.5 units of Pfu DNA polymerase (Stratagene), 0.2 mM total of dATP, dTTP, dGTP, dCTP and 0.5 µM of the same primers used in original amplification. The reaction was incubated for 45 sec at 95° C., then followed by 35 cycles of amplification with 30 sec at 95° C., 30 sec at 55° C. to 65° C. (annealing temperature was identical to original PCR™ amplification), 2.5 min at 72° C. After the last cycle, the amplification was extended for 10 min at 72° C. The PCR™ reaction product was immediately purified from the reaction mixture using the Prep-A-Gene™ DNA purification kit. An aliquot (5 µl) was quantified in a 3% agarose gel with DNA molecular mass markers (10–200 ng/band, corresponding to 100–2000 bp, respectively, GIBCO BRL, Rockville, Md.) stained overnight with ethidium bromide.

Purified PCR™ products were subcloned (blunt-end ligation) into pZErO-2.1™ (Invitrogen, Carlsbad, Calif.) digested with EcoRV (Promega) (5:1 PCR™ product:vector ratio) according to manufacturer's instructions using Fast-Link™ DNA ligation kit (Epicentre Technologies Madison, Wis.). One Shot™ Top 10 *E. coli* cells (Invitrogen) were transformed with ligated plasmids. The *E. coli* cells were made competent by cell suspension in 0.1 M calcium chloride and 0.01 M rubidium chloride (Seidman et al, 1997). The ligation/transformation mixture was plated on selection media containing NZY (21 mg/ml), 0.05 mg/ml kanamycin, and 1 mM IPTG. The pZErO-2.1 (this vector contains a lethal gene ccdB (control of cell death) induced by the lacZ promoter. When an insert is present disruption of the lacZ promoter occurs, thereby allowing these cells to be viable. Plasmid DNA was isolated (Wizard Plus SV miniprep DNA purification kit, Promega) from 10-ml cultures selected from a single colony and grown overnight in NZY medium according to the manufacturer's instructions under selection pressure of kanamycin (concentrations as stated previously) until late log phase. The plasmid DNA was digested with XbaI and SacI and separated on a 1.5% agarose gel to verify PCR™ inserts. DNA quantity and purity were estimated spectrophotometrically by recording absorbance at 260 and 280 nm.

5.2.12 DNA Sequencing and Analysis

PCR™ fragments subcloned into pZErO-2.1™ plasmids were sequenced using IRD-41 labeled M13 forward and reverse primers (LI-COR), using a Sequi-Therm™ EXCEL II Kit-LC fluorescent-labeled primer. The dideoxy-chain termination method was carried out according to manufacturer's instructions (Epicentre Technologies), and processed on an automated sequencer (LI-COR, Inc., Model 4000, Lincoln, Nebr.). Analysis of nucleotide and amino acid sequences were performed using DNASIS software (HIBIO DNASIS for Windows, version 2, Hitachi, San Francisco, Calif.) and TBLASTN programs using default parameters (Altschul et al., 1990).

5.3 Example 3

PLD Activity Toward NAPE and PC Among Isoforms

Figure 2:
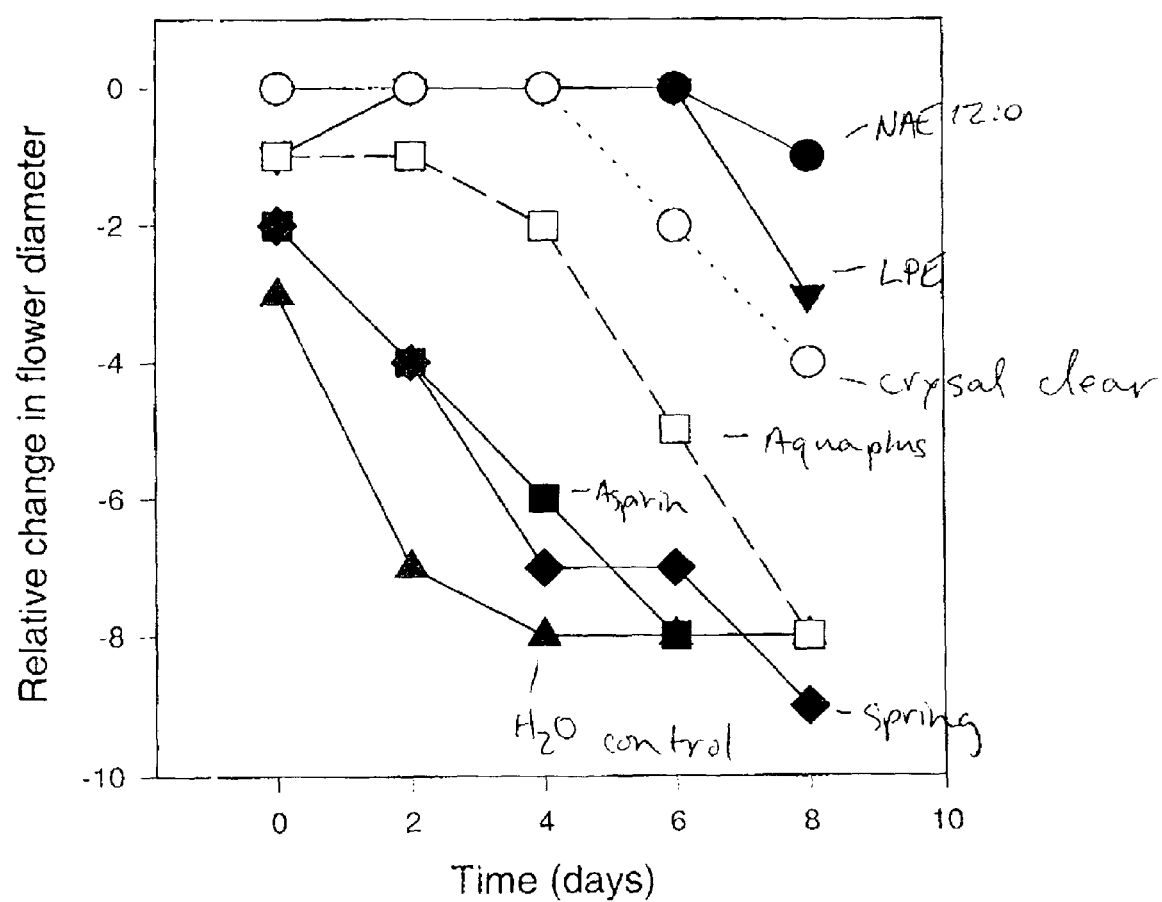
Figure 3:
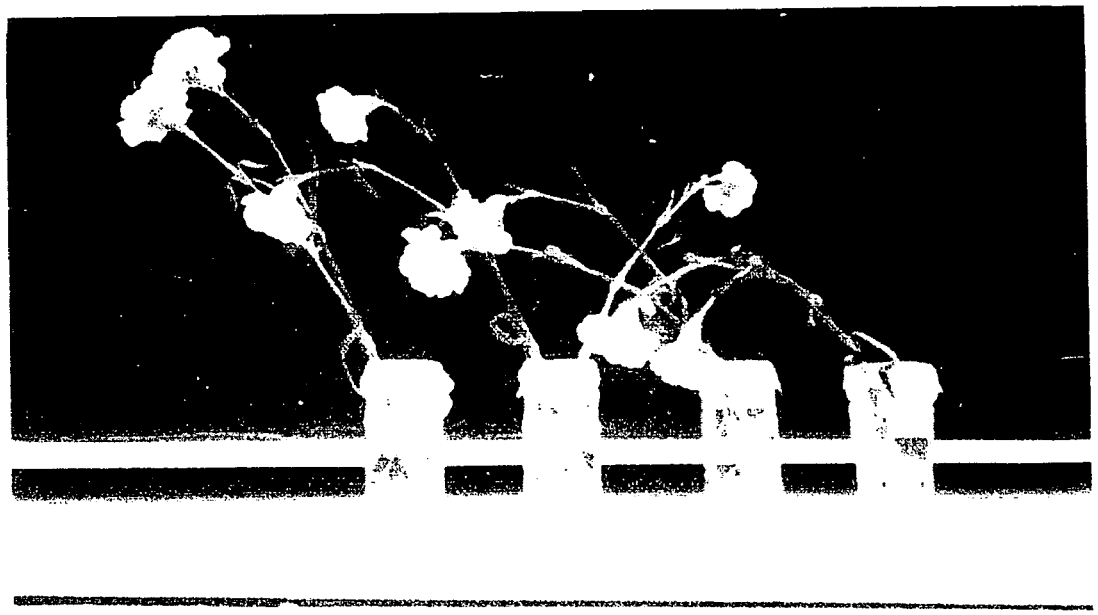
FIG. 3 is a photograph depicting carnations 14 days after treatment, the carnations on the left side of the photo being treated with the present invention and the flowers on the right side of the photo being in plain water only.

The activities of PLD isoforms expressed in E. coli cells were compared (FIG. 2). The formation of radiolabeled phosphatidylalcohol was used to measure PLD activity when radiolabeled PC was used as a substrate. Radiolabeled NAE formation was used to measure PLD activity when radiolabeled NAPE was used as a substrate. NAPE hydrolysis was observed for both PLD β and γ, whereas PLD α and δ hydrolysis of NAPE was not detected. PLD β showed comparable hydrolytic activity toward NAPE and PC: whereas, PLD γ activity toward NAPE was three times greater than toward PC (FIG. 2). NAPE and PC hydrolysis occurred in lipid vesicles containing $PIP_2$, 50 μM $Ca^{2+}$, and over 50% PE. No activity was observed for PLD α in lipid vesicles composed of NAPE alone or NAPE:PC (1:1 molar ratio) (FIG. 2B). The structure of NAPE and the site of cleavage by PLD β and γ are shown in FIG. 3. This study demonstrated that PLD β and γ, which were known to be different from the conventional PLD α (Pappan et al., 1998), were capable of hydrolyzing NAPE.

In addition to radiometric scanning for detection of product, autoradiograms were produced for qualitative comparison. Thin-layer chromatography separation of radiolabeled NAPE (FIG. 2C) or PC (FIG. 2D) showed hydrolysis and/or transphosphatidylation, respectively, by the PLD isoforms expressed in E. coli and Streptomyces chromofuscus PLD (Pappan et al., 1998). Hydrolysis or transphosphatidylation of radiolabeled NAPE and PC, respectively, by PLD β and β was visualized by exposure to x-ray film for approximately 3 days. (Kodak, X-OMAT AR) The formation of NAE was visually detected on autoradiograms of TLC plates for PLD β and γ, but was not for PLD α. As a positive control, S. chromofuscus hydrolyzed NAPE to NAE as documented previously (Schmid et al., 1990). Both PLD β and γ were able to produce phosphatidylethanol from PC (FIG. 2D, lanes 2 and 4).

5.4 Example 4

NAE Effects on PLD α Activity

Figure 4:
FIG. 4 is a photograph depicting carnations 9 days after treatment, the carnations on the right side of the photo being treated with the present invention and the carnations on the left side of the photo being in plain water only.
Figure 5:
FIG. 5 is a photograph depicting yellow/red Gerber daisies 8 days after treatment, the daisies on the left side of the photo being treated with one formulation of the present invention (NF20-XL) and the daisies on the right side of the photo being in plain water only.

NAE inhibited the activity of castor bean PLD α expressed in E. coli cells (FIG. 4). Castor bean PLD α activity was assayed in a high $Ca^{2+}$-dependent assay mixture that contained radiolabeled PC and ethanol as substrates and quantified radiolabeled phosphatidylethanol as product. All NAEs tested were effective inhibitors at high concentrations (200 μM), similar results were reported for lysophosphatidylethanolamine (Ryu et al., 1997). In general, the long-chain, unsaturated NAEs demonstrated less inhibitory effects of castor bean PLD α. Using medium to high concentrations (50–200 μM) of NAE 12:0 and NAE14:0, the castor bean PLD α showed no activity. Submicromolar to low micromolar concentrations of NAE were tested for their inhibitory effectiveness against castor bean PLD α as shown in FIG. 5. Both NAEs were effective inhibitors at low concentrations.

Figure 6:
FIG. 6 is a photograph depicting wildflowers, e.g., purple coneflower, 8 days after treatment, the wildflower on the left side of the photo being treated with one formulation of the present invention (NF20-XL) and the wildflower on the right side of the photo being in plain water only.

To determine the extent of NAE on PLD from different species, the effect of NAE on highly purified cabbage PLD α and S. chromofuscus PLD was studied. FIG. 6 shows NAE12:0 and NAE14:0 at submicromolar to low micromolar amounts were effective inhibitors of cabbage PLD α, but not of S. chromofuscus PLD. PLD activity for S. chromofuscus PLD was measured by the production of radiolabeled phosphatidic acid. The cabbage PLD activity was 37% and 22% of the control for NAE12:0 and NAE14:0, respectively, at a concentration of 1 μM. NAE14:0 appeared to have a somewhat greater inhibitory effect toward cabbage PLD α than NAE12:0. Cabbage PLD activity was unchanged in the presence of 10 μM myristic acid (NAE14:0). Other workers have demonstrated ethanolamine, the head group of NAE, had no inhibitory effect on PLD (Ryu et al., 1997), indicating structural specificity for NAE-type molecules.

Figure 7:
FIG. 7 is a photograph depicting white roses on the first day (top) and after five days (bottom) of treatment, the roses on the right side of the photo being treated with one formulation of the present invention (NF20-XL) and the roses on the left side of the photo being in plain water only.

Increasing substrate concentration (PC) on cabbage PLD was analyzed in the presence and absence of NAE to characterize the type of inhibition of PLD (FIG. 7). The apparent Vmax for cabbage PLD in the absence and presence of 0.01 μM NAE14:0 was 16.7 mol $min^{-1}$ $mg^{-1}$ protein and 11.1 μmol $min^{-1}$ $mg^{-1}$ protein, respectively. The apparent $K_m$ of 2.5 mM for cabbage PLD was unchanged in the presence of NAE14:0. These results suggest noncompetitive inhibition of cabbage PLD by NAE14:0, with an apparent $K_i$ for NAE14:0 of 0.02 μM.

Table 2 summarizes the $IC_{50}$ values for all of the NAEs tested on castor bean PLD α. Inhibitor concentration of the different NAE species resulting in 50% of the maximal activity ranged from 0.1 μM for NAE14:0 to 80 μM for NAE18:3, this accounts for an 800-fold difference in inhibitory effects of the different NAE species. Together these results clearly demonstrate that NAE (especially NAE12:0 and NAE14:0) have an inhibitory effect on plant PLD α. NAE inhibition of PLD α raises the possibility that of NAE acts as a lipid mediator in vivo to regulate PLD α activity. Although the A. thalania PLD β and γ were not tested for activity in the presence of NAEs, the NAE concentration when hydrolyzed by the PLD β and γ was approximately 10 μM.

5.5 Example 5

Isolation and DNA Sequence of a PLD β Gene in Tobacco

Figure 8:
FIG. 8 is a photograph depicting red roses 48 hours after treatment, the roses on the left side of the photo being treated with one formulation of the present invention (NF20-XL) and the roses on the right side of the photo being in plain water only.
Figure 9:
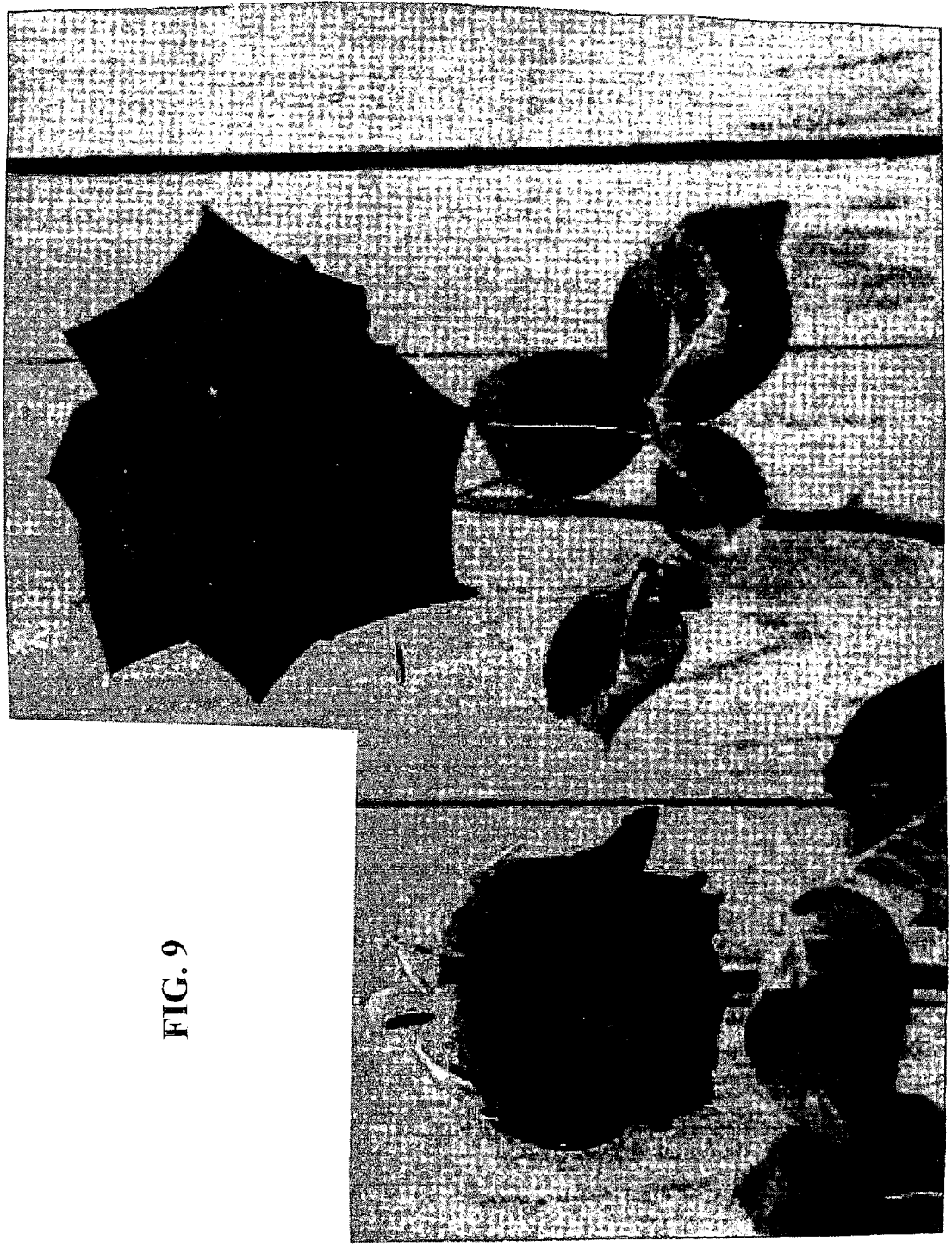
FIG. 9 is a photograph depicting red roses 96 hours after treatment, the rose on the left side of the photo being treated with one formulation of the present invention (NF20-XL) and the rose on the right side of the photo being in plain water only.
Figure 10:
FIG. 10 is a photograph depicting white carnations 10 days after treatment, the carnation on the right side of the photo being treated with one formulation of the present invention (NF20-XL) and the carnation on the left side of the photo being treated with a commercially-available floral treatment product (Aquaplus™).

To better understand the role of PLD in NAPE metabolism, molecular analysis was performed to determine if PLD β or γ were present in tobacco cell suspensions. A pair of degenerate PCR™ primers were designed based on the amino acid sequences of the *A. thalania* PLD β (Pappan et al., 1997a; 1997b) and PLD γ (Qin et al., 1997) gene products. A cDNA library was constructed from mRNA isolated from a *Nicotiana tabacum* NT-1 cell line in early exponential growth phase (obtained from Dr. G. An, Washington State University, Pullman, Wash.). A cDNA fragment was amplified from the tobacco cDNA library with a degenerate primer combination (Table 1, Primer −1 and +5) using PCR™. The PCR™ fragment was approximately 1.2 kb. Subcloning was performed for sequencing analysis using pZErO-2.1™ as the vector. Recombinant clones in *E. coli* Top 10™ cells were obtained and four were randomly chosen for plasmid DNA isolation and restriction digestion (FIG. 8). Vector DNA was digested with restriction enzymes SacI and XbaI. An insert was detected in two of the samples, designated "clone II1" and "clone II6" (see FIG. 8, lanes 10 and 13). The sequence of clone II6 was identical to that of clone II1. To completely characterize the PCR™ product, clone II1 was digested with enzymes at the multiple cloning site of the pZErO-2.1™ vector. Six different enzymes were incubated with clone II1 and electrophoresed in a 1.5% agarose gel (FIG. 9). HindIII cleaved the PCR™ fragment at an internal site (FIG. 9. lane 2). Both the small and the large fragment of clone II1 from HindIII digestion were subcloned and sequenced. FIG. 10 shows the physical map of clone II1 showing the internal restriction site for HindIII, the multiple cloning site, and the direction of the M13 forward and reverse primers used in the sequencing reactions.

Both strands of the cDNA fragment in the pZErO-2.1™ vector designated clone II1 and the subfragment thereof were sequenced using M13 forward and reverse primers. The cDNA fragment was 1170 bp. The deduced amino acid sequence is shown below the nucleotide sequence in FIG. 11. The degenerate primers used to generate the sequence were found on the 5'- and the 3'-end of the fragment, as indicated by the dashed arrow lines. Included within this 390 amino acid segment was one putative catalytic domain, denoted HxKxxxxD (SEQ ID NO:15). Using the BLAST program (Altschul et al., 1990) clone II1 had highest homology to *A. thalania* PLD β (GenBank Accession No. U84568), followed by the *A. thalania* PLD γ (GenBank Accession No. KFO2408) over the length of the 1.2-kb fragment.

The deduced amino acid sequence for the tobacco PLD β open reading frame was aligned with amino acid sequences for *Arabidopsis* PLD β, *Arabidopsis* PLD γ and tobacco PLD α (GenBank Accession No. Z84822). This alignment, shown in FIG. 12 indicated a 74% identity between the tobacco PLD clone and the known *A. thalania* PLD β sequence, while 65% and 52% identities were revealed with alignment of the deduced tobacco clone sequence with the *A. thalania* PLD γ and tobacco PLD α, respectively. Based upon the sequence similarity, it is clear that the novel sequence encodes a portion of the PLD expressed in tobacco.

TABLE 2

$IC_{50}$ VALUES OF NAEs FOR THE INHIBITION OF CASTOR BEAN PLD α EXPRESSED IN *E. COLI*[a]

| N-Acylethanolamines | $IC_{50}$ Values (μM) |
|---|---|
| 12:0 | 0.13 |
| 14:0 | 0.10 |
| 16:0 | 5.00 |
| 18:0 | 10.00 |
| 18:1 | 40.00 |
| 18:2 | 30.00 |
| 18:3 | 80.00 |

[a]Values were estimated graphically from data in FIG. 4 and FIG. 5.

5.6 Example 6

Effects of NAEs on Cut Flowers

Because NAE inhibited PLD cc activity in vitro, and because PLD activity has been associated with cellular damage in senescing plant tissues, the effect of NAE-containing solutions was tested as senescence-delaying agents for cut flowers. Several parameters were examined with carnations, stem wilt, and flower cross-sectional width and appearance. For stem wilt, the angle of declination at the second and third nodes from the flower head was measured from photographs taken at 14 days after treatments (Table 3). Flowers were either dipped in agar, or not, then dipped into water or NAE 12:0 at 0.1 mM. The larger the angle reported, the greater the wilt or bend of the stem. Clearly the NAE12:0 provided extended freshness to carnation stems, presumably by acting to inhibit membrane degradation in the carnation stems.

TABLE 3

ANGLE OF BEND OF STEM (WHITE CARNATION) AFTER 14 DAYS

|  | 2nd Node Below Flower Degrees | 3rd Node Below Flower Degrees |
|---|---|---|
| $H_2O$ only (n = 3) | 38/35/48 | 31/46/38 |
| Agar-dipped stem in $H_2O$ (n = 2) | 36/27 | 26/23 |
| Agar-dipped stem In 0.1 mM NAE 12:0 (n = 2) | 27/42 | 31/13 |
| NAE 12:0 only 0.1 mM (n = 3) | 8/16/12 | 8/12/11 |

In related studies, the appearance of visible signs of senescence (brown petals) and size of the carnation corolla were evaluated at different concentrations of NAE12:0 (Table 4). After 14 days, little evidence of flower senescence was noted for flowers treated with 0.04 mM, and the cross-sectional areas measured for these flowers were the largest.

TABLE 4

EFFECTS OF NAE 12:0 ON THE APPEARANCE OF FLOWER BLOOMS (CARNATIONS) AFTER 14 DAYS

|  | Water Only | 0.0004 mM | 0.004 mM | 0.040 mM | 0.4 mM |
|---|---|---|---|---|---|
|  |  | NAE 12:0 Concentration | | | |
| Number of Brown Petals | ++++ | + | + | — | + |

TABLE 4-continued

EFFECTS OF NAE 12:0 ON THE APPEARANCE OF FLOWER
BLOOMS (CARNATIONS) AFTER 14 DAYS

|  | Water Only | 0.0004 mM | 0.004 mM | 0.040 mM | 0.4 mM |
|---|---|---|---|---|---|
|  |  | NAE 12:0 Concentration | | | |
| Size of Flower Bloom (Cross-Sectional Width) | 1.8 cm | 2.6 cm | 3.0 cm | 3.3 cm | 3.1 cm |

A similar result was noted for long-stem pink roses treated with 2 ml of test solution at day zero and left in water for 7 days (Table 5), except that 0.004 mM NAE12:0 was slightly better than 0.04 mM.

TABLE 5

ROSES APPEARANCE (LONG-STEM PINK) AFTER 7 DAYS

|  | H₂O Only | 0.0004 mM | 0.004 mM | 0.04 mM | 0.4 mM |
|---|---|---|---|---|---|
| Size of Flower Bloom | 0.5 cm | 1.0 cm | 2.3 cm * | 1.8 cm * | 1.8 cm |
| (Cross-Sectional Width at Tip) | DID NOT OPEN NECK BENT | | NICE APPEARANCE | | |

*Best Appearance

In a blind comparison of NAE12:0 at 0.2 mM with water or a commercial preparation of Aquaplus®, NAE was far superior in preventing petal collapse in Gerber daisies (Table 6).

TABLE 6

NUMBER OF DAYS BEFORE WILTING (RED GERBER DAISY)
AND PETAL COLLAPSE (RANDOM BLIND COMPARISON)

| Solution | Contents of Solution | Number of Days Before Wilting |
|---|---|---|
| A | H₂O Only | 4 |
| B | Florist Preparation Only (Aquaplus ® dissolved in water according to manufacturer's instructions) | 6 |
| C | Aqueous Solution of NAE 12:0 (0.2 mM) | 12 |

5.7 Example 7

NAEs Preserve the Freshness of Cut Trees and Plant Parts

The freshness and appearance of cut trees and other plant parts is extended by placing the severed parts in a solution containing effective amounts of one or more NAE compounds.

Pine and juniper cuttings showed dramatic positive effects in terms of needle drop/shedding. Pine branches of equivalent length, tree position, etc. were cut and placed in water or NF20-XL. These data are shown in Table 7. Needles drop was evaluated daily.

TABLE 7

NUMBER OF NEEDLES DROPPED BY CONIFEROUS
ORNAMENTAL PLANT CUTTINGS WITH OR WITHOUT
TREATMENT USING NAE COMPOUNDS

|  | Number of Needles Dropped | |
|---|---|---|
| Day | Water Alone | NF20-XL |
| 1 | 4 | 0 |
| 2 | 0 | 0 |
| 3 | 2 | 1 |
| 4 | 4 | 0 |
| 5 | 3 | 1 |
| 7 | 4 | 0 |
| One week total | 17 | 2 |

Juniper cuttings (same length, similar original mass, similar tree position) treated with water or NF20-XL were compared after one month, and "shed" biomass was collected and weighed: water only −2.52 g; NF20-XL-treated −0.12.

5.8 Example 8

NAE Compositions Preserve the Freshness of Cut Flowers

Formulations of NF20-XL at prescribed NAE dilutions (above) delayed symptoms associated with senescence for the following cut flowers as compared to water or nutrient solution (e.g., Aquaplus®) controls: carnations (white/white with red fringe), store bought; larkspur, store bought; pansies, garden-grown; snapdragons, garden-grown; daisies (white Shasta), garden-grown; Gerbera daisies (peach, pink, yellow and red varieties), store-bought (efficacious whether dosed same day as received at florist or several days later); roses (red "charlotte" and white); wildflowers (Echinaecia, Coreopsis, blanket flower (Gallardia), all garden-grown; positive effect not as clear for *Matthiola* spp ("stock") irises or lilies.

Observations of greenery (including greenery in fresh floral bouquets and leaves on flower stems) are positive (delayed yellowing, browning, etc.) for cuttings placed in NAE-containing solutions.

5.9 Example 9

DNA and Polypeptide Sequences of Novel Tobacco PLD

The amino acid sequence of the antigenic fragment of the novel tobacco PLD β polypeptide disclosed herein is shown below in SEQ ID NO:2. The partial DNA sequence that encodes the PLD polypeptide is shown in SEQ ID NO:1.

5.9.1 Polynucleotide Sequence of Tobacco PLD β Gene (SEQ ID NO:1)

```
GGGAAGTGCTGGGAGGACATGTTCAATGCAATAAATCAGGCTCGTCGGTTG
ATTTACATTACAGGATGGTCAGTGTACCACCTAGTTACACTTGTTAGGGAT
AATGGAAAAGCTGAGGAAAGCATGTTAGGGGAAATTCTCAAGAGGAAATCC
CAAGAAGGTGTGAGAGTACTGCTTCTCATATGGGATGATCCTACCTCTTCG
```

-continued

```
AAGAGCATCTTGGGATACAAAAGTGAAGGAATCATGGGAACTAGTGATGAA

GAAACTCGTCGCTATTTTAAGCATTCTTCAGTGCACGTGCTACTTTGTCCC

CGTTCTGCTGGAAAAGGGCACAGCTGGGTCAAAAAACAGGAAACTGGAACA

ATATACACACATCATCAGAAAACTGTAATAGTGGATGTGGATGCTGGTAAT

TACCAGAGAAAGATTATCGCTTTCGTTGGTGGCCTTGATTTGTGCAAAGGG

CGTTATGATACTCCACAACACCCTATCTTTAAAACATTGCAAAATGTGCAC

AAAGATGACTATCATCAGCCTAACTACACGGGCCCTACTACCGGTTGTCCT

AGAGAACCTTGGCATGATTTACATAGTCGGATCGAGGGGCCTGCTGCATAT

GATGTCCTAACTAACTTCGAGGAGCGCTGGTTGAAGGCTTCAAAGCGCCAT

GGACTTCAAAAGATGAAAGCTTCACAAGATGATGCATTACTCCAACTTGAC

AGGATTTCCGACATATTAAAAATAGCTGATGTCCCTTGCCTAGGAGAAGAT

GATGCAGATACGTGGCACGTGCAGATTTTCCGGTCGATTGACTCCAACTCT

GTTAAAGGTTTCCCCAAAGATCCCAAAGAAGCCACTAACAAGAATCTAGTT

TGTGGCAAGAATGTGCTGATAGATATGAGCATACATACTGCCTATGTAAAG

GCAATCCGAGCTGCCCAACATTTCATCTACATTGAGAACCAGTACTTCCTA

GGGTCCTCATACAATTGGAATAACTACCAAGATTTAGGTGCAAATAACTTG

ATACCGATGGAGATTGCTCTAAAAATTGCCAACAAAATACGGGCAAATGAG

AGGTTTTCAGTATATATAATTGTTCCTATGTGGCCAGAGGGTGTTCCAACC

AGTACTGCTACTCAGAGAATACTTTTTTGGCAACACAAAACCATAGAGATG
```

5.9.2 Polypeptide Sequence of Tobacco PLD β (SEQ ID NO:2)

Three-Letter Designation:

```
GlyLysCysTrpGluAspMetPheAsnAlaIleAsnGlnAlaArgArgLeu

IleTyrIleThrGlyTrpSerValTyrHisLeuValThrLeuValArgAsp

AsnGlyLysAlaGluGluSerMetLeuGlyGluIleLeuLysArgLysSer

GlnGluGlyValArgValLeuLeuLeuIleTrpAspAspProThrSerSer

LysSerIleLeuGlyTyrLysSerGluGlyIleMetGlyThrSerAspGlu

GluThrArgArgTyrPheLysHisSerSerValHisValLeuLeuCysPro

ArgSerAlaGlyLysGlyHisSerTrpValLysLysGlnGluThrGlyThr

IleTyrThrHisHisGlnLysThrValIleValAspValAspAlaGlyAsn

TyrGlnArgLysIleIleAlaPheValGlyGlyLeuAspLeuCysLysGly

ArgTyrAspThrProGlnHisProIlePheLysThrLeuGlnAsnValHis

LysAspAspTyrHisGlnProAsnTyrThrGlyProThrThrGlyCysPro

ArgGluProTrpHisAspLeuHisSerArgIleGluGlyProAlaAlaTyr

AspValLeuThrAsnPheGluGluArgTrpLeuLysAlaSerLysArgHis

GlyLeuGlnLysMetLysAlaSerGlnAspAspAlaLeuLeuGlnLeuAsp

ArgIleSerAspIleLeuLysIleAlaAspValProCysLeuGlyGluAsp

AspAlaAspThrTrpHisValGlnIlePheArgSerIleAspSerAsnSer
```

-continued

```
ValLysGlyPheProLysAspProLysGluAlaThrAsnLysAsnLeuVal

CysGlyLysAsnValLeuIleAspMetSerIleHisThrAlaTyrValLys

AlaIleArgAlaAlaGlnHisPheIleTyrIleGluAsnGlnTyrPheLeu

GlySerSerTyrAsnTrpAsnAsnTyrGlnAspLeuGlyAlaAsnAsnLeu

IleProMetGluIleAlaLeuLysIleAlaAsnLysIleArgAlaAsnGlu

ArgPheSerValTyrIleIleValProMetTrpProGluGlyValProThr

SerThrAlaThrGlnArgIleLeuPheTrpGlnHisLysThrIleGluMet
```

IUAC designation:

```
GKCWEDMFNAINQARRLIYITGWSVYHLVTLVRDNGKAEESMLGEILKRKS

QEGVRVLLLIWDDPTSSKSILGYKSEGIMGTSDEETRRYFKHSSVHVLLCP

RSAGKGHSWVKKQETGTIYTHHQKTVIVDVDAGNYQRKIIAFVGGLDLCKG

RYDTPQHPIFKTLQNVHKDDYHQPNYTGPTTGCPREPWHDLHSRIEGPAAY

DVLTNFEERWLKASKRHGLQKMKASQDDALLQLDRISDILKIADVPCLGED

DADTWHVQIFRSIDSNSVKGFPKDPKEATNKNLVCGKNVLIDMSIHTAYVK

AIRAAQHFIYIENQYFLGSSYNWNNYQDLGANNLIPMEIALKIANKIRANE

RFSVYIIVPMWPEGVPTSTATQRILFTQHKTIEM
```

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

6.0 REFERENCES

The following literature citations as well as those cited above are incorporated in pertinent part by reference herein for the reasons cited in the above text:

U.S. Pat. No. 4,683,195, issued Jul. 28, 1987.
U.S. Pat. No. 4,683,202, issued Jul. 28, 1987.
U.S. Pat. No. 4,873,192, issued Oct. 10, 1989.
U.S. Pat. No. 4,965,188, issued Oct. 23, 1990.
U.S. Pat. No. 5,176,995, issued Oct. 15, 1991.
U.S. Pat. No. 5,324,253, issued Jun. 28, 1994.
U.S. Pat. No. 5,405,765, issued Apr. 11, 1995.
U.S. Pat. No. 5,472,869, issued Dec. 5, 1995.
U.S. Pat. No. 5,484,956, issued Jan. 16, 1996.
U.S. Pat. No. 5,539,082, issued Jul. 23, 1996.
U.S. Pat. No. 5,610,042, issued Mar. 11, 1997.
U.S. Pat. No. 5,610,288, issued Mar. 11, 1997.
U.S. Pat. No. 5,718,709, issued Feb. 17, 1998.

U.S. Pat. No. 5,719,262, issued Feb. 17, 1998.
U.S. Pat. No. 5,736,336, issued Apr. 17, 1998.
U.S. Pat. No. 5,739,119, issued Apr. 14, 1998.
U.S. Pat. No. 5,747,327, issued May 5, 1998.
U.S. Pat. No. 5,759,829, issued Jun. 2, 1998.
U.S. Pat. No. 5,766,855, issued Jun. 16, 1998.
U.S. Pat. No. 5,773,571, issued Jun. 30, 1998.
U.S. Pat. No. 5,786,461, issued Jul. 28, 1998.
U.S. Pat. No. 5,789,573, issued Aug. 4, 1998.
U.S. Pat. No. 5,801,154, issued Sep. 1, 1998.
U.S. Pat. No. 5,874,265, issued Feb. 23, 1999.
U.S. Pat. No. 5,886,244, issued Mar. 23, 1999.
Eur. Pat. Appl. Publ. No. EP 75444.
German Pat. Appl. Publ. 1,542,832.
German Pat. Appl. Publ. 2,654,349.
Japanese Pat. Appl. No. 238901/93.
Swiss Patent No. 432,115.
Aarts, *Meded. Landouwhogeschool Wageningen/Nederland*, 57:1–52, 1957.
Abdullah et al., *Biotechnology*, 4:1087, 1986.
Akoka et al., *Chem. Phys. Lipids*, 46:43–45, 1988.
Altschul et al., *J. Mol. Biol.*, 215:403–410, 1990.
Alvarez, Pennell, Meijer, Ishikawa, Dixon and Lamb, *Cell*, 92:773–784, 1998.
Anderson, Bailey, Dean and Taylor, In: *Polyamines and Ethylene: Biochemistry, Physiology and Interactions, American Society of Plant Physiologists*, Flores, Arteca and Shannon Eds., Rockville, Md. pp. 146–156, 1990.
Bailey, Korcak and Anderson, *Plant Physiol.*, 101:1081–1088, 1993.
Ballas et al., *Nucl. Acids Res.*, 17:7991–7903, 1989.
Bazzi et al., *Biochem.*, 31:1125–1134, 1992.
Beltramo, Stella, Calignano, Lin, Makriyannis and Piomelli, *Science*, 277:1094–1097, 1997.
Boffa, Carpaneto, Allfrey, *Proc. Natl. Acad. Sci. USA*, 92:1901–1905, 1995.
Bomstein, *Biochem. Biophys. Res. Commun.*, 21(1):49–54, 1965.
Bradford, *Anal. Biochem.*, 151:348–349, 1976.
Cai, McAndrew, Leonard, Chapman and Pidgeon, *J. Chromatogr. A.*, 696(1):49–62, 1995.
Callis, Fromm, Walbot, *Genes Devel.*, 1:1183–1200, 1987.
Capecchi, *Cell*, 22(2):479–488, 1980.
Carmen et al., *J. Biol. Chem.*, 270:18711–18714, 1995.
Chapman and Moore, Jr., *Plant Physio.*, 102:761–769, 1993b.
Chapman and Moore, Jr., *Biochim. Biophys. Acta*, 1211:29–36, 1994.
Chapman and Moore, Jr., *Arch. Biochem. Biophys.*, 301:21–33, 1993a.
Chapman and Sprinkle, *J. Plant Physiol.*, 149:277–284, 1996.
Chapman and Sriparameswaran, *Plant Cell Physiol.*, 38:1359–1367, 1997.
Chapman et al., *Arch. Biochem. Biophys.*, 318:401–407, 1995.
Chapman, Conyers-Jackson, Moreau and Tripathy, *Physiol. Plant*, 95:120–126, 1995.
Chapman, Tripathy, Venables and Desouza, *Plant Physiol*, 116(3):1163–1168, 1998.
Chapman, Venables, Markovic, Blair and Bettinger, *Plant Physiol.*, 120(4):1157–1164, 1999.
Clapp, *Clin. Perinatol.*, 20(1):155–168, 1993.
Corey, *Trends Biotechnol.*, 15(6):224–229, 1997.
Corpet, *Nucl. Acids Res.*, 16:10881–10890, 1988.
Cravatt, Giang, Mayfield, Boger, Lerner and Gilula, *Nature*, 384:83–87, 1996.
Cristou et al., *Plant Physiol*, 87:671–674, 1988.
Cullis et al., *Chem. Phys. Lipids*, 40:127–144, 1986.
Curiel, Agarwal, Wagner, Cotten, *Proc. Natl. Acad. Sci. USA*, 88(19):8850–8854, 1991.
Danos and Heard, *Bone Marrow Transplant*, 9(Suppl. 1):131–138, 1992.
Dawson, Clarke and Quarles, *Biochem. J.*, 114:265–270, 1969.
Delledonne, Xia, Dixon and Lamb, *Nature*, 394:585–588, 1998.
DeSouza, Master's Thesis, University of North Texas, Denton, Tex., 1997.
Devane, Hanus, Breuer, Pertwee, Stevenson, Griffin, Gibson, Mandelbaum, Etinger and Mechoulam, *Science*, 258:1946–1949, 1992.
Di Marzo, *Biochim. Biophys. Acta*, 1392:153–175, 1998.
Dittrich et al., *J. Enzyme Inhib.*, 11:67–75, 1996.
Divecha and Irvine, *Cell*, 80:269–278, 1995.
Dixon and Lamb, *Annu. Rev. Plant Physiol. Plant Mol. Biol.*, 41:339–367, 1990.
Dixon, Harrison and Lamb, *Annu. Rev. Plant Pathol.*, 32:479–501, 1994.
Durner, Wendehenner and Klessig, *Proc. Natl. Acad. Sci. USA*, 95:10328–10333, 1998.
Dyer et al., *Plant Physiol.*, 109:1497–1501, 1995.
Dyer et al., *Plant Physiol.*, 105:715–724, 1994.
Ebel and Scheel, In: *Genes Involved in Plant Defense*, Boller and Meins, Jr., Eds., Springer-Verlag, New York, N.Y., pp 183–205, 1992.
Eglitis and Anderson, *Biotechniques*, 6(7):608–614, 1988.
Eichholtz et al., *Somat. Cell Mol. Genet.*, 13(1):67–76, 1987.
Ella et al., *Biochem. J.*, 314:15–19, 1996.
Fan et al., *Plant Cell*, 9:2183–2196, 1997.
Fraley et al., *Bio/Technology*, 3:629–635, 1985.
Fromm, Taylor, Walbot, *Proc. Natl. Acad. Sci. USA*, 82(17):5824–5828, 1985.
Fujimura et al., *Plant Tissue Cult. Lett.*, 2:74, 1985.
Furman-Matarasso, Cohen, Du, Chejanovsky, Hanania and Avni, *Plant Physiol.*, 121:345–352, 1999.
GAP, BESTFIT, BLAST, FASTA, and TFASTA in the Wisconsin Genetics Software Package, Genetics Computer Group (GCG), 575 Science Drive, Madison, Wis., USA.
Good and Nielsen, *Antisense Nucleic Acid Drug Dev.*, 7(4):431–437, 1997.
Goodman and Novacky, *Cell*, 77: 551–563, 1994.
Graham and van der Eb, *Virology*, 54(2):536–539, 1973.
Guerineau et al., *Mol. Gen. Genet.*, 262:141–144, 1991.
Hammond et al., *J. Biol. Chem.*, 270: 29640–29643, 1995.
Hanahan and Chaikoff, *J. Biol. Chem.*, 169:699, 1947.
Hanania and Avni, *Plant J.*, 12:113–120, 1997.
Hanvey et al., *Science*, 258:1481–1485, 1992.
Heller et al., *Biochem. Biophys, Acta*, 369:397–410, 1974.
Higgins et al., *Gene*, 73:237–244, 1988.
Higgins et al., *Comp. Appl. Biosci*, 5:151–153, 1989.
Hilber et al., Curr. Genet., 25(2):124–127, 1994.
Huang et al., *Comp. Appl. Biosci.*, 8:155–165, 1992.
Jorgensen et al., *Mol. Gen. Genet.*, 207:471, 1987.
Joshi et al., *Nucl. Acids Res.*, 15:9627–9639, 1987.
Kaiser and Kezdy, *Science*, 223:249–255, 1984.
Kanfer et al., *FEBS Lett.*, 383:6–8, 1996.
Kawabe et al., *J. Biochem.*, 123:870–875, 1998.
Kim et al., *J. Biol. Chem.*, 271:25213–25219, 1996.
Klee et al., *Bio/Technology*, 3:637–642, 1985.
Kodaki and Yamashita, *J. Biol. Chem.*, 272:11408–11413, 1997.
Kopka et al., *Plant Mol. Biol.*, 36:627–637, 1998.

Kruszka and Gross, *J. Biol. Chem.*, 269:14345–14348, 1994.
Kuby, *Immunology 2nd Edition*, W. H. Freeman & Company, NY, 1994.
Kunkel, *Proc. Natl. Acad. Sci. USA*, 82:488–492, 1985.
Kunkel, Roberts, Zabour, *Methods Enzymol.*, 154:367–382, 1987.
Lafleur et al., *Biochem. Cell Biol.*, 68:1–8, 1990.
LaFrance et al., *Biophys. J*, 72:2559–568, 1997.
Lamb and Dixon, *Annu. Rev. Plant Physiol. Plant Mol. Biol.*, 48:251–275, 1997.
Lambrecht and Ulbrich-Hofmann, *Biol. Chem. Hoppeseyler*, 373(2):81–88, 1992.
Lee et al., *J. Biol. Chem.*, 272:15986–15992, 1997.
Lee, *Plant Sci.*, 59:25–33, 1989.
Lorz et al., *Mol. Gen. Genet.*, 199:178, 1985.
Lukowski et al., *J. Biol. Chem.*, 271: 36–43, 1996.
Maloy et al., In: *Microbial Genetics*, 2nd Ed., Jones and Bartlett Publishers, Boston, Mass., 1994.
Marcotte et al., *Nature*, 335:454, 1988.
McAndrew and Chapman, *Biochim. Biophys. Acta*, 1390(1): 21–36, 1998.
McAndrew and Chapman, *Biochim. Biophys. Acta*, 1390: 21–36, 1998.
McAndrew, Leonard and Chapman, *Biochim. Biophys. Acta*, 1256:310–318, 1995.
McCormick et al., *Plant Cell Reports*, 5:81–84, 1986.
Mogen et al., *Plant Cell*, 2:1261–1272, 1990.
Mollegaard, Buchardt, Egholm, Nielsen, *Proc. Natl. Acad. Sci. USA*, 91(9):3892–3895, 1994.
Munnik et al., *Biochim. Biophys. Acta.*, 1389:222–272, 1998.
Munnik, *Plant Cell*, 7:2197–2210, 1995.
Munroe et al., *Gene*, 91:151–158, 1990.
Nakamura, *J. Lipid Mediators Cell Signal.*, 14(1–3):197–202, 1996.
Nakamura et al., *Proc. Natl. Acad. Sci. USA*, 93:4300–4304, 1996.
Natarajan et al., *Biochim. Biophys. Acta*, 878:32–41, 1986.
Natarajan et al., *Biochim. Biophys. Acta.*, 664:445–448, 1981.
Needleman et al., *J. Mol. Biol.*, 48:443, 1970.
Nielsen et al., *Anticancer Drug Des.*, 8(1):53–63, 1993.
Nielsen, Egholm, Berg, Buchardt, *Science*, 254(5037):1497–1500, 1991.
Orum, Nielsen, Egholm, Berg, Buchardt, Stanley, *Nucl. Acids Res.*, 21(23):5332–5336, 1993.
Orum, Nielsen, Jorgensen, Larsson, Stanley, Koch, *BioTechniques*, 19(3):472–480, 1995.
Pappan and Wang, *Arch. Biochem. Biophys.*, 368:347–353, 1999.
Pappan et al., *J. Biol. Chem.*, 272:7048–7052, 1997b.
Pappan et al., *J. Biol. Chem.*, 272:7055–7061, 1997a.
Pappan, Austin-Brown, Chapman and Wang, *Arch. Biochem. Biophys.*, 353:131–140, 1998.
Pearson et al., *Proc. Natl. Acad. Sci. USA*, 85:2444, 1988.
Perry-O'Keefe, Yao, Coull, Fuchs, Egholm, *Proc. Natl. Acad. Sci. USA*, 93(25):14670–14675, 1996.
Person et al., *Methods Molec. Biol.*, 24:307–331, 1994.
Pike and Casey, *J. Biol. Chem.*, 271:26453–26456, 1996.
Ponting and Kerr, *Prot. Sci.*, 5:914–922, 1996.
Potrykus, Paszkowski, Saul, Petruska, Shillito, *Mol. Gen. Genet.*, 199(2):169–177, 1985.
Prokop and Bajpai, "Recombinant DNA Technology I," *Ann. N.Y. Acad. Sci.*, Vol. 646, 1991.
Proudfoot, *Cell*, 64:671–674, 1991.
Qin et al., *J. Biol. Chem.*, 272:28267–28273, 1997.
Rasmussen and Dixon, *Plant Cell*, 11:1537–1552, 1999.
Ritchie and Gilroy, *Proc. Natl. Acad. Sci. USA*, 95(5): 2697–2702, 1998.
Rogers et al., In: *Methods For Plant Molecular Biology*, Weissbach and Weissbach, Eds., Academic Press Inc., San Diego, Calif., 1988.
Rompp, In: *Chemie-Lexikon*, (Dictionary of Chemistry), Franckh'sche Verlagsbuchhandlung Stuttgart, p. 733, 1966.
Rose et al., *Proc. Natl. Acad. Sci. USA*, 92:12151–12155, 1995.
Roughan, Slack and Holland, *Lipids*, 13:497–503, 1978.
Ryu and Wang, *Biochim. Biophys. Acta.*, 1303:243–250, 1996.
Ryu and Wang, *Plant Physiol.*, 108:713–719, 1995.
Ryu et al., *Proc. Natl. Acad. Sci. USA*, 94:12717–12721, 1997.
Sandoval, Huang, Garrett, Gage and Chapman, *Plant Physiol.*, 109:269–275, 1995.
Sanfacon et al., *Genes Dev.*, 5:141–149, 1991.
Schmid et al., *Prog. Lipid Res.*, 29:1–43, 1990.
Schmid, Schmid and Natarajan, *Chem. Phys. Lipids*, 80:133–142, 1996.
Schmid, Schmid and Natarajan, *Prog. Lipid Res.*, 29:1–43, 1990.
Segal, In: *Biochemical Calculations*, 2nd Edition, John Wiley & Sons, New York, 1976.
Seidman et al., In: *Current Protocols in Molecular Biology*, V. B. Clianda, (Ed.), John Wiley & Sons, pp. 1.8.1–1.8.10, 1997.
Serrano et al., *Scientia Horticulturae*, 44(1–2):127–134, 1990.
Singer et al., *Annu. Rev. Biochem.*, 66:475–509, 1997.
Smith and Hood, *Crop Science*, 35:301–309, 1995.
Smith et al., *Adv. Appl. Math.*, 2:482, 1981.
Spielmann et al., *Mol. Gen. Genet.*, 205:34, 1986.
Sung et al., *EMBO J.*, 16(15):4519–4530, 1997.
Takano et al., *J. Jpn. Soc. Food Sci. Technol.*, 34:8–13, 1987.
Thisted, Just, Petersen, Hyldig-Nielsen, Godtfredsen, *Cell Vision*, 3:358–363, 1996.
Tomes et al., *Plant Mol. Biol.*, 14:261–268, 1990.
Toriyama et al., *Theor Appl. Genet.*, 73:16, 1986.
Tripathy, Venables and Chapman, *Plant Physiol.*, 121:1299–1308, 1999.
Uchimiya et al., *Mol. Gen. Genet.*, 204:204, 1986.
Ueki et al., *Plant Cell Physiol.*, 35:903–914, 1995.
Vain et al., *Plant Cell Rep.*, 12:84–88, 1993.
Veen et al., *Planta*, 140:93–96, 1978.
Venable et al., *J. Biol. Chem.*, 271:24800–24805, 1996.
Veselkov, Demidov, Nielsen, Frank-Kamenetskii, *Nucl. Acids Res.*, 24(13):2483–2487, 1996.
Vickers, Griffith, Ramasamy, Risen, Freier, *Nucl. Acids Res.*, 23(15):3003–3008, 1995.
Wagner, Zatloukal, Cotten, Kirlappos, Mechtler, Curiel, Birnstiel, *Proc. Natl. Acad. Sci. USA*, 89(13):6099–6103, 1992.
Waksman et al., *J. Biol. Chem.*, 271:2361–2364, 1996.
Walker and Gaastra, Eds., *Techniques in Molecular Biology*, MacMillan Publishing Company, New York, 1983.
Wan and Wilkins, *Anal. Biochem.*, 223(1); 7–12, 1994.
Wang et al., *Plant Mol. Biol.*, 11:433–439, 1988.
Wang et al., *J. Biol. Chem.*, 269:20312–20317, 1994.
Wang et al., *Arch. Biochem. Biophys.*, 306:486–494, 1993.
Wang, *Trends Plant Sci.*, 2:261–266, 1997.
Wang, In: "*Lipid Metabolism in Plants*," Moore Jr., Ed., CRC Press, Boca Raton, Fla., pp. 505–525, 1993.
Wang, *J. Am. Chem. Soc.*, 118:7667–7670, 1996.
Wang, *Prog. Lipid Res.* 39:109–149, 2000.

Wilson and Rinne, *Plant Physiol.*, 54:744–747, 1974.
Wong and Neumann, *Biochim. Biophys. Res. Commun.*, 107(2):584–587, 1982.
Xu et al., *Plant Physiol.*, 111: 101–107, 1996.
Yamada et al., *Plant Cell Rep.*, 4:85, 1986.
Yang, *HortScience*, 15(3 Pt. 1):238–243, 1980.
Yang et al., *Proc. Natl. Acad. Sci. USA*, 87:4144–4148, 1990.

What is claimed is:

1. A composition comprising:
   (a) at least a first compound of the formula:

RCONHCH$_2$CH$_2$OH wherein R is optionally branched or straight chain, saturated or unsaturated C$_8$–C$_{20}$ alkyl, in an amount of from about 0.4 µM to about 400 µM; said amount effective to prolong the freshness or the aesthetic appearance of a plant, a flower, a fruit or a plant cutting;
   (b) at least a first plant hormone selected from the group consisting of an auxin, a gibberellin and a cytokinin; and
   (c) a horticulturally-acceptable vehicle.

2. The composition of claim 1, wherein said compound has the formula:

RCONHCH$_2$CH$_2$OH wherein R is optionally branched or straight chain, saturated C$_8$–C$_{20}$ alkyl.

3. The composition of claim 2, wherein said compound is selected from the group consisting of NAE10:0 (N-caproylethanolamine), NAE11:0, NAE12:0 (N-lauroylethanolamine), NAE13:0, NAE14:0 (N-myristoylethanolamine), NAE15:0, NAE16:0 (N-palmitoylethanolamine), NAE17:0, NAE18:0 (N-stearoylethanolamine), NAE19:0, NAE20:0 (N-arachidoylethanolamine), and a mixture thereof.

4. The composition of claim 3, wherein said compound is selected from the group consisting of NAE10:0 (N-caproylethanolamine), NAE12:0 (N-lauroylethanolamine), NAE14:0 (N-myristoylethanolamine), NAE16:0 (N-palmitoylethanolamine), NAE18:0 (N-stearoylethanolamine), NAE20:0 (N-arachidoylethanolamine), and a mixture thereof.

5. The composition of claim 4, wherein said compound is N-lauroylethanolamine (NAE12:0), N-myristoylethanolamine (NAE14:0), or a mixture thereof.

6. The composition of claim 5, wherein said compound is N-lauroylethanolamine (NAE12:0).

7. The composition of claim 1, wherein said compound has the formula:

RCONHCH$_2$CH$_2$OH wherein R is optionally branched or straight chain, unsaturated C$_8$–C$_{20}$ alkyl.

8. The composition of claim 7, wherein said compound is selected from the group consisting of NAE10:1, NAE10:2, NAE10:3, NAE11:1, NAE11:2, NAE11:3, NAE12:1, NAE12:2, NAE12:3, NAE13:1, NAE13:2, NAE13:3, NAE14:1, NAE14:2, NAE14:3, NAE15:1, NAE15:2, NAE15:3, NAE16:1 (N-palmitoleoylethanolamine), NAE16:2, NAE16:3, NAE17:1, NAE17:2, NAE17:3, NAE18:1 (N-vaccenoylethanolamine), NAE18:2 (N-linoleoylethanolamine), NAE18:3 (N-linolenoylethanolamine), NAE19:1, NAE19:2, NAE19:3, NAE20:1, NAE20:2 (8,11-icosadienoylethanolamine), NAE20:3 (5,8,11-icosatrienoylethanolamine), and a mixture thereof.

9. The composition of claim 8, wherein said compound is NAE10:1, NAE10:2, NAE11:1, NAE11:2, NAE11:3, NAE12:1, NAE12:2, NAE12:3, NAE13:1, NAE13:2, NAE13:3, NAE14:1, NAE14:2, NAE14:3, NAE15:1, NAE15:2, NAE15:3, NAE16:1 (N-palmitoleoylethanolamine), NAE16:2, NAE16:3, or a mixture thereof.

10. The composition of claim 1, wherein said vehicle comprises at least a first nutrient source for said plant, flower, fruit, or plant cutting.

11. The composition claim 10, wherein said nutrient comprises a lipid, a carbohydrate, or an amino acid.

12. The composition of claim 11, wherein said carbohydrate is selected from the group consisting of lactose, dextrose, fructose, sucrose, glucose, sorbitol, mannitol, inositol, and a mixture thereof.

13. The composition of claim 1, wherein said vehicle comprises at least a first surfactant.

14. The composition of claim 13, wherein said surfactant is selected from the group consisting of polyoxyethylene sorbitan monolaurate, monopalmitate monostearate, ethoxylated alkyl phenols, a hydrogenated oil, and a mixture thereof.

15. The composition of claim 1, wherein said vehicle comprises at least a first buffer.

16. The composition of claim 15, wherein said buffer is selected from the group consisting of acetate, bicarbonate, citrate, succinate, malate, Tris-(hydroxymethyl)-aminomethane (TRIS); 2-(N-Morpholino)-ethanesulfonic acid (MES); N-[2-hydroxyethyl]piperazine-N'-[2-ethanesulfonic acid] (HEPES); 3-(N-Morpholino)-propanesulfonic acid (MOPS); N,N-Bis-(2-hydroxyethyl)-2-aminoethanesulfonic acid (BES); Bis-(2-hydroxyethyl)-imino-tris-(hydroxymethyl)-methane (BIS-TRIS), and a mixture thereof.

17. The composition of claim 1, wherein said vehicle comprises at least a first osmoregulant.

18. The composition of claim 17, wherein said osmoregulant is selected from the group consisting of a salt, a carbohydrate, a polyol, a polyethylene glycol, and a mixture thereof.

19. The composition of claim 1, further comprising at least a first antifungal, bacteriostatic, or bactericidal agent.

20. The composition of claim 19, wherein said bactericidal agent is selected from the group consisting of 8-hydroxyquinoline citrate, sodium dichloroisocyanurate, 1,3-dichloro-5,5-dimethyhydantoin, and a mixture thereof.

21. The composition of claim 1, further comprising an alcohol.

22. The composition of claim 1, wherein said compound is N-lauroylethanolamine (NAE12:0), N-myristoylethanolamine (NAE14:0), or a mixture thereof, and wherein said composition further comprises a lecithin.

23. The composition of claim 1, further comprising at least a second anti-senescent component.

24. The composition of claim 23, wherein said second anti-senescent component comprises a second distinct N-acylethanolamine selected from the group consisting of NAE10:0 (N-caproylethanolamine), NAE12:0 (N-lauroylethanolamine), NAE14:0 (N-myristoylethanolamine), NAE16:0 (N-palmitoylethanolamine), NAE18:0 (N-stearoylethanolamine), NAE20:0 (N-arachidoylethanolamine), NAE16:1 (N-palmitoleoylethanolamine), NAE18:1 (N-vaccenoylethanolamine), NAE18:2 (N-linoleoylethanolamine), NAE18:3 (N-linolenoylethanolamine), NAE20:1, NAE20:2 (8,11-icosadienoylethanolamine), NAE20:3 (5,8,11-icosatrienoylethanolamine), and a mixture thereof.

25. The composition of claim 1, further comprising a lecithin.

26. The composition of claim 25, wherein said lecithin is a soy lecithin.

27. A composition comprising: (a) at least a first compound selected from the group consisting of NAE10:0 (N-caproylethanolamine), NAE12:0 (N-lauroylethanolamine), NAE14:0 (N-myristoylethanolamine), NAE18:0 (N-stearoylethanolamine), NAE20:0 (N-arachidoylethanoiamine), and a mixture thereof, in an amount of from about 0.1 µM to about 1000 µM; said amount effective to prolong the freshness or the aesthetic appearance of a plant, a flower, a fruit or a plant cutting; (b) a lecithin; and (c) a horticulturally-acceptable vehicle that comprises at least one surfactant.

28. The composition of claim 27, wherein said compound is selected from the group consisting of NAE10:0 (N-caproylethanolamine), NAE11:0, NAE12:0 (N-lauroylethanolamine), NAE13:0, NAE14:0 (N-myristoylethanolamine), NAE15:0, NAE17:0, NAE18:0 (N-stearoylethanolamine), NAE19:0, NAE20:0 (N-arachidoylethanolamine), and a mixture thereof.

29. The composition of claim 28, wherein said compound is selected from the group consisting of NAE10:0 (N-caproylethanolamine), NAE12:0 (N-lauroylethanolamine), NAE14:0 (N-myristoylethanolamine) NAE18:0 (N-stearoylethanolamine), and a mixture thereof.

30. The composition of claim 27, wherein said compound is N-lauroylethanolamine (NAE12:0), said lecithin is soy lecithin, and said surfactant is polyoxyethylenesorbitan monolaurate.

31. The composition of claim 27, further comprising an alcohol.

32. The composition of claim 31, wherein said alcohol is isopropanol.

33. A composition comprising:
(a) at least a first compound selected from the group consisting of NAE10:0, NAE11:0, NAE12:0, NAE13:0, NAE14:0, NAE15:0, NAE17:0, NAE18:0, NAE19:0, NAE20:0, NAE10:1, NAE10:2, NAE10:3, NAE11:1, NAE11:2, NAE11:3, NAE12:1, NAE12:2, NAE12:3, NAE13:1, NAE13:2, NAE13:3, NAE14:1, NAE14:2, NAE14:3, NAE15:1, NAE15:2, NAE15:3, NAE16:1, NAE16:2, NAE16:3, NAE17:1, NAE17:2, NAE17:3, NAE18:1, NAE18:2, NAE18:3, NAE19:1, NAE19:2, NAE19:3, NAE20:1, NAE20:2, NAE20:3, and a mixture thereof, in an amount of from about 0.1 μM to about 1000 μM; said amount effective to prolong the freshness or the aesthetic appearance of a plant, a flower, a fruit or a plant cutting;
(b) at least a first lecithin; and
(c) a horticulturally-acceptable vehicle that comprises at least a first nutrient source for said plant, flower, fruit, or plant cutting.

34. A composition comprising:
(a) at least a first compound of the formula:

RCONHCH$_2$CH$_2$OH wherein R is optionally branched or straight chain, saturated or unsaturated C$_8$–C$_{20}$ alkyl, in an amount of from about 0.1 μM to about 1000 μM; said amount effective to prolong the freshness or the aesthetic appearance of a plant, a flower, a fruit or a plant cutting;
(b) at least a first soy lecithin; and
(c) a horticulturally-acceptable vehicle comprising at least a first alcohol.

35. A composition comprising: about 2 g N-lauroylethanolamine, about 1 g soy lecithin, and about 0.2 ml polyoxyethylenesorbitan monolaurate per 20 ml of isopropanol, wherein the N-lauroylethanolamine is present in an amount of from about 0.1 μM to about 1000 μM.

36. A composition comprising:
(a) at least a first compound selected from the group consisting of NAE10:0, NAE11:0, NAE12:0, NAE13:0, NAE14:0, NAE15:0, NAE17:0, NAE18:0, NAE19:0, NAE20:0, NAE10:1, NAE10:2, NAE10:3, NAE11:1, NAE11:2, NAE11:3, NAE12:1, NAE12:2, NAE12:3, NAE13:1, NAE13:2, NAE13:3, NAE14:1, NAE14:2, NAE14:3, NAE15:1, NAE15:2, NAE15:3, NAE16:1, NAE16:2, NAE16:3, NAE17:1, NAE17:2, NAE17:3, NAE18:1, NAE18:2, NAE18:3, NAE19:1, NAE19:2, NAE19:3, NAE20:1, NAE20:2, and NAE20:3, in an amount of from about 0.4 μM to about 400 μM; and
(b) a horticulturally-acceptable vehicle that comprises at least a first surfactant, and at least a first antifungal, bacteriostatic, or bactericidal agent.

37. A composition comprising:
(a) at least a first and a second distinct compound, each selected from the group consisting of NAE10:0, NAE11:0, NAE12:0, NAE13:0, NAE14:0, NAE15:0, NAE17:0, NAE18:0, NAE19:0, NAE20:0, NAE10:1, NAE10:2, NAE10:3, NAE11:1, NAE11:2, NAE11:3, NAE12:1, NAE12:2, NAE12:3, NAE13:1, NAE13:2, NAE13:3, NAE14:1, NAE14:2, NAE14:3, NAE15:1, NAE15:2, NAE15:3, NAE16:1, NAE16:2, NAE16:3, NAE17:1, NAE17:2, NAE17:3, NAE18:1, NAE18:2, NAE18:3, NAE19:1, NAE19:2, NAE19:3, NAE20:1, NAE20:2, and NAE20:3, and each in an amount of from about 0.4 μM to about 400 μM; and
(b) a horticulturally-acceptable vehicle that comprises at least a first lecithin, and at least a first antifungal, bacteriostatic, or bactericidal agent.

38. A composition comprising:
(a) at least a first compound selected from the group consisting of NAE10:0, NAE11:0, NAE12:0, NAE13:0, NAE14:0, NAE15:0, NAE17:0, NAE18:0, NAE19:0, and NAE20:0, in an amount of from about 0.4 to about 400 μM; and
(b) a horticulturally-acceptable vehicle that comprises at least a first surfactant, and at least a first antifungal, bacteriostatic, or bactericidal agent.

39. A composition comprising:
(a) at least a first compound selected from the group consisting of NAE10:0, NAE11:0, NAE12:0, NAE13:0, NAE14:0, NAE15:0, NAE17:0, NAE18:0, NAE19:0, and NAE20:0, in an amount of from about 0.4 to about 400 μM; and
(b) a horticulturally-acceptable vehicle that comprises at least a first surfactant, and at least a first alcohol.

40. A composition comprising:
(a) at least a first compound of the formula:

RCONHCH$_2$CH$_2$OH wherein R is optionally branched or straight chain, saturated or unsaturated C$_8$–C$_{20}$ alkyl, in an amount of from about 0.4 μM to about 400 μM; said amount effective to prolong the freshness or the aesthetic appearance of a plant, a flower, a fruit or a plant cutting; and
(b) a horticulturally-acceptable vehicle.

41. The composition of claim 40, wherein said vehicle comprises at least a first nutrient source for said plant, flower, fruit, or plant cutting; a first surfactant; a first buffer; a first osmoregulant; water; or a mixture thereof.

42. The composition of claim 40, further comprising at least a first antifungal agent, bacteriostatic agent, bactericidal agent, alcohol, second anti-senescent component, or a mixture thereof.

43. A kit comprising:
a composition comprising:
(a) at least a first compound of the formula:

RCONHCH$_2$CH$_2$OH wherein R is optionally branched or straight chain, saturated or unsaturated C$_8$–C$_{20}$ alkyl, in an amount of from about 0.1 μM to about 1000 μM; said amount effective to prolong the freshness or the aesthetic appearance of a plant, a flower, a fruit or a plant cutting,
(b) at least a first plant hormone selected from the group consisting of an auxin, a gibberellin and a cytokinin, and
(c) a horticulturally-acceptable vehicle; and
instructions for using said kit to delay the senescence of said plant, flower, fruit, or plant cutting.

44. A method of delaying the senescence of a plant, flower, fruit, or plant cutting, said method comprising providing to said flower, fruit, or plant cutting a solution comprising a senescence-delaying amount of:
(a) a compound of the formula:

RCONHCH$_2$CH$_2$OH where R is optionally branched or straight chain, saturated or unsaturated C$_8$–C$_{20}$ alkyl; or
(b) a composition comprising:
at least a first compound of the formula:

RCONHCH$_2$CH$_2$OH wherein R is optionally branched or straight chain, saturated or unsaturated C$_8$–C$_{20}$ alkyl, in an amount of from about 0.1 μM to about 1000 μM; said amount effective to prolong the freshness or the aesthetic appearance of a plant, a flower, a fruit or a plant cutting,
at least a first plant hormone selected from the group consisting of an auxin, a gibberellin and a cytokinin, and
a horticulturally-acceptable vehicle; or
(c) a composition comprising: (a) at least a first compound selected from the group consisting of NAE10:0 (N-caproylethanolamine), NAE12:0 (N-lauroylethanolamine), NAE14:0 (N-myristoylethanolamine), NAE18:0 (N-stearoylethanolamine), and NAE20:0 (N-arachidoylethanoiamine) in an amount of from about 0.1 μM to about 1000 μM; said amount effective to prolong the freshness or the aesthetic appearance of a plant, a flower, a fruit or a plant cutting; (b) a lecithin; and (c) a horticulturally-acceptable vehicle that comprises at least one surfactant; or
(d) a composition comprising:
at least a first compound of the formula:

RCONHCH$_2$CH$_2$OH wherein R is optionally branched or straight chain, saturated or unsaturated C$_8$–C$_{20}$ alkyl, in an amount of from about 0.1 μM to about 1000 μM, said amount effective to prolong the freshness or the aesthetic appearance of a plant, a flower, a fruit or a plant cutting,
at least a first soy lecithin, and
a horticulturally-acceptable vehicle comprising at least a first alcohol.

45. The method of claim 44, wherein said providing comprises applying said solution to said plant, flower, fruit, or plant cutting.

46. The method of claim 45, wherein said applying comprises spraying, coating, soaking, storing or transporting said plant, flower, fruit, or plant cutting with said solution for a length of time effective to delay said senescence.

47. The method of claim 44, wherein said solution is applied to said plant, flower, fruit, or plant cutting under ambient temperature conditions.

48. The method of claim 44, wherein said solution is applied to said plant, flower, fruit, or plant cutting under temperature conditions of from about 4° C. to about 15° C.

49. The method of claim 44, wherein said providing comprises administering said solution to the plant while under cultivation.

50. The method of claim 49, wherein said providing comprises directly administering said solution to the roots, leaves, or flowers of said plant.

51. The method of claim 44, wherein delaying said senescence preserves or improves the appearance, fragrance, freshness, or aesthetic characteristics of said plant, flower, fruit, or plant cutting.

52. The method of claim 44, wherein delaying said senescence reduces the droop, wilt, bloom loss, leaf loss, needle drop, or rate of dehydration of said plant, flower or plant cutting.

53. The method of claim 44, wherein delaying said senescence prolongs or extends the appearance, taste, quality, or shelf life of said fruit.

54. The method of claim 44, wherein said plant cutting is severed from said plant during or after cultivation of said plant.

55. The method of claim 44, wherein said plant cutting comprises a bulb, a bloom, a bud, a flower, a petal, a stem, a branch, a rhizome, a bract, a fruit, a needle, or a leaf.

56. The method of claim 44, wherein said plant is selected from the group consisting of roses, orchids, tulips, daffodils, hyacinths, carnations, chrysanthemums, baby's breath, daisies, gladiolus, agapanthus, anthuria, *Protea, Heliconia, Strilitzia*, lilies, asters, irises, delphiniums, liatris, lisianthus, statis, stephanotis, freesia, dendrobiums, sunflowers, snap dragons, and ornamental foliage.

57. The method of claim 56, wherein said ornamental foliage comprises cut leaves, stalks, stems, branches, limbs, or cut trees.

58. The method of claim 57, wherein said ornamental foliage comprises coniferous foliage.

59. The method of claim 58, wherein said ornamental foliage comprises juniper, fir, pine, cedar, or spruce foliage.

60. The method of claim 57, wherein said ornamental foliage comprises Christmas or holiday trees, wreaths, or garlands.

61. The method of claim 44, wherein the final concentration of said compound in said solution is between about 2 μM and about 200 μM.

62. The method of claim 61, wherein the final concentration of said compound in said solution is between about 4 μM and about 100 μM.

63. The method of claim 44, wherein said solution is provided to said plant, flower, fruit, or plant cutting, for a time of from about 10 minutes to about 28 days.

64. The method of claim 63, wherein said solution is provided to said plant, flower, fruit, or plant cutting, for a time of from about 30 minutes to about 21 days.

65. The method of claim 64, wherein said solution is provided to said plant, flower, fruit, or plant cutting, for a time of from about 1 hour to about 14 days.

66. The method of claim 44, comprising providing to said flower, fruit, or plant cutting a solution comprising a senescence-delaying amount of a compound of the formula:

RCONHCH$_2$CH$_2$OH where R is optionally branched or straight chain, saturated or unsaturated C$_8$–C$_{20}$ alkyl.

67. The method of claim 44, comprising providing to said flower, fruit, or plant cutting a solution comprising a senescence-delaying amount of a composition comprising:
at least a first compound of the formula:

RCONHCH$_2$CH$_2$OH wherein R is optionally branched or straight chain, saturated or unsaturated C$_8$–C$_{20}$ alkyl, in an amount of from about 0.1 μM to about 1000 μM; said amount effective to prolong the freshness or the aesthetic appearance of a plant, a flower, a fruit or a plant cutting,
at least a first plant hormone selected from the group consisting of an auxin, a gibberellin and a cytokinin, and
a horticulturally-acceptable vehicle.

68. A method of prolonging the appearance of a plant, flower, fruit, or plant cutting, said method comprising providing to said flower, fruit, or plant cutting a solution comprising an amount of
(a) a compound of the formula:

RCONHCH$_2$CH$_2$OH where R is optionally branched or straight chain, saturated or unsaturated C$_8$–C$_{20}$ alkyl; or
(b) a composition comprising:
at least a first compound of the formula:

RCONHCH$_2$CH$_2$OH wherein R is optionally branched or straight chain, saturated or unsaturated C$_8$–C$_{20}$ alkyl, in an amount of from about 0.1 μM to about 1000 μM; said amount effective to prolong the freshness or the aesthetic appearance of a plant, a flower, a fruit or a plant cutting,
at least a first plant hormone selected from the group consisting of an auxin, a gibberellin and a cytokinin, and
a horticulturally-acceptable vehicle; or
(c) a composition comprising: about 2 g N-lauroyletha-nolamine, about 1 g soy lecithin, and about 0.2 ml polyoxyethylenesorbitan monolaurate per 20 ml of isopropanol,
effective to prolong the appearance of said plant, flower, fruit, or plant cutting.

69. A method of increasing the shelf life of a plant, flower, fruit, or plant cutting, said method comprising providing to said flower, fruit, or plant cutting a solution comprising an amount of:
(a) a compound of the formula:

RCONHCH$_2$CH$_2$OH where R is optionally branched or straight chain, saturated or unsaturated C$_8$–C$_{20}$ alkyl; or
(b) a composition comprising:
at least a first compound of the formula:

RCONHCH$_2$CH$_2$OH wherein R is optionally branched or straight chain, saturated or unsaturated C$_8$–C$_{20}$ alkyl, in an amount of from about 0.1 μM to about 1000 μM; said amount effective to prolong the freshness or the aesthetic appearance of a plant, a flower, a fruit or a plant cutting,
at least a first plant hormone selected from the group consisting of an auxin, a gibberellin and a cytokinin, and
a horticulturally-acceptable vehicle,
effective to increase the shelf life of said plant, flower, fruit, or plant cutting.

70. The method of claim 69, comprising providing to said flower, fruit, or plant cutting a solution comprising an amount of a compound of the formula:

RCONHCH$_2$CH$_2$OH where R is optionally branched or straight chain, saturated or unsaturated C$_8$–C$_{20}$ alkyl, effective to increase the shelf life of said plant, flower, fruit, or plant cutting.

71. The method of claim 70, wherein said compound is N-lauroylethanolamine (NAE12:0), N-myristoylethanolamine (NAE14:0), or a mixture thereof.

72. A method of extending the freshness or aesthetic appearance of cut flowers, ornamental cut trees, or a plant cutting, said method comprising: providing to said cut flowers, said ornamental cut trees, or said plant cutting, a solution comprising a biologically-effective amount of:
(a) a compound of the formula:

RCONHCH$_2$CH$_2$OH where R is optionally branched or straight chain, saturated or unsaturated C$_8$–C$_{20}$ alkyl; or
(b) a composition comprising:
at least a first compound of the formula:

RCONHCH$_2$CH$_2$OH wherein R is optionally branched or straight chain, saturated or unsaturated C$_8$–C$_{20}$ alkyl, in an amount of from about 0.1 μM to about 1000 μM; said amount effective to prolong the freshness or the aesthetic appearance of a plant, a flower, a fruit or a plant cutting,
at least a first plant hormone selected from the group consisting of an auxin, a gibberellin and a cytokinin, and
a horticulturally-acceptable vehicle,
for a time effective to extend the freshness or aesthetic appearance of said cut flowers, said ornamental cut trees, or said plant cutting.

73. The method of claim 72, comprising providing to said cut flowers, said ornamental cut trees, or said plant cutting, a solution comprising a biologically-effective amount of a compound of the formula:

RCONHCH$_2$CH$_2$OH where R is optionally branched or straight chain, saturated or unsaturated C$_8$–C$_{20}$ alkyl, for a time effective to extend the freshness of aesthetic appearance of said cut flowers, said ornamental cut trees, or said plant cutting.

74. The method of claim 73, wherein said compound is N-lauroylethanolamine (NAE12:0), N-myristoylethanolamine (NAE14:0), or a mixture thereof.

75. A method of extending the vase life of a cut flower or plant cutting, said method comprising: providing to said cut flower or plant cutting a solution comprising an effective amount of:
(a) a compound of the formula:

$$RCONHCH_2CH_2OH$$

where R is optionally branched or straight chain, saturated or unsaturated $C_8–C_{20}$ alkyl; or
(b) a composition comprising:
at least a first compound of the formula:

$$RCONHCH_2CH_2OH$$

wherein R is optionally branched or straight chain, saturated or unsaturated $C_8–C_{20}$ alkyl, in an amount of from about 0.1 μM to about 1000 μM; said amount effective to prolong the freshness or the aesthetic appearance of a plant, a flower, a fruit or a plant cutting,
at least a first plant hormone selected from the group consisting of an auxin, a gibberellin and a cytokinin, and
a horticulturally-acceptable vehicle,
for a time necessary to extend the vase life of said cut flower or said plant cutting.

76. The method of claim 75, comprising: providing to said cut flower or plant cutting a solution comprising an effective amount of a compound of the formula:

$$RCONHCH_2CH_2OH$$

where R is optionally branched or straight chain, saturated or unsaturated $C_8–C_{20}$ alkyl, for a time necessary to extend the vase life of said cut flower or said plant cutting.

77. The method of claim 76, wherein said compound is N-lauroylethanolamine (NAE12:0), N-myristoylethanolamine (NAE14:0), or a mixture thereof.

* * * * *